(12) United States Patent
Tantin

(10) Patent No.: US 12,150,973 B2
(45) Date of Patent: Nov. 26, 2024

(54) OCA-B PEPTIDE CONJUGATES AND METHODS OF TREATMENT

(71) Applicant: University of Utah Research Foundation, Salt Lake City, UT (US)

(72) Inventor: Dean Tantin, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 1016 days.

(21) Appl. No.: 17/051,341

(22) PCT Filed: Apr. 17, 2019

(86) PCT No.: PCT/US2019/027987
§ 371 (c)(1),
(2) Date: Oct. 28, 2020

(87) PCT Pub. No.: WO2019/212752
PCT Pub. Date: Nov. 7, 2019

(65) Prior Publication Data
US 2021/0046153 A1 Feb. 18, 2021

Related U.S. Application Data

(60) Provisional application No. 62/666,325, filed on May 3, 2018.

(51) Int. Cl.
| | |
|---|---|
| A61K 38/16 | (2006.01) |
| A61K 9/00 | (2006.01) |
| A61K 38/08 | (2019.01) |
| A61K 47/64 | (2017.01) |
| A61P 19/02 | (2006.01) |

(52) U.S. Cl.
CPC ............ *A61K 38/16* (2013.01); *A61K 9/0019* (2013.01); *A61K 38/08* (2013.01); *A61K 47/645* (2017.08); *A61P 19/02* (2018.01)

(58) Field of Classification Search
None
See application file for complete search history.

(56) References Cited

U.S. PATENT DOCUMENTS

| | | | |
|---|---|---|---|
| 2003/0105000 A1* | 6/2003 | Pero | C07K 1/047 514/19.3 |
| 2005/0107583 A1* | 5/2005 | Jiang | A61P 9/10 530/324 |
| 2007/0161108 A1 | 7/2007 | Harrer et al. | |
| 2008/0182250 A1 | 7/2008 | Zhao et al. | |
| 2012/0108504 A1 | 5/2012 | Otvos, Jr. | |
| 2015/0266939 A1 | 9/2015 | Vogan et al. | |
| 2016/0024174 A1 | 1/2016 | Odunsi et al. | |

FOREIGN PATENT DOCUMENTS

| | | |
|---|---|---|
| CN | 101327324 A | 12/2008 |
| WO | WO 1991/009958 | 7/1991 |
| WO | WO 1999/067284 | 12/1999 |
| WO | 2003018836 A2 | 3/2003 |
| WO | WO-2019/212752 A1 | 11/2019 |

OTHER PUBLICATIONS

Rudikoff et al. (PNAS USA, 1982, 79: 1979-1983) (Year: 1982).*
Burgess et al. (J of Cell Bio. 111:2129-2138, 1990) (Year: 1990).*
Ibragimova and Wade (Biophysical Journal, Oct. 1999, vol. 77, pp. 2191-2198) (Year: 1999).*
Gura (Science, 1997, 278:1041-1042) (Year: 1997).*
Kaiser (Science, 2006, 313: 1370) (Year: 2006).*
Dimeglio et al. (Lancet 2018 219: 2449-62) (Year: 2018).*
Chen et al. (Advanced Drug Delivery Rev. 2013 65: 1357-1369) (Year: 2013).*
Bergmann CC, et al. "Coronavirus infection of the central nervous system: host-virus stand-off", Nat Rev Microbiol. 2006;4:121-32.
Bird, G.H., et al. (2008) "Synthesis and biophysical characterization of stabilized alpha-helices of BCL-2 domains", Methods Enzymol. 446, 369-386.
Bird, G.H., et al. (2010) "Hydrocarbon double-stapling remedies the proteolytic instability of a lengthy peptide therapeutic," Proc. Natl. Acad. Sci. U. S. A. 107, 14093-14098.
Blanc CA, et al. "FTY720 (fingolimod) modulates the severity of viral-induced encephalomyelitis and demyelination," J Neuroinflammation. 2014;11:138.
Bittner S, et al. "Myelin oligodendrocyte glycoprotein (MOG35-55) induced experimental autoimmune encephalomyelitis (EAE) in C57BL/6 mice," J Vis Exp. 2014; 15;(86).
Caruso A, et al. "Flow cytometric analysis of activation markers on stimulated T cells and their correlation with cell proliferation," Cytometry. 1997; 27:71-6.
Chai JG, et al. "Immobilized anti-CD3 mAb induces anergy in murine naive and memory CD4+ T cells in vitro," Int Immunol. 1997;9:935-44.
Chasman et al. "Crystal structure of an OCA-B peptide bound to an Oct-1 POU domain/octamer DNA complex: specific recognition of a protein-DNA interface," Genes Dev. (1999) 13(20): 2650-7.
Chee J, et al. "Effector-memory T cells develop in islets and report islet pathology in type 1 diabetes," J Immunol. 2014; 192:572-80.
Dickey LL, et al. "MicroRNA-155 enhances T cell trafficking and antiviral effector function in a model of coronavirus-induced neurologic disease," J Neuroinflammation. 2016; 13:240.
Dong C, et al. "ICOS co-stimulatory receptor is essential for T-cell activation and function," Nature. 2001;409:97-101.
Dong C, et al. "Regulation of immune and autoimmune responses by ICOS," J Autoimmun. 2003;21:255-60.
Farth et al. (2015) "Genetic and epigenetic fine mapping of causal autoimmune disease variants," Nature, 518 (7539): 337-43.
Friese MA, et al. "Autoreactive CD8+ T cells in multiple sclerosis: a new target for therapy?", Brain. 2005;128:1747-63.

(Continued)

*Primary Examiner* — Peter J Reddig
(74) *Attorney, Agent, or Firm* — BALLARD SPAHR LLP

(57) ABSTRACT

Disclosed herein, are compounds comprising a peptide, wherein the peptide is OCA-B or an OCA-B fragment thereof; a linker; and a cell penetrating peptide. Also described herein, are methods of administering compounds to subjects for the treatment of Type I diabetes and blocking the interaction between OCA-B and Jmjd1a.

16 Claims, 24 Drawing Sheets

Specification includes a Sequence Listing.

(56) References Cited

OTHER PUBLICATIONS

Gibson et al. (2006) "Expression of the B cell-associated transcription factors PAX5, OCT-2, and BOB.1 in acute myeloid leukemia: associations with B-cell antigen expression and myelomonocytic maturation", Am J Clin Pathol, vol. 126: 916-924.
Goverman J, et al. "The role of CD8(+) T cells in multiple sclerosis and its animal models," Curr Drug Targets Inflamm Allergy. 2005; 4:239-45.
Goverman J. "Autoimmune T cell responses in the central nervous system," Nat Rev Immunol. 2009; 9:393-407.
Graham DSC, et al. "Evidence for unique association signals in SLE at the CD28-CTLA4-ICOS locus in a family-based study," Hum Mol Genet. 2006;15:3195-205.
Grist J.J., et al. "Induced CNS expression of CXCL1 augments neurologic disease in a murine model of multiple sclerosis via enhanced neutrophil recruitment," Eur J Immunol. 2018;48:1199-210.
Held KS, et al. "Generation of a protective T-cell response following coronavirus infection of the central nervous system is not dependent on IL-12/23 signaling," Viral Immunol. 2008;21:173-88.
Henchey, L.K., et al. (2008) "Contemporary strategies for the stabilization of peptides in the alpha-helical conformation," Curr. Opin. Chem. Biol. 12, 692-697.
Kalekar LA, et al. "CD4(+) T cell anergy prevents autoimmunity and generates regulatory T cell precursors," Nat Immunol. 2016; 17:304-14.
Kapil P, et al. "Interleukin-12 (IL-12), but not IL-23, deficiency ameliorates viral encephalitis without affecting viral control," J Virol. 2009; 83:5978-86.
Kawakami N, et al. "Autoimmune CD4+ T cell memory: lifelong persistence of encephalitogenic T cell clones in healthy immune repertoires," J Immunol. 2005;175:69-81.
Kearney ER, et al. "Visualization of peptide-specific T cell immunity and peripheral tolerance induction in vivo," Immunity. 1994;1:327.
Kim L.K., et al. "Oct-1 regulates IL-17 expression by directing interchromosomal associations in conjunction with CTCF in T cells," Mol Cell. 2014;54:56-66.
Kim, Y.W., et al. (2010) "Introduction of all-hydrocarbon i,i+3 staples into alpha-helices via ring-closing olefin metathesis", Org. Lett. 12, 3046-3049.
Kim, Y.W., et al. (2011) "Synthesis of all-hydrocarbon stapled a-helical peptides by ring-closing olefin metathesis," Nat. Protoc. 6, 761-771.
Lane TE, et al. "The pathogenesis of murine coronavirus infection of the central nervous system," Crit Rev Immunol. 2010;30:119-30.
Langrish CL, et al. "IL-23 drives a pathogenic T cell population that induces autoimmune inflammation," J Exp Med. 2005;201:233-40.
Liu MT, et al. "Chemokine expression and viral infection of the central nervous system: regulation of host defense and neuropathology," Immunol Res. 2001; 24:111-9.
Marro BS, et al. "Inducible Expression of CXCL1 within the Central Nervous System Amplifies Viral-Induced Demyelination," J Immunol. 2016; 196:1855-64.
Maurano et al. "Systematic localization of common disease-associated variation in regulatory DNA," (2012) Science, 337(6099): 1190-5.
Patsopoulos NA. "Genetics of Multiple Sclerosis: An Overview and New Directions," Cold Spring Harb Perspect Med. 2018; 8:a028951.
Rottman JB, et al. "The costimulatory molecule ICOS plays an important role in the immunopathogenesis of EAE," 2001;2:605-11.
Rumble JM, et al. "Neutrophil-related factors as biomarkers in EAE and MS," J Exp Med. 2015;212:23-35.
Schafmeister, C.E., et al. (2000) "An All-Hydrocarbon Cross-Linking System for Enhancing the Helicity and Metabolic Stability of Peptides," J. Am. Chem. Soc. 122, 5891-5892.
Segal BM, et al. "IL-12 unmasks latent autoimmune disease in resistant mice," J Exp Med. 1996;184:771-5.
Shakya A, et al. "Oct1 is a switchable, bipotential stabilizer of repressed and inducible transcriptional states," J Biol Chem. 2011;286:450-9.
Shakya A, et al. "Oct1 and OCA-B are selectively required for CD4 memory T cell function," J Exp Med. 2015 ;212:2115-31.
Steinman L. "Immunology of relapse and remission in multiple sclerosis," Annu Rev Immunol. 2014;32:257-81.
Stiles LN, et al. "T cell antiviral effector function is not dependent on CXCL10 following murine coronavirus infection," J Immunol. 2006; 177:8372-80.
Stiles LN, et al. "Differential roles for CXCR3 in CD4+ and CD8+ T cell trafficking following viral infection of the CNS," Eur J Immunol. 2006;36:613-22.
Stiles LN, et al. "CXCL10 and trafficking of virus-specific T cells during coronavirus-induced demyelination," Autoimmunity. 2009;42:484-91.
Tuettenberg A, et al. "The role of ICOS in directing T cell responses: ICOS-dependent induction of T cell anergy by tolerogenic dendritic cells," J Immunol. 2009;182:3349-56.
Vanasek TL, et al. "Antagonistic roles for CTLA-4 and the mammalian target of rapamycin in the regulation of clonal anergy: enhanced cell cycle progression promotes recall antigen responsiveness," J Immunol. 2001;167:5636-44.
Van Heel DA, et al. "Inflammatory bowel disease is associated with a TNF polymorphism that affects an interaction between the OCT1 and NF(-kappa)B transcription factors," Hum Mol Genet. 2002;11:1281-9.
Verdine, G.L. and G.J. Hilinski, (2012) "Stapled peptides for intracellular drug targets," Methods Enzymol. 503, 3-33.
Williamson JS, et al. "Effective clearance of mouse hepatitis virus from the central nervous system requires both CD4+ and CD8+ T cells," J Virol. 1990;64:4589-92.
Yeo L, et al. "Autoreactive T effector memory differentiation mirrors β cell function in type 1 diabetes," J Clin Invest. 2018;128:3460-74.
Yosef N, et al. "Dynamic regulatory network controlling TH17 cell differentiation," Nature. 2013;496:461-8.
International Search Report and Written Opinion were mailed on Jul. 18, 2019 by the International Searching Authority for International Application No. PCT/US2019/027987, filed on Apr. 17, 2019 and published as WO/2019/212752 on Nov. 7, 2019 (Applicant—University of Utah Research Foundation) (14 Pages).
International Preliminary Report on Patentability was mailed on Nov. 3, 2020 by the International Searching Authority for International Application No. PCT/US2019/027987, filed on Apr. 17, 2019 and published as WO/2019/212752 on Nov. 7, 2019 (Applicant—University of Utah Research Foundation) (11 Pages).
Tantin, D.R., et al. "Targeting transcription cofactor OCA-B specifically blocks pancreatic T cell infiltration, cytokine production and elevated glucose in the NOD mouse model of type-1 diabetes (T1D)", Journal of Immunology, May 1, 2018.
European Search Report and Written Opinion issued Dec. 12, 2021 from the European Patent Office for EP 19795922 (Applicant: University of Utah Research Foundation) 6 pages.

\* cited by examiner

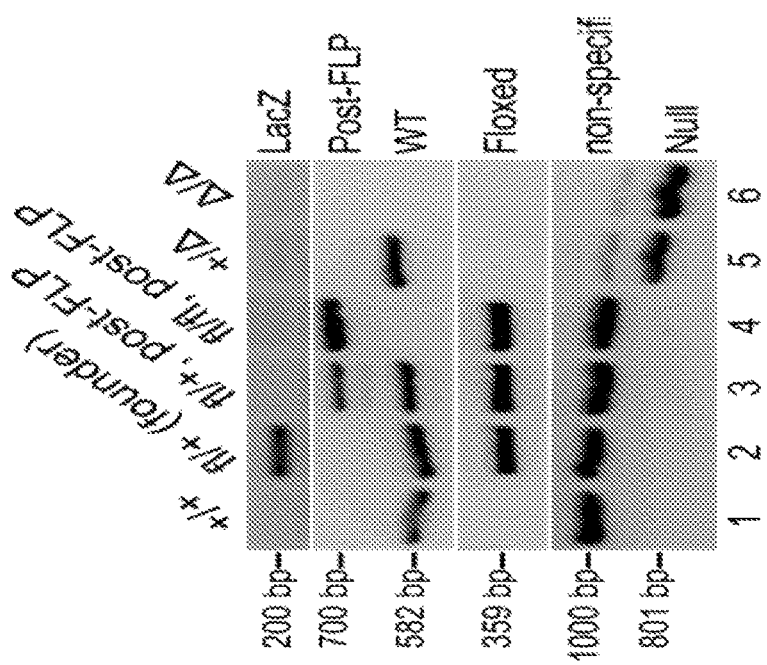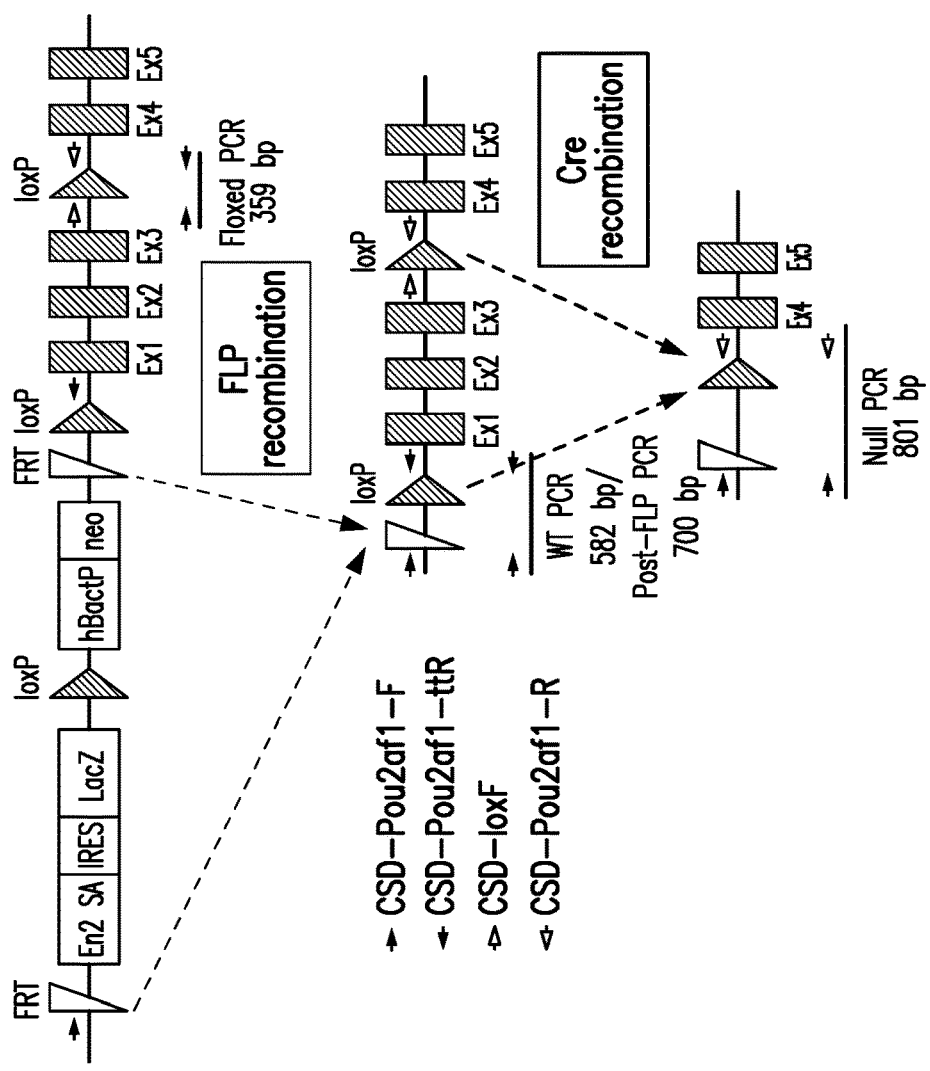
FIG. 4B
FIG. 4A

| Idd locus | Linkage marker | Relative microsatellite size |
|---|---|---|
| 1 | D17Mit34 | B6>NOD |
| 2 | D9Mit25 | NOD>B6 |
| 3 | D3Mit95 | NOD>B6 |
| 4 | D11Nds16 | NOD>B6 |
| 5 | D1Mit5 | NOD>B6 |
| 6 | D6Mit52 | B6>NOD |
| 7 | D7Mit20 | B6>NOD |
| 8,12 | D14Mit11 | NOD>B6 |
| 9,11 | D4Mit59 | NOD>B6 |
| 10 | D3Nds8 | NOD>B6 |
| 13 | D2Mit17 | NOD>B6 |
| 14 | D13Mit61 | NOD>B6 |
| 15 | D5Mit69 | NOD>B6 |

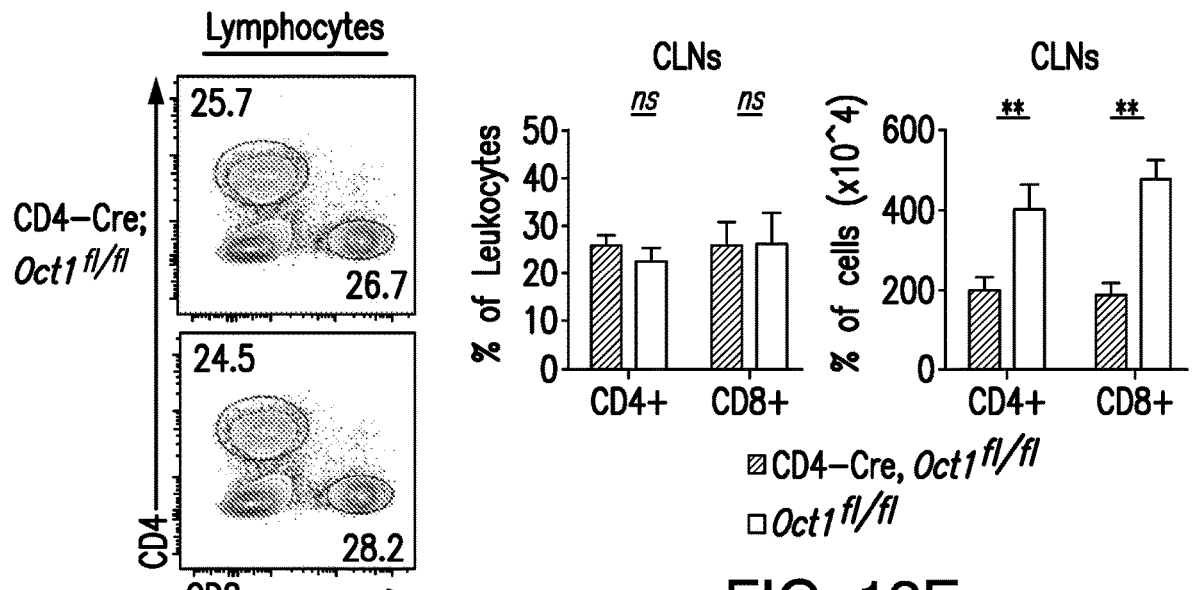
FIG. 12D
FIG. 12E
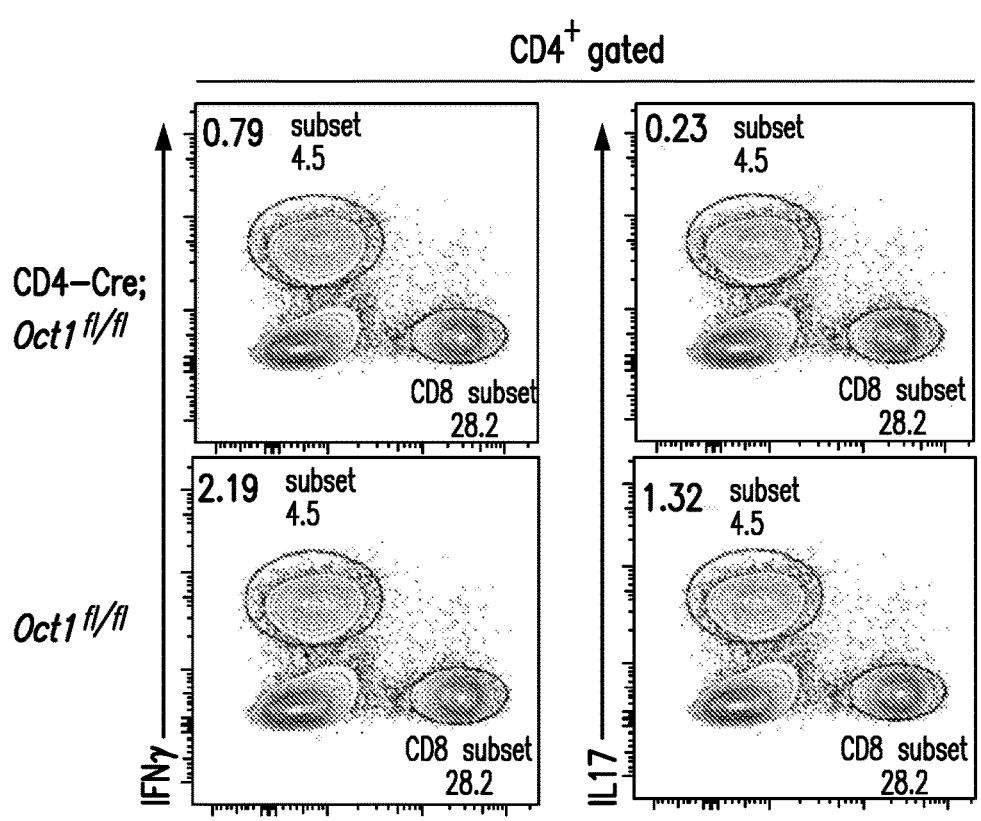
FIG. 12F

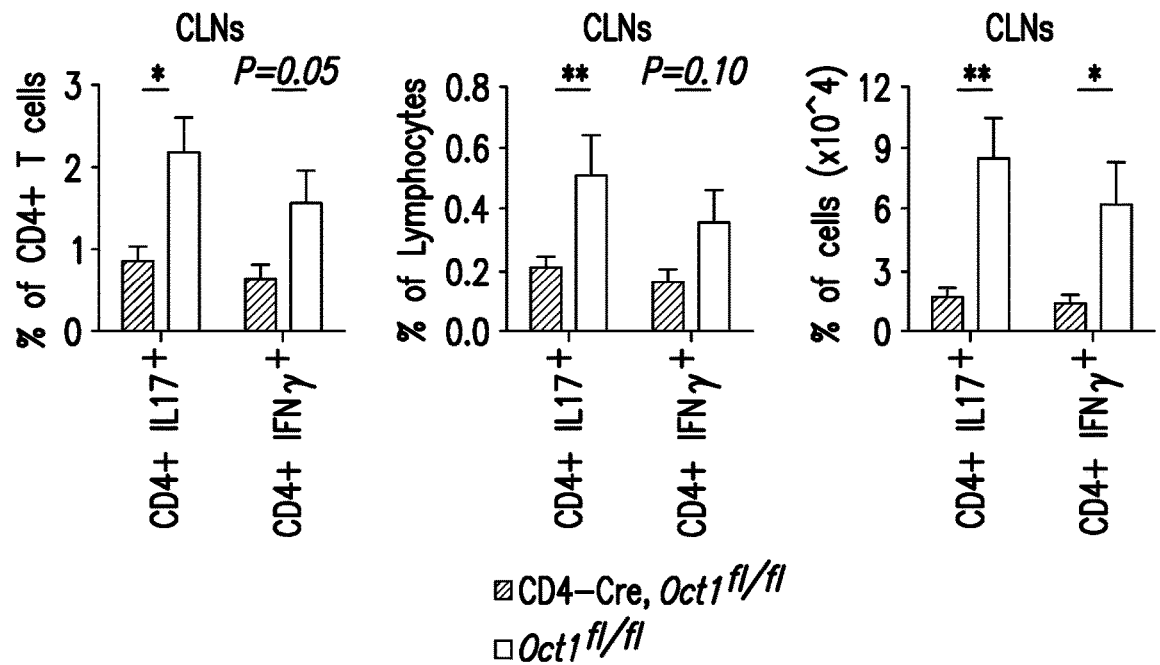
FIG. 12G
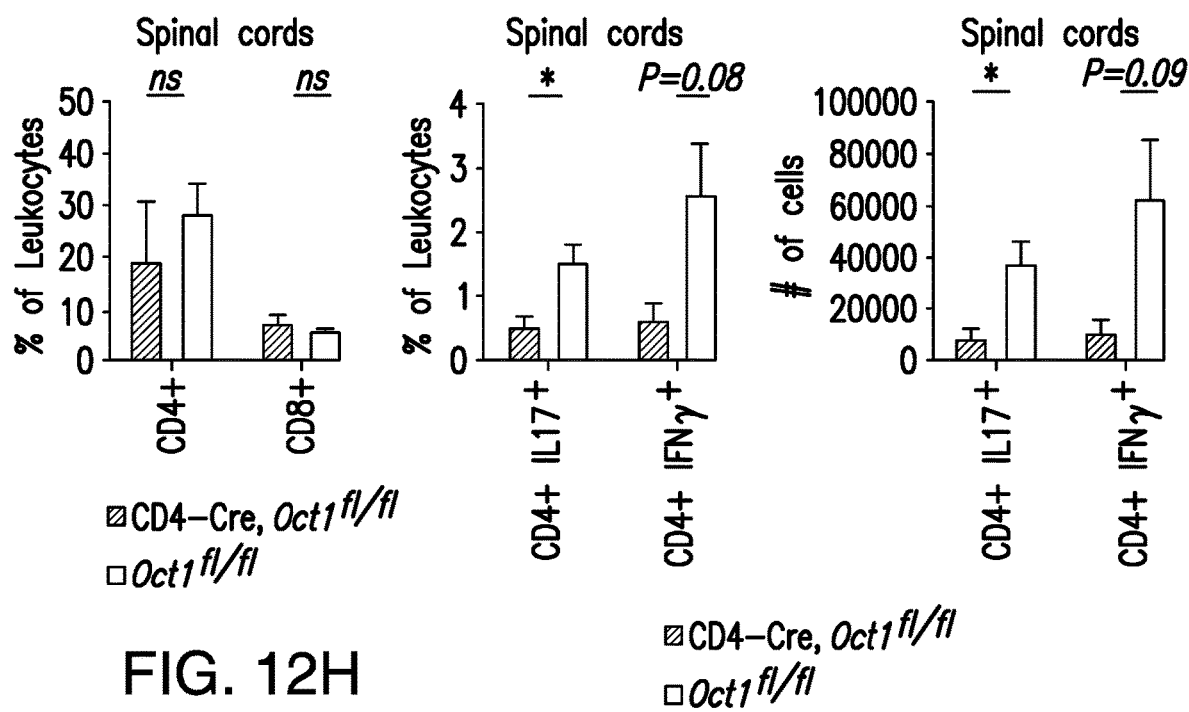
FIG. 12H
FIG. 12I

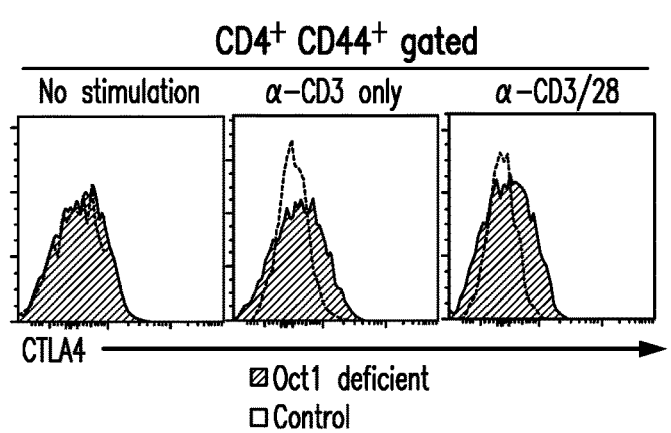
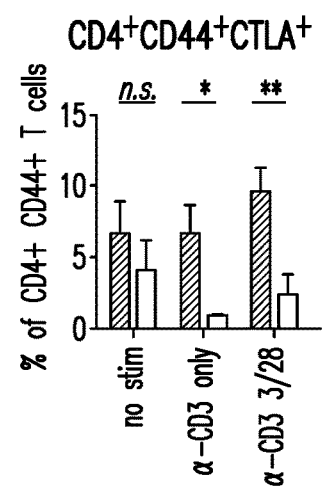
FIG. 13E
FIG. 13F
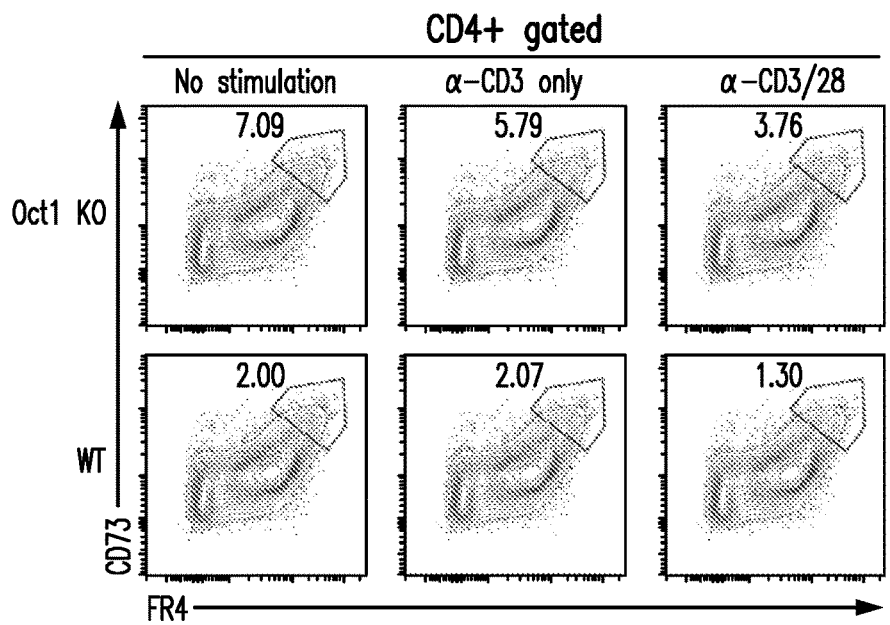
FIG. 13G
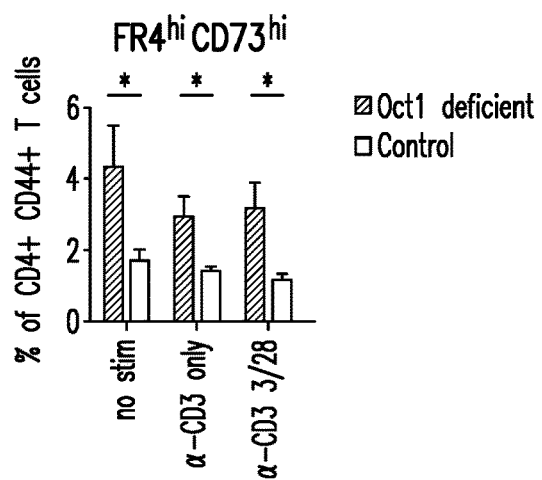
FIG. 13H

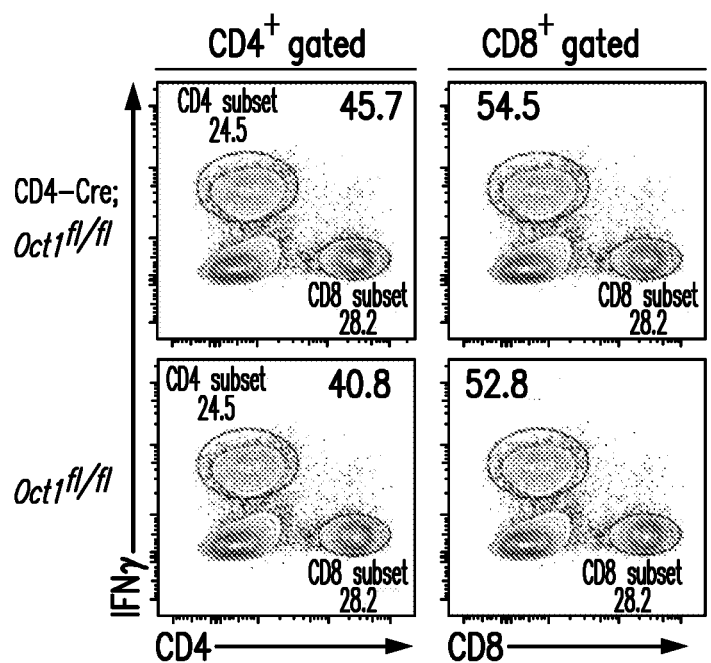
FIG. 15I
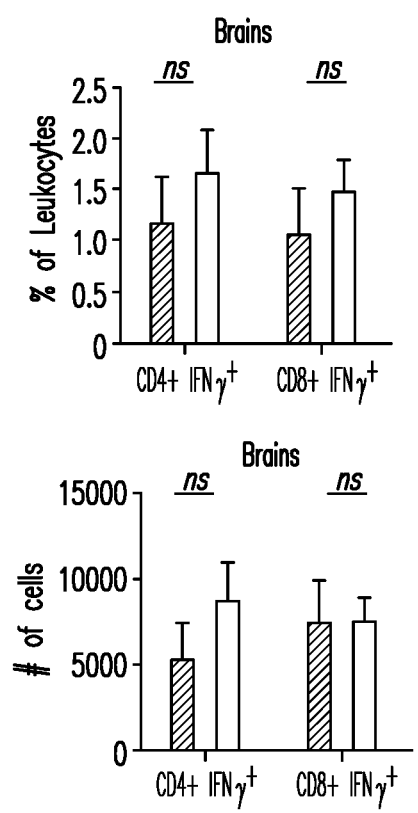
FIG. 15J
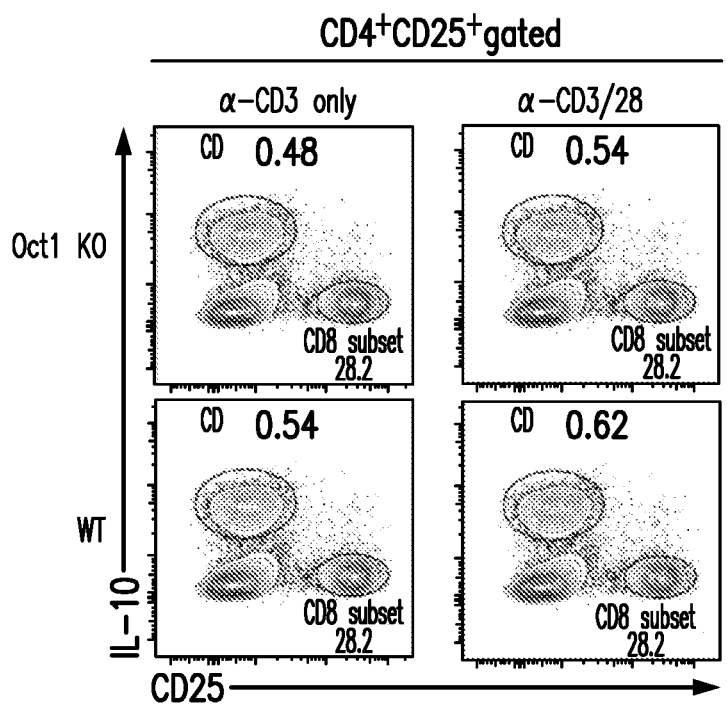
FIG. 16
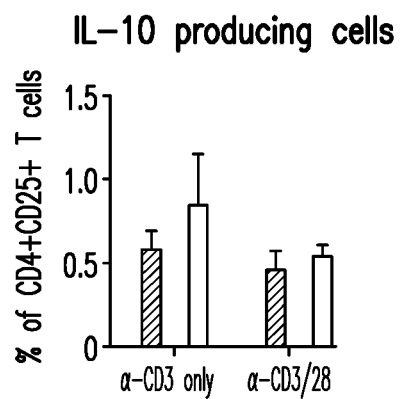

US 12,150,973 B2

OCA-B PEPTIDE CONJUGATES AND METHODS OF TREATMENT

CROSS REFERENCE TO RELATED APPLICATIONS

This application claims the benefit of priority under 35 U.S.C. § 371 of International Application No. PCT/US2019/027987, filed on Apr. 17, 2019, which claims the benefit of the filing date of U.S. Provisional Application No. 62/666,325, which was filed on May 3, 2018. The content of these earlier filed applications is hereby incorporated by reference herein in its entirety.

STATEMENT REGARDING FEDERALLY FUNDED RESEARCH

This invention was made with government support under grant numbers R01NS041249 and R01 AI100873 awarded by the National Institutes of Health. The government has certain rights in the invention.

INCORPORATION OF THE SEQUENCE LISTING

The present application contains a sequence listing that was submitted in ASCII format via EFS-Web concurrent with the filing of the application, containing the file name "21101_0364U2_SL.txt," which is 12,602 bytes in size, created on Sep. 18, 2020, and is herein incorporated by reference in its entirety pursuant to 37 C.F.R. § 1.52 (e) (5).

BACKGROUND

Type 1 Diabetes (T1D) is an autoimmune disease in which the host immune system is directed towards antigens associated with beta cells of the endocrine pancreas. Pathologically, T1D is characterized by insulitis, beta cell destruction and inability to produce insulin. The main treatment for T1D is life-long insulin therapy. Many studies aim to develop new treatments for this disease, but unfortunately the mechanisms of T1D pathogenesis are incompletely understood, limiting the ability to develop new therapies. Alternative approaches are needed for treating T1D.

SUMMARY

Disclosed herein, are compounds comprising a peptide, wherein the peptide is OCA-B or an OCA-B fragment thereof; a linker; and a cell penetrating peptide.

Disclosed herein, are compounds that block the interaction of OCA-B and Jmjd1a, wherein the compounds comprise a peptide consisting of OCA-B or a fragment thereof, SEQ ID NO: 2 or SEQ ID NO: 3; a linker; and a cell penetrating peptide.

Disclosed herein, are methods of treating a subject with a disease, wherein the disease is mitigated by OCA-B repression, the methods comprise administering to the subject a compound comprising a peptide, wherein the peptide is OCA-B or an OCA-B fragment thereof; a linker; and a cell penetrating peptide. Any of the methods of treatment can be configured as methods of "use."

Disclosed herein, are methods of treating a subject with a disease, wherein the disease requires OCA-B repression, the methods comprise administering to the subject a compound comprising a peptide, wherein the peptide is OCA-B or an OCA-B fragment thereof; a linker; and a cell penetrating peptide. Any of the methods of treatment can be configured as methods of "use."

Disclosed herein are compounds comprising a peptide, wherein the peptide is OCA-B or an OCA-B fragment or variant thereof; and a cell penetrating peptide.

Other features and advantages of the present compositions and methods are illustrated in the description below, the drawings, and the claims.

BRIEF DESCRIPTION OF THE DRAWINGS

FIGS. 2A-C shows OCA-B interaction with Jmjd1a. FIG. 2A shows the Oct1/OCA-B/DNA structure (Cepek et al. Genes Dev. 1996 Aug. 15; 10 (16): 2079-88), with specific OCA-B residues highlighted; the Oct1 linker is shown with a dashed line. FIG. 2B shows the top alignment of the OCA-B sequence (SEQ ID NO: 2; hOCA-B) with Oct1 (SEQ ID NO: 33; hOct1) and AR (SEQ ID NO: 34; hAR). FIG. 2C shows a co-immunprecipitation of Jmjd1a with double point-mutant OCA-B. Unlike the control (wild-type OCA-B), the mutant fails to interact, pinpointing this conserved region as a site of interaction with Jmjd1a. HCT116 cells, which lack endogenous OCA-B, were used.

FIG. 3A shows the peptides (peptide #1 (SEQ ID NO: 1), peptide #2 and peptide #3) synthesized as Tat fusions for membrane permeability. Peptides #2 (SEQ ID NO: 2) and #3 (SEQ ID NO: 3) show efficacy. Arrows indicate position of mutant in FIG. 2C. Below: Il2 expression in primary CD4 T cells treated with 25 µM peptide #2 measured by RT-qPCR. FIG. 3B shows the effect of three doses (20 mg/kg) peptide #2 in female NOD mice in which diabetes is newly manifested. In these animals, most pancreatic beta function is lost, and the diabetes arises from autoimmune inflammation (insulitis) in the pancreas, making the remaining beta cells nonfunctional. FIG. 3C shows the percent T cells in the pancreas at endpoint. FIG. 3D shows similar data collected using pancreatic lymph nodes (PLNs).

FIGS. 4A-D shows an unpublished Ocab conditional allele. FIG. 4A shows the targeting event. Crossing with ROSA26-FLP results in the conditional (fl) allele. FIG. 4B shows genotyping of the targeted allele and subsequent recombination events. The founder animal is shown in lane 2. FIG. 4C shows immunoblots from spleens of control, fl/fl and Δ/Δ animals. B-JAB B cell nuclear extract is shown as a positive control for OCA-B expression (lane 1). FIG. 4D shows the effect of crossing the allele to mice expressing Cre recombinase under the control of the T cell-specific CD4 gene (CD4-Cre). Immunoblot of stimulated total T cells is shown.

FIG. 6A shows 8-week female C57BL/6 Oct1fl/fl, CD4-Cre mice were inoculated with MOG peptide, CFA and pertussis toxin and scored for limp tail, hind limb paralysis or quadriplegia.

FIG. 6B shows cervical lymph nodes that were harvested at endpoint from animals with clinical involvement (8 WT and 3 KO). Cells were stimulated with PMA/ionomycin in the presence of brefeldin A. CD4 T cell IL-17a and IFNg were profiled. Representative animals are shown. FIG. 6C shows the quantification of IL-17a/IFNg double-producers.

FIG. 9A shows female NOD animals whose blood glucose was newly-risen above 225 mg/dL were treated with 3 IV/RO peptide injections (10 mg/kg), 12 hr apart. Blood collection occurred prior to $2^{nd}$ injection and 12 hr after final injection. FIG. 9B shows T cells stimulated and rested in culture. Il2 gene expression was measured by TaqMan RT-qPCR. FIG. 9C shows flow cytometry plots of CD4 and CD8 T cells isolated from pancreata. FIGS. 9D and E show similar analysis conducted using pancreatic lymph nodes (PLNs).

FIG. 11A shows a common model of mouse AML leukemogenesis involving the fusion of oncoprotein MLL-AF9. FIG. 11B shows the survival of animals with WT or Ocab$^{-/-}$ BM transduced with MLL-AF9. FIG. 11 C shows peripheral blood smears using representative animals from (B). FIG. 11D shows the genomic PCR of MLL-AF9 in recipient mice, verifying that their donor blood was in fact transduced with the viral oncoprotein.

FIGS. 12A-I the loss of Oct1 in T cells protects mice using an EAE model of MS.

FIG. 12A shows that CD4-Cre; Oct1$^{fl/fl}$ (n=9) or Oct1$^{fl/fl}$ (n=10) mice were injected with MOG$_{35-55}$ peptide and PT to generate EAE. Clinical scores were determined during the post-treatment timecourse. FIG. 12B shows representative luxol fast blue (LFB) staining of thoracic spinal cord sections from animals taken at peak disease (day 21). Areas of demyelination are outlined in dark gray. FIG. 12C show the quantification of demyelination in experimental mice. Mean % demyelination from 6 sections of 2 mice. FIG. 12D shows cervical lymph node lymphocytes that were isolated from EAE-induced CD4-Cre; Oct1$^{fl/fl}$ (n=6) or Oct1$^{fl/fl}$ (n=6) mice and analyzed by flow cytometry. Frequencies of CD4 and CD8 T cells from representative animals are shown. FIG. 12E shows the mean CD4$^+$ and CD8$^+$ T cell percentages (left panel) and total cell numbers (right panel). Cells were independently purified from the cervical lymph nodes (CLNs) of 6 separate mice. FIG. 12F shows representative data showing frequencies of cytokine producing CD4$^+$ cells in the CLN. FIG. 12G shows percentages (left and middle panels) or total cell numbers (right panel) of cytokine producing CD4' T cells are plotted. N=6 for each group. Mean of results is shown. FIG. 12H shows the mean CD4$^+$ and CD8 T cell percentages in the spinal cords. N=3-4 for each group. FIG. 12I shows the cytokine-producing CD4$^+$ T cell percentages (left panel) and total cell numbers (right panel). Cells were independently purified from the spinal cords of 6 separate mice.

FIGS. 13A-H shows that in vitro stimulation of T cells lacking Oct1 results in decreased expression of markers associated with activation and increased expression of markers associated with anergy. FIG. 13A shows Oct1-deficient and control CD4$^+$ T cells were stimulated with indicated antibodies in vitro and analyzed by flow cytometry. Representative frequencies of ICOS-expressing CD4$^+$ CD44$^+$ cells are shown. FIG. 13B shows the quantification of cells independently purified from the spleens of 3 mice, with three technical culture replicates for each mouse. FIG. 13C shows representative flow cytometry plots depicting frequencies of CD25-expressing CD4$^+$ CD44$^+$ cells in Oct1-deficient and control CD4$^+$ T cells. FIG. 13D shows the quantification from 3 animals. FIG. 13E shows the representative expression of CTLA4 in CD4$^+$ CD44$^+$ T cells is plotted as histograms for Oct1-deficient and control CD4$^+$ T cells. FIG. 13F shows CTLA4$^+$ percentages from three animals, with three culture replicates per animal, are plotted. FIG. 13G shows the expression of FR4 and CD73 in Oct1-deficient and control CD4$^+$ CD44$^+$ cells. FIG. 13H shows the averaged percentages of FR4$^{hi}$CD73$^{hi}$CD4$^+$ CD44$^+$ cells plotted.

FIG. 14A shows CD4-Cre; Oct1$^{fl/fl}$ (n=15) or Oct1$^{fl/fl}$ mice (n=14) were infected intracranially (i.c.) with 200 plaque-forming units (PFU) of JHMV and disease severity assessed. Clinical disease was recorded to day 21 post-infection (p.i.). FIG. 14B shows brain viral titers were determined at days 7 and 21 p.i., (n.d., not detected). FIG. 14C shows representative LFB stained thoracic spinal cord sections from experimental mice at day 12 p.i. FIG. 14D shows the quantification of average demyelination from CD4-Cre; Oct1$^{fl/fl}$ (n=4, 12 dpi; n=3, 21 dpi) and Oct1$^{fl/fl}$ mice (n=3, 12 dpi; n=5, 12 dpi) at days 12 and 21 p.i.

FIGS. 15A-J shows normal immune responses in Oct1 T cell-deficient mice during JHMV infection. FIG. 15A shows CD4-Cre; Oct1$^{fl/fl}$ or Oct1$^{fl/fl}$ mice were infected i.c. with 200 PFU of JHMV and sacrificed at days 7 (n=8), 12 (n=4-5) and 21 (n=6) p.i. to assess T cell infiltration into the brain. Representative flow analysis depicting CD4$^+$ T cell infiltration into brains of mice at day 7 p.i. FIG. 15B shows the quantification of CD4$^+$ T cells as shown by calculating both frequencies and numbers of isolated cells. FIG. 15C shows representative flow analysis depicting CD8$^+$ T cell infiltration into brains of mice at day 7 p.i. FIG. 15D shows the quantification of CD8$^+$ T cells as shown by calculating both frequencies and numbers of isolated cells. FIG. 15E shows representative JHMV-specific TCR staining using the M133-147 tetramer of CD4$^+$ T cells from brains of JHMV-infected experimental mice. FIG. 15F shows the quantification of frequency and numbers of M133-147 tetramer CD4$^+$ T cells from cells from experimental groups. FIG. 15G shows representative S510-518 tetramer staining of CD8$^+$ T cells from brains of JHMV-infected experimental mice. FIG. 15H shows quantification of frequency and numbers of M133-147 tetramer CD4+ T cells from cells from experimental groups. Data presented are derived from 2 independent experiments; day 7 p.i., CD4-Cre; Oct1$^{fl/fl}$ n=8, Oct1$^{fl/fl}$ mice n=8; day 12 p.i., CD4-Cre; Oct1$^{fl/fl}$ n=5, Oct1$^{fl/fl}$ mice n=4. (I) IFNγ-producing CD4+ (left panel) and CD8+ (right panel) CNS-infiltrating T cell percentages are shown for representative animals. FIG. 15J shows the averaged frequencies (left panel) and total cell numbers (right panel) of CD4+ and CD8+ cells analyzed as in (B). N=6 for each group.

FIG. 16 shows IL-10 expression is unchanged in Oct1 deficient T cells expressing decreased levels of CD25. Cells were prepared identically to FIG. 13.

DETAILED DESCRIPTION

Figure 1:
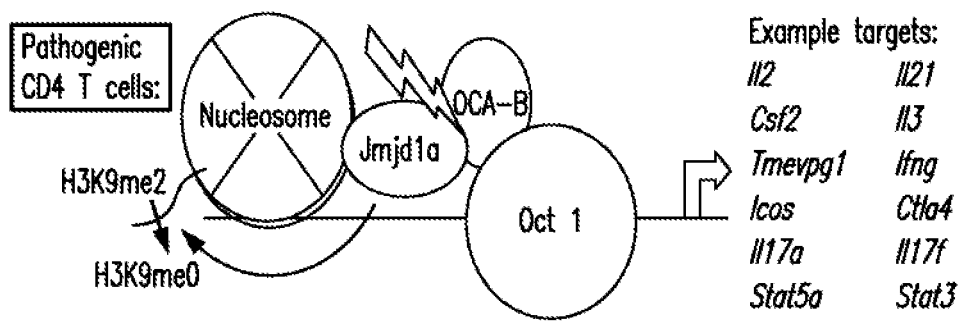
FIG. 1 shows that while other transcription factors (e.g., NF-AT, AP-1) serve as on/off triggers of gene expression, Oct1 and OCA-B maintain silent but previously activated target genes in a readily re-inducible (or "poised") configuration in CD4 T cells. OCA-B "locks" Oct1 in an anti-repressive mode by recruiting Jmjd1a (also known as Kdm3a) to remove inhibitory histone H3K9me2 marks (anti-repression). Recruitment allows for anamnestic rather than naive secondary responses by maintaining target loci in a more permissive chromatin environment. The lightning bolt denotes the new inhibitor, disclosed herein, of the OCA-B/Jmjd1a interaction.

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

OCA-B (also known as OBF-1 and Bob.1, gene symbol Pou2af1) is a transcription coregulator important for B cell antibody switching, and separately for the generation and function of memory T cells. OCA-B is also particularly important for T cells that make pro-inflammatory cytokines. Multiple human GWAS studies implicate OCA-B in T1D pathogenesis (Farth et al. (2015) Nature, 518 (7539): 337-43; and Maurano et al. (2012) Science, 337(6099): 1190-5.

Multiple sclerosis (MS) is a disease with a multifaceted etiology in which the host immune system is directed towards proteins embedded within myelin sheaths in the central nervous system (CNS). Pathologically, MS is characterized by inflammation, demyelination and associated axonopathy. CD4 T cells are clearly implicated in MS pathophysiology. These cells are often found at disease boundaries and can be thought of as master regulators, whereas monocytes and granulocytes migrate deeper into tissues and amplify white matter damage. There are no ideal treatments for MS. For example, IFNβ and steroids have a host of undesirable side effects. While there are no treatments for primary/progressive MS, the most aggressive form of the disease, rituximab is sometimes prescribed off-label for MS. The development of new treatments to block MS development, while keeping normal immune function largely intact, constitutes a major long-term goal in the field, but unfortunately the mechanisms of MS pathogenesis are incompletely understood, limiting the ability to develop new therapies. Targeting pathways involving the transcription coactivator OCA-B may provide a therapeutic avenue to treat MS.

Like MS, T1D is also an autoimmune disease. The main treatment for T1D is life-long insulin therapy. The development of new treatments to block T1D development, while keeping normal immune function largely intact, constitutes a major long-term goal in the field. Regeneration of beta cells is a promising line of therapy, but is unlikely to work unless methods can be developed to specifically block T1D autoimmunity. An even better hypothetical method of therapy would be to capture patients early and block autoimmunity while sparing normal immune function. The findings disclosed herein indicate that targeting OCA-B could provide such a therapeutic avenue. In an aspect, described herein are membrane-permeable peptide OCA-B inhibitors that work in primary cell cultures and in a mouse model of type-1 diabetes.

Disclosed herein is the design and generation of a peptide that mimics the interface between OCA-B and Jmjd1a (gene symbol Kdm3a), a chromatin-modifying enzyme with which it interacts. This peptide was fused to Tat peptide for membrane permeability, generating a reagent with the following sequence: VKELLRRKRGH-GSG(linker)-GRKKRRQRRRGY(Tat) (SEQ ID NO: 10). As described herein, these peptides show strong efficacy in alleviating type-1 diabetes (T1D) symptoms in mice (elevated glucose), and shows that the underlying cause is a reduction in infiltrating T cells in the pancreas, in particularly cells that make pro-inflammatory cytokines. These studies also show that the control result that in the pancreatic lymph nodes, T cell numbers and the ability to make cytokines were unaffected, suggesting that there was no global immune deregulation. These results support that this peptide reduces pathogenic T cell function in type 1 diabetes, while leaving most normal immune function intact.

In an aspect, described herein is a proto-drug (FIG. 1, lightning bolt) developed that is capable of blocking pre-diabetes progression in a mouse non-obese diabetic (NOD) mouse model. The drug's target is the transcriptional co-regulatory protein OCA-B (Bob1/OBF-1, gene symbol Pou2af1), a central component of a new T cell pathway. Loss of OCA-B leaves T cell development and pathogen response intact but impairs the establishment of new memory. T cell memory phenotypes can in turn underlie autoimmunity (including T1D), even in cases of persistent self-antigen exposure. It has been shown that OCA-B directly regulates the expression of important target genes in T cells—among them Il2, Il21, Ifng, Icos and Csf2 (Gmcsf)—but under select circumstances. For example, these genes are unchanged in stimulated OCA-B deficient T cells, but decreased by up to 500-fold upon secondary stimulation—a model of antigen reencounter. Multiple antigen exposures are a central attribute of autoimmune disease. Human GWAS studies pinpoint OCA-B and Oct1, the transcription factor with which it docks, as mediators of T1D risk. As disclosed herein, the overarching hypothesis is therefore that OCA-B coordinately regulates key genes in T cells, encoding cytokines and other immunomodulatory proteins, to promote T1D pathogenesis. This aspect can be tested using a new conditional Ocab (Pou2af1) allele (See e.g., Example 1). The characteristics of a membrane-permeable OCA-B peptide inhibitor that was developed based on the molecular biology of this protein can also be tested (See e.g., Example 2).

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for cancer, such as, for example, prior to the administering step.

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. For example, the disease, disorder, and/or condition can be multiple sclerosis, type 1 diabetes, rheumatoid arthritis, celiac disease, systemic lupus erythematosus, autoimmune thyroiditis, psoriasis, ulcerative colitis or leukemia.

The terms "preventing," "blocking," "antagonizing," or "reversing" mean preventing in whole or in part, or ameliorating or controlling.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

"Cells of the immune system" or "immune cells" or "immune system cells", is meant to include any cells of the immune system that can be targeted or assayed, including, but not limited to, B lymphocytes, also called B cells, T lymphocytes, also called T cells, natural killer (NK) cells, natural killer T (NK) cells, lymphokine-activated killer (LAK) cells, monocytes, macrophages, neutrophils, granulocytes, mast cells, platelets, Langerhan's cells, stem cells, dendritic cells, peripheral blood mononuclear cells, tumor-infiltrating (TIL) cells, gene modified immune cells including hybridomas, drug modified immune cells, antigen presenting cells and derivatives, precursors or progenitors of the above cell types.

A "T cell" or "T lymphocyte" refers to a type of lymphocyte, a type of white blood cell, that is involved in cell-mediated immunity. T cells can be distinguished from other lymphocytes by the presence of a T cell receptor on the cell's surface. Examples of T cell types include but are not limited to T helper cells (e.g., CD4$^+$), cytotoxic killer T cells (e.g., CD8$^+$), memory (e.g., CD4$^+$ or CD8$^+$ and effector T cells, regulatory T cells, natural killer T cells, gamma delta T cells.

The term "fragment" can refer to a portion (e.g., at least 5, 10, 25, 50, 100, 125, 150, 200, 250, 300, 350, 400 or 500, etc. amino acids or nucleic acids) of a peptide that is substantially identical to a reference peptide and retains the biological activity of the reference peptide. In some aspects, the fragment or portion of a peptide retains at least 50%, 75%, 80%, 85%, 90%, 95% or 99% of the biological activity of the reference peptide described herein. A fragment of a referenced peptide can be a continuous or contiguous portion of the referenced polypeptide (e.g., a fragment of a reference peptide that is ten amino acids long can be any 2-9 contiguous residues within that reference peptide).

The term "variant" can refer to a peptide or gene product that displays modifications in sequence and/or functional properties (i.e., altered characteristics) when compared to the wild-type peptide or gene product. In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level. In an aspect, the term "variant" can mean a difference in some way from the reference sequence other than just a simple deletion of an N- and/or C-terminal amino acid residue or residues. In an aspect, a variant can include a substitution of an amino acid residue, the substitution can be considered conservative or non-conservative. Conservative substitutions are those within the following groups: Ser, Thr, and Cys; Leu, lie, and Val; Glu and Asp; Lys and Arg; Phe, Tyr, and Trp; and Gln, Asn, Glu, Asp, and His. Variants can include at least one substitution and/or at least one addition, there may also be at least one deletion. Variants can also include one or more non-naturally occurring residues. For example, they may include selenocysteine (e.g., seleno-L-cysteine) at any position, including in the place of cysteine. Many other "unnatural" amino acid substitutes are known in the art and are available from commercial sources. Examples of non-naturally occurring amino acids include D-amino acids, amino acid residues having an acetylaminomethyl group attached to a sulfur atom of a cysteine, a pegylated amino acid, and omega amino acids of the formula NH2(CH2)nCOOH wherein n is 2-6 neutral, nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties of proline.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. It is understand that the alkyl group is acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

The term "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

Compositions

Disclosed herein are compounds comprising a OCA-B peptide or a fragment thereof; a linker; and a cell penetrating peptide. Also disclosed herein are compounds comprising a OCA-B peptide or an OCA-B peptide fragment or variant thereof; a linker; and a cell penetrating peptide. Also disclosed herein are compounds comprising a OCA-B peptide or an OCA-B peptide fragment or variant thereof; and a cell penetrating peptide. Further disclosed herein are compounds disclosing an OCA-B peptide variant of the OCA-B peptide fragment. In some aspects, the compounds disclosed herein can further comprise a linker. In an aspect, the linker can be a hydrocarbon linker. In an aspect, disclosed herein, are compounds comprising a fragment thereof of an OCA-B peptide; a linker; and a cell penetrating peptide. In an aspect, the compounds described herein can act as OCA-B inhibitors, and are capable of blocking the interaction of OCA-B with Jmjd1a. In an aspect, the compounds described herein can act as OCA-B inhibitors, and are capable of blocking the interaction of OCA-B with Oct1. In an aspect, the compounds described herein are capable of blocking the interaction of OCA-B with Jmjd1a. In an aspect, the compounds described herein are capable of blocking the interaction of OCA-B with Oct1. Also, the compounds disclosed herein can block the interaction of OCA-B and Jmjd1a or Oct1. In an aspect, the compounds disclosed herein comprise a peptide comprising SEQ ID NO: 2 or SEQ ID NO: 3; a linker; and a cell penetrating peptide. In an aspect, the compounds disclosed herein comprise a peptide consisting of SEQ ID NO: 2 or SEQ ID NO: 3; a linker; and a cell penetrating peptide. In an aspect, the compounds disclosed herein comprise a peptide consisting of OCA-B or a fragment thereof, SEQ ID NO: 2 or SEQ ID NO: 3; a linker; and a cell penetrating peptide. In some aspects, any of the compounds disclosed herein can comprise an OC OCA-B peptides, an OCA-B fragment thereof or an OCA-B variant thereof. In an aspect, the peptide can be an OCA-B peptide or an OCA-B fragment thereof. In some aspects, the peptide can be a variant of an OCA-B peptide or an OCA-B fragment. As used herein, a "fragment" refers to a peptide that is less than the full-length sequence of the OCA-B protein (e.g., less than the full-length sequence shown in SEQ ID NOs: 5 or 7). In an aspect, the peptide can be a biologically active variant of an OCA-B peptide or a fragment thereof. Examples of fragments of an OCA-B peptide, include, but are not limited to peptides comprising or consisting of SEQ ID NOs: 1, 2, 3. Examples of an OCA-B peptide includes, but is not limited to a peptide comprising or consisting of SEQ ID NO: 5 or SEQ ID NO: 7. In an aspect, the OCA-B fragment can be SEQ ID NO: 2 or SEQ ID NO: 3. In an aspect, the OCA-B peptide fragment or biologically active variant of an OCA-B peptide can be SEQ ID NO: 2. In an aspect, the OCA-B peptide can be a fragment or biologically active variant of an OCA-B peptide as set forth in SEQ ID NO: 3. Examples of variants of an OCA-B peptide fragment, include, but are not limited to peptides comprising or consisting of SEQ ID NOs: 11, 12, 13, 14, 15, 16, 17, 18, 19, 20, 21, 22, 23, 24, 25, 26, 27, 28, 29, 30, 31, or 32.

In some aspects, the OCA-B peptide or a fragment thereof can be a fragment of any of the OCA-B peptides described herein. In some aspects, the OCA-B fragment can comprise SEQ ID NO: 2 or SEQ ID NO: 3. In an aspect, the OCA-B peptide fragment comprises at least SEQ ID NO: 2. In an aspect, the OCA-B peptides or fragment is not SEQ ID NO: 1.

In some aspects, the OCA-B variant can be a variant of any of the OCA-B peptides described herein. In some aspects, the OCA-B variant can comprise SEQ ID NO: 11, 12, 13, 14, 15, 16, 17, 18, 19, 20, 21, 22, 23, 24, 25, 26, 27, 28, 29, 30, 31, or 32. In an aspect, the OCA-B variant can be a variant of SEQ ID NO: 2 or 3.

Additionally, fragments or variants of any of the OCA-B peptides described herein or known to one of ordinary skill in the art is one that retains biological function of blocking at the interaction of endogenous OCA-B with Jmjd1a or Oct1. A biologically active variant of an OCA-B fragment is capable of blocking the interaction of endogenous OCA-B with Jmjd1a or Oct1. Upon administration to a subject, a biologically active variant or fragment of OCA-B (including variants of OCA-B fragments) can block the interaction of endogenous OCA-B with Jmjd1a or Oct1 with a sufficiently useful affinity. As described herein, a fragment or biologically active variant thereof of OCA-B or OCA-B fragments can be derived from any species. In an aspect, the sequences, or biologically active variants thereof, derived from one species may be identical to those derived from another species. In an aspect, the fragment or biologically active variant of OCA-B or OCA-B fragments can be derived from mouse (SEQ ID NO: 5). In an aspect, the fragment or biologically active variant of OCA-B or OCA-B fragments can be derived from human (SEQ ID NO: 7).

As described herein, a fragment of OCA-B can have about or less than about 256, 250, 240, 230, 220, 210, 200, 190, 180, 170, 160, 150, 140, 130, 120, 110, 100, 90, 80, 70, 60, 50, 40, 30, 25, 20, 19, 18, 17, 16, 15, 14, 13, 12, 11, 10, 9, 8, 7, 6, or 5 amino acid residues. In some aspects, the OCA-B peptide or fragment thereof can be between 3 and 30 amino acid residues.

Where a biologically active fragment of OCA-B is used, the fragment can be at least or about 80% identical (e.g., at least or about, 85%, 90%, 95%, 98%, 99% or 100% identical) to a corresponding wild type fragment of OCA-B. In some aspects, the OCA-B peptide can include a fragment of OCA-B or a biologically active variant thereof that has an amino acid corresponding to SEQ ID NO: 2. In some aspects, the OCA-B peptide can include a fragment of OCA-B or a biologically active variant thereof that has an amino acid corresponding to SEQ ID NO: 3. Where a biologically active fragment of OCA-B is used, the fragment can be at least or about 80% identical (e.g., at least or about, 85%, 90%, 95%, 98%, or 99% identical) to a corresponding fragment of OCA-B disclosed herein. In some aspects, the biologically active fragment of OCA-B can be at least or 5% identical (e.g., at least or about, 10%, 20%, 30%, 40%, 50%, 60%, 70%, 80%, 90%, 95%, 98%, or 99% identical) to a corresponding wild type amino acid sequence of OCA-B.

In an aspect, the OCA-B fragment can have an amino acid sequence of at least 90% (e.g., at least 90%, 95%, 98%, 99% or 100% identical) sequence identity when compared to a wild type fragment of an OCA-B peptide. In an aspect, the wild type fragment of the OCA-B peptide can be derived from a human or a mouse.

The peptides disclosed herein may also include variants. Generally, the amino acid identity between an individual variant of one or more of the OCA-B peptides or fragments disclosed herein can be at least 90%, 91%, 92%, 93%, 94%, 95%, 96%, 97%, 98%, 99%, or 100%. Thus, a "variant OCA-B peptide" is one with the specified identity to the parent or reference OCA-B peptide or fragment thereof of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent or reference OCA-B peptide or fragment thereof. For example, a "variant OCA-B peptide" can be a sequence that contains 1, 2, 3 or 4 amino acid changes as compared to the parent or reference OCA-B peptide or fragment thereof of the invention, and shares or improves biological function, specificity and/or activity of the parent OCA-B peptide or reference OCA-B peptide or fragment thereof.

In an aspect, the OCA-B variant can have an amino acid sequence of at least 90% (e.g., at least 90%, 95%, 98%, 99% or 100% identical) sequence identity when compared to a reference or parent sequence. In an aspect, the reference or parent sequence can be a wild type fragment of an OCA-B peptide. In an aspect, the wild type fragment of the OCA-B peptide can be derived from a human or a mouse.

In some aspects, any of OCA-B peptide variant sequences disclosed herein can include a single amino acid change as compared to the parent or reference OCA-B peptide or fragment thereof. In some aspects, any of the OCA-B peptide variant sequences disclosed herein can include at least two amino acid changes as compared to the parent or reference OCA-B peptide or fragment thereof. In an aspect, the amino acid change can be a change from any amino acid residue to a cysteine residue. In an aspect, the amino acid change can be a change from any amino acid residue to an alanine residue. The amino acid identity between individual OCA-B variants can be at least 60%, 65%, 70%, 75%, 80%, 85%, 90%, 91%, 92%, 93%, 94%, 95%, 96%, 97%, 98%, 99% or 100%. Thus, an "OCA-B peptide variant" can be one with the specified identity to the parent or reference OCA-B peptide or fragment thereof of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent or reference OCA-B peptide or fragment thereof. For example, the parent OCA-B sequence can be one or more of SEQ ID NOs: 5, and/or 7. For example, the reference OCA-B sequence can be one or more of SEQ ID NOs: 1, 2, and/or 3. The variant OCA-B sequence can be at least 60%, 65%, 70%, 75%, 80%, 85%, 90%, 91%, 92%, 93%, 94%, 95%, 96%, 97%, 98%, 99% or 100% identical to any one of SEQ ID NOs: 1, 2, 3, 5 and/or 7. The variant OCA-B sequence can also share at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent or reference OCA-B peptide or fragment thereof.

As discussed herein, there are numerous variants of the OCA-B protein or peptide that are known and herein contemplated. Protein and peptide fragments, variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the peptide sequence. Typically, no more than about from 2 to 6 residues are deleted at any one site within the peptide. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
|---|---|
| alanine | AlaA |
| allosoleucine | AIle |
| arginine | ArgR |
| asparagine | AsnN |
| aspartic acid | AspD |
| cysteine | CysC |
| glutamic acid | GluE |
| glutamine | GlnK |
| glycine | GlyG |
| histidine | HisH |
| isolelucine | IleI |
| leucine | LeuL |
| lysine | LysK |
| phenylalanine | PheF |
| proline | ProP |
| pyroglutamic acidp | Glu |
| serine | SerS |
| threonine | ThrT |
| tyrosine | TyrY |
| tryptophan | TrpW |
| valine | ValV |

TABLE 2

Amino Acid Substitutions

Original Residue Exemplary Conservative Substitutions, others are known in the art.

ala; ser
arg; lys, gln
asn; gln; his
asp; glu
cys; ser
gln; asn, lys
glu; asp
gly; pro
his; asn; gln
ile; leu; val
leu; ile; val
lys; arg; gln;
met; leu; ile
phe; met; leu; tyr
ser; thr
thr; ser
trp; tyr
tyr; trp; phe
val; ile; leu Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g., Arg, are accomplished for example by deleting one of the basic residues or substituting one by glutaminyl or histidyl residues.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

The degree of identity can vary and can be determined by methods well established in the art. "Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. A biologically active variant or a fragment of a peptide or polypeptide described herein can have at least or about 10%, 20%, 30%, 40%, 50%, 60%, 70%, 80%, 90%, 95%, 98%, or 99% identity or homology to a corresponding naturally occurring peptide or polypeptide.

As used herein, the OCA-B fragments can vary in length and can be or can include contiguous amino acid residues that naturally occur in OCA-B or that vary to a certain degree from a naturally occurring OCA-B sequence (but retain a biological activity).

Where the OCA-B peptide or OCA-B fragments include, at their N-terminus or C-terminus (or both), amino acid residues that are not naturally found in OCA-B, the additional sequence(s) can be about 1 to 200 amino acid residues long, and these residues can be divided evenly or unevenly between the N- and C-termini. For example, both the N- and C-termini can include about 1, 10, 20, 30, 40, 50, 60, 70, 80, 90, or 100 amino acid residues. Alternatively, one terminus can include about 1, 10, 20, 30, 40, 50, 60, 70, 80, 90, 100, 110, 120, 130, 140, 150, 160, 170, 180, 190, or 200 residues, and one terminus can include none.

More specifically, the N- or C-termini can include 1 to about 100 (e.g., 1, 2, 3, 4, 5, 6, 7, 8, 9, 10, 15, 20, 25, 30, 40, 50, 60, 70, 80, 90, or 100) amino acid residues that are positively charged (e.g., basic amino acid residues such as arginine, histidine, and/or lysine residues); 1 to about 100 amino acid residues that are negatively charged (e.g., acidic amino acid residues such as aspartic acid or glutamic acid residues); 1 to about 100 glycine residues; 1 to about 100 hydrophobic amino acid residues (e.g., hydrophobic aliphatic residues such as alanine, leucine, isoleucine or valine or hydrophobic aromatic residues such as phenylalanine, tryptophan or tyrosine); or 1 to about 100 (e.g., 1-4) cysteine residues. Where biologically active variants of an OCA-B fragment are used, the variant can vary by substitution of one or more amino acid residues within these groups. The variants can include a conservative amino acid substitution.

The OCA-B and fragments of OCA-B, including the modified fragments described above as well as the OCA-B-variants disclosed herein, can be protease resistant and can include one or more types of protecting groups such as an acyl group, an amide group, a benzyl or benzoyl group, or a polyethylene glycol (PEG).

As noted, the OCA-B, fragments of OCA-B and variants thereof useful in the present compositions can include an amino acid sequence that is identical to a sequence within a naturally occurring OCA-B or they can include a fragment or biologically active variant thereof. These sequences can be modified at, for example, either the amino terminus, the carboxy terminus, or both.

OCA-B and OCA-B fragments and biologically active variants thereof can be modified in numerous ways. For example, agents, including additional amino acid residues, other substituents, and protecting groups can be added to either the amino terminus, the carboxy terminus, or both. The modification can be made for the purpose of altering the fragments' form or altering the way the fragments bind to or interact with other peptides or polypeptides. For example, the fragments can be modified to include cysteine residues or other sulphur-containing residues or agents that can participate in disulphide bond formation. For example, one can add at least one cysteine residue, one of which are, optionally, at the C-terminal or N-terminal of the fragment.

Linkers. The compounds described herein can also comprise one or more linkers. The linkers can be of any length, of a flexible sequence and not have any charges. In an aspect, the linker can be a peptide linker. In an aspect, the one or more linkers can be peptide-based. In an aspect, the one or more linkers can be GSG. In an aspect, the one or more linkers can be non-bulky amino acids. In some aspects, the one or more linkers can be stat AA, AAA, AGA, GGA, AGG, or GAG. In some aspects, the one or more linkers can be used combinatorically with serine.

In some aspects, the linker can be a hydrocarbon linker. In some aspects, the hydrocarbon linker can be an alpha-helix stabilizing moiety. In some aspects, the hydrocarbon linker can be a hydrocarbon staple. In some aspects, the hydrocarbon staple can be in the i, i+3; i, i+4; or i, i+7 configuration. In some aspects, the hydrocarbon stable can have the structure:

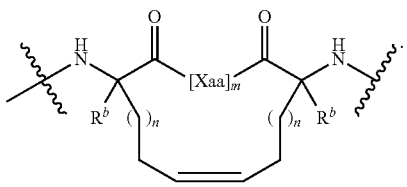

In an aspect, m can be 2, 3, or 6;
n can an integer between 1 and 10, inclusive; $R^b$ is independently H or methyl; and $[Xaa]_m$ can represent 2, 3, or 6 contiguous amino acids of any of the peptides disclosed herein. In some aspects, the hydrocarbon stable can have the structure:

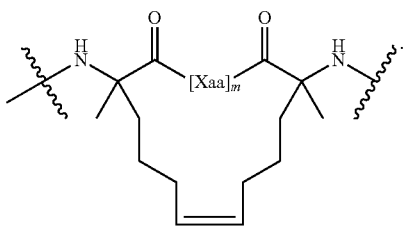

In an aspect, m can be 2, 3, or 6; and $[Xaa]_m$ can represent 2, 3, or 6 contiguous amino acids of any of the peptides disclosed herein.

In some aspects, the linker can be a covalent bond. To form covalent bonds, a chemically reactive group can be used, for instance, that has a wide variety of active carboxyl groups (e.g., esters) where the hydroxyl moiety is physiologically acceptable at the levels required to modify the OCA-B peptide sequence, OCA-B peptide fragment sequence or the cell penetrating peptide sequence.

Any of the peptide sequences described herein and incorporated into the compounds can be modified to chemically interact with, or to include, a linker as described herein. These modified peptide sequences and peptide-linker constructs are within the scope of the present disclosure and can be packaged as a component of a kit with instructions for completing the process of conjugation, for example, to an OCA-B peptide or an OCA-B peptide fragment thereof or an OCA-B variant and/or a cell penetrating peptide. Conjugation refers to the coupling, linking, for example, through a covalent bond, connecting, associating two or more molecules. The peptide sequences can be modified to include a cysteine residue or other thio-bearing moiety (e.g., C—SH) at the N-terminus, C-terminus, or both.

In an aspect, the compounds described herein can comprise a linker between the peptide and the cell penetrating peptide.

Cell penetrating peptide. In an aspect, the cell penetrating peptide can be one that facilitates entry of the peptide or compound into a cell. In an aspect the cell penetrating peptide can be a protein transduction domain from the HIV pTAT protein. In some aspects, the cell penetrating peptide of the compounds disclosed herein can be a TAT sequence. In an aspect, the TAT sequence can be SEQ ID NO: 4. In an aspect, the TAT sequence can be SEQ ID NO: 8. In some aspects, the cell penetrating peptide can be a fragment or derivative of the wild type TAT sequence. In an aspect, the TAT sequence can be 90-100% identical to the wild type TAT sequence.

As described herein, cell penetrating peptides can be of different sizes, amino acid sequences, and charges. Generally, cell penetrating peptides are short peptides that facilitate cellular intake/uptake of "cargo". The "cargo" can be associated with the cell penetrating peptide either through chemical linkage via covalent bonds or through non-covalent interactions. The function of the cell penetrating peptides is to deliver the cargo into cells, a process that commonly occurs through endocytosis. Useful cell penetrating peptides of the instant disclosure will have the ability to translocate the plasma membrane and facilitate the delivery of the compounds disclosed herein to its desired target. Cell penetrating peptides can have an amino acid composition that either contains a high relative abundance of positively charged amino acids such as lysine or arginine or has sequences that contain an alternating pattern of polar/charged amino acids (polycationic) and non-polar, hydrophobic amino acids (amphipathic). A third class of cell penetrating peptides are the hydrophobic peptides, containing polar residues, with low net charge or have hydrophobic amino acid groups that are important for cellular uptake. Examples of cell penetrating peptides can be found in Bechara and Sagan, FEBS Letters, 587 (2013), pp. 1693-1702, which is incorporated herein by reference.

In an aspect, the cell penetrating peptide can be a poly arginine sequence; a peptide sequence that contains about 6 to 12 arginine amino acid residues. In an aspect, the cell penetrating peptide can be SEQ ID NO: 6.

In an aspect, the cell penetrating peptide can be conjugated to the linker via a non-covalent method. In an aspect, the cell penetrating peptide can be Pep-1.

Configurations. Disclosed herein are compounds that comprise a peptide that can be directly conjugated to a linker. Disclosed herein are compounds that comprise a linker that can be directly conjugated to a cell penetrating peptide. Disclosed herein are compounds that comprise a peptide comprising or consisting of SEQ ID NO: 2, a linker that can be GSG, and a cell penetrating peptide that can be SEQ ID NO: 4. Disclosed herein are compounds that comprise SEQ ID NO: 2 directly conjugated to GSG, wherein GSG is also directly conjugated to SEQ ID NO: 4. Disclosed herein are compounds that comprise a peptide comprising or consisting of any of SEQ ID NOs: 10, 11, 12, 13, 14, 15, 16, 17, 18, 19, 20, 21, 22, 23, 24, 25, 26, 27, 28, 29, 30, 31, or 32.

Additionally, hydrocarbon staples exist in one of the following sequences, representative of approximately one or two full helical turns in the peptide: i, i+3; i, i+4; or i, i+7 further limiting the identification of residues suitable to replace with α-methyl, α-alkenyl amino acids. The proposed sequences include residues spaced with the i, i+7 pattern. The rationale is for the staple to cover a larger portion of the peptide, and that by spacing seven residues apart, two full turns of the helix cam be encompassed, thus providing greater stability than either of the i, i+3 or i, i+4 options.

In some aspects, the cell penetrating peptide can be within the hydrocarbon linker. In some aspects, the cell penetrating peptide can serve to stable the alpha helix of the peptide disclosed herein. For example, the composition can comprise an OCA-B variant (e.g., CLLRRKRGC; SEQ ID NO: 36) comprising cysteine residues at both the 5' and 3' ends that form covalent bonds to each other bridged by the cell penetrating peptide.

Cyclized compounds. The compounds disclosed herein can include at least two cysteine residues, one or both of which are, optionally, at the C-terminal or N-terminal of the compound. For example, the compound disclosed herein can include a OCA-B-derived sequence having at or near the C- or N-termini, a cysteine residue, and the cell-penetrating peptide sequence having at or near the C- or N-termini, a cysteine residue. The compound can be cyclized by formation of a disulfide bond between these two cysteine residues (or, more generally, between two of the at least two cysteine residues present at the terminal regions). While the compounds of the present disclosure may be linear or cyclic, cyclic peptides generally have an advantage over linear peptides in that their cyclic structure is more rigid and hence their biological activity may be higher than that of the corresponding linear peptide; and are stable such that lower doses or few administrations (e.g., injections) may be required. Any method for cyclizing peptides can be applied to the compounds described herein.

Stapled compounds. The peptides disclosed herein can be stapled such that the peptide can have a synthetic brace. For the stapled peptides to act as effective therapeutics, it must systemically reach and penetrate its target cell while maintaining an α-helical shape. Peptide stapling can be used to enhance pharmacologic activity of the peptide. In some aspects, combining the cell penetrating peptide within the stabled compound can decrease toxicity of the compounds disclosed herein. In some aspects, the hydrocarbon linker can accommodate the cell penetrating peptide. Without wishing to be bound by theory, it is hypothesized that this strategic enhancement in helicity may improve many of the biophysical and biochemical properties of the molecule, including proteolytic resistance, cell permeabilization, and target affinity. Indeed, because the hydrocarbon staple(s) allows maintenance of the helical shape, it is expected to prohibit the peptide from garnering the extended conformation necessary for proteolytic degradation. In some aspects, a hydrocarbon staple can be used to induce or maintain an α-helical shape of any of the peptides disclosed herein. In an aspect, the hydrocarbon staple can be configured in an i, i+3; i, i+4; or i, i+7 configuration; wherein i can beat any amino acid position from 1-9, 1-8, or 1-4 for the i, i+3; i, i+4; or i, i+7 configuration hydrocarbon staple, respectively, or the corresponding amino acid in an active fragment thereof, of SEQ ID NO:2, wherein i can be at any amino acid position from 1-18, 1-19, or 1-16 for the i, i+3; i, i+4; or i, i+7 configuration hydrocarbon staple, respectively, or the corresponding amino acid in an active fragment thereof, of SEQ ID NO:3; wherein i is at any amino acid position from 1-9, 1-8, or 1-4 for the i, i+3; i, i+4; or i, i+7 configuration hydrocarbon staple, respectively, or the corresponding amino acid in an active variant thereof, of SEQ ID NO:10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, or SEQ ID NO: 32.

Methods of making peptides with a hydrocarbon staple. In one aspect, disclosed are methods of making a peptide comprising at least one hydrocarbon staple pair, the method comprising the step of reacting a peptide comprising at least one hydrocarbon staple precursor pair, as disclosed herein, in the presence of a catalyst for ring-closing olefin metathesis, thereby providing a peptide comprising at least one hydrocarbon staple as disclosed herein.

In a further aspect, the hydrocarbon staple precursor pair of the method can comprises at least one hydrocarbon staple precursor pair in the i, i+3; i, i+4; or i, i+7 configuration; wherein i can be at any amino acid position from 1-9, 1-8, or 1-4 for the i, i+3; i, i+4; or i, i+7 configuration hydrocarbon staple, respectively, or the corresponding amino acid in an active fragment thereof, of SEQ ID NO:2, wherein i can be at any amino acid position from 1-18, 1-19, or 1-16 for the i, i+3; i, i+4; or i, i+7 configuration hydrocarbon staple, respectively, or the corresponding amino acid in an active fragment thereof, of SEQ ID NO:3; wherein i is at any amino acid position from 1-9, 1-8, or 1-4 for the i, i+3; i, i+4; or i, i+7 configuration hydrocarbon staple, respectively, or the corresponding amino acid in an active variant thereof, of SEQ ID NO:10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, or SEQ ID NO: 32; wherein a pair α,α-disubstituted amino acids replace the amino acids at the i, i+3; i, i+4; or i, i+7 of the peptide sequence; and wherein each α,α-disubstituted amino acid is a α-methyl, α-alkenylglycine or α-hydro, α-alkenylglycine residue.

In various aspects, the catalyst for ring-closing olefin metathesis can be a Schrock catalyst or Grubbs' catalyst. In a still further aspect, the catalyst for ring-closing olefin metathesis can be a Grubbs' catalyst.

Without wishing to be bound by theory, modifying this peptide, including reduction of the size and through the addition of a hydrocarbon staple to the backbone, may serve to overcome the current delivery issues.

Addition of a backbone hydrocarbon staple is a relatively new technique used to stabilize α-helical peptides (Schafmeister, C. E., et al. (2000) *J. Am. Chem. Soc.* 122, 5891-5892; Henchey, L. K., et al. (2008) *Curr. Opin. Chem. Biol.* 12, 692-697). Prior to synthesis of the peptide, specific amino acid residues are chosen to undergo modification based on their location in the secondary structure of the peptide. More specifically, these residues must not be involved in interaction with the target, and must exist in the one of the following sequences, representative of approximately 1 or 2 full helical turns in the peptide: i, i+3; i, i+4; or i, i+7 (Schafmeister, C. E., et al. (2000) *J. Am. Chem. Soc.* 122, 5891-5892; Kim, Y. W., et al. (2010) *Org. Lett.* 12, 3046-3049). During synthesis, preferred amino acid residues are replaced with α,α-disubstituted amino acids, which include a stereo-specific alkyl chain of arbitrary length instead of a hydrogen atom at the a position (Bird, G. H., et al. (2008) *Methods Enzymol.* 446, 369-386). Once the sequence has been synthesized, the alkyl chains are connected using a ruthenium-catalyzed ring-closing olefin metathesis, thus creating the hydrocarbon staple (Scheme 1) (Kim, Y. W., et al. (2011) *Nat. Protoc.* 6, 761-771).

Without wishing to be bound by theory, adding this staple locks the peptide in its α-helical state, thereby limiting the number of attainable conformations in solution. This may result in an increase in percent helicity of the peptide and contribute to a vast improvement in the potency of the therapeutic. Locking the peptide in an α-helical state is primarily responsible for the increase in proteolytic resistance seen with stapled peptides, as proteases are known to bind their substrates in an extended, non-helical conformation (Verdine, G. L. and G. J. Hilinski, (2012) *Methods Enzymol.* 503, 3-33). Thus, by preventing the formation of an extended conformation, stapled peptides show stronger resistance to proteolytic degradation than non-modified peptides. In addition, with a peptide existing in this α-helical state, the polar amide backbone is buried internally due to the intramolecular hydrogen bonding characteristic to helix formation (Verdine, G. L. and G. J. Hilinski, (2012) *Methods Enzymol.* 503, 3-33). Without wishing to be bound by theory, this concealment of hydrophilicity may increase the exposure of hydrophobic residues, adding to an increase in cell membrane permeation. For example, once internalized, a 5-5000-fold increase in target affinity can result due to the vast reduction in the entropic cost of target binding caused by the pre-organized, locked peptide state (Verdine, G. L. and G. J. Hilinski, (2012) *Methods Enzymol.* 503, 3-33; Schafmeister, C. E., et al. (2000) *J. Am. Chem. Soc.* 122, 5891-5892; Bird, G. H., et al. (2010) *Proc. Nat. Acad. Sci. U.S.A* 107, 14093-14098). Overall, the increases in proteolytic resistance, cell internalization, and enhanced target affinity may result in drastic improvements of the in vitro and in vivo efficacy of the peptide therapeutic. Without wishing to be bound by theory, in various aspects these enhancements could be multiplied even further by adding a second hydrocarbon staple to the backbone of larger peptides (Bird, G. H., et al. (2010) *Proc. Nat. Acad. Sci. U.S.A* 107, 14093-14098).

PEGylation. In some aspects, the compounds disclosed herein can be PEGylated. PEGylation is a process of attaching the strands of the polymer PEG (polyethylene glycol) to molecules, including peptides. Said PEGylation can improve the safety and efficiency of the peptide. More specifically, PEGylation is the process of both covalent and non-covalent attachment or amalgamation of polyethylene glycol polymer chains to molecules and macrostructures, such as a drug, therapeutic protein or vesicles. PEGylation is routinely achieved by the incubation of a reactive derivative of PEG with the molecule. The covalent attachment of PEG to a drug or therapeutic protein can "mask" the agent from the host's immune system thereby reducing immunogenicity and antigenicity, and increasing the hydrodynamic size (size in solution) of the agent which prolongs its circulatory time by reducing renal clearance. PEGylation can also provide water solubility to hydrophobic drugs and proteins.

Sequences. Sequences are shown in Table 3.

TABLE 3

Sequences.

| SEQ ID NO: | Sequence | Name |
| --- | --- | --- |
| 1 | ARPYQGVRVKEPVK | Peptide #1 |
| 2 | VKELLRRKRGH | Peptide #2; OCA-B Wildtype |
| 3 | ARPYQGVRVKEPVKELLRRKRGH | Peptide #3 |
| 4 | GRKKRRQRRRGY | TAT |
| 5 | MLWQKSTAPEQAPAPPRPYQGVRVKEPVKELLRRKRGHTSVGAAG PPTAVVLPHQPLATYSTVGPSCLDMEVSASTVTEEGTLCAGWLSQ PAPATLQPLAPWTPYTEYVSHEAVSCPYSTDMYVQPVCPSYTVVG PSSVLTYASPPLITNVTPRSTATPAVGPQLEGPEHQAPLTYFPWP QPLSTLPTSSLQYQPPAPTLSGPQFVQLPISIPEPVLQDMDDPRR AISSLTIDKLLLEEEESNTYELNHTLSVEGF | OCA-B; mouse |
| 6 | RQIKIWFQNRRMKWKK | Penetratin |
| 7 | MLWQKPTAPEQAPAPARPYQGVRVKEPVKELLRRKRGHASSGAAP APTAVVLPHQPLATYTTVGPSCLDMEGSVSAVTEEAALCAGWLSQ PTPATLQPLAPWTPYTEYVPHEAVSCPYSADMYVQPVCPSYTVVG PSSVLTYASPPLITNVTTRSSATPAVGPPLEGPEHQAPLTYFPWP QPLSTLPTSTLQYQPPAPALPGPQFVQLPISIPEPVLQDMEDPRR AASSLTIDKLLLEEEDSDAYALNHTLSVEGF | OCA-B; human |
| 8 | GRKKRRQRRRPPQ | TAT |
| 9 | EPVKEPVKKELLRRKRGHSVGAAGPP | Peptide#4 |
| 10 | VKELLRRKRGHGSGGRKKRRQRRRGY | OCA-B fragment |
| 11 | AKELLRRKRGH | OCA-B variant |
| 12 | VAELLRRKRGH | OCA-B variant |
| 13 | VKALLRRKRGH | OCA-B variant |
| 14 | VKEALRRKRGH | OCA-B variant |
| 15 | VKELARRKRGH | OCA-B variant |
| 16 | VKELLARKRGH | OCA-B variant |

TABLE 3-continued

Sequences.

| SEQ ID NO: | Sequence | Name |
|---|---|---|
| 17 | VKELLRAKRGH | OCA-B variant |
| 18 | VKELLRRARGH | OCA-B variant |
| 19 | VKELLRRKAGH | OCA-B variant |
| 20 | VKELLRRKRAH | OCA-B variant |
| 21 | VKELLRRKRGA | OCA-B variant |
| 22 | CKELLRRKRGH | OCA-B variant |
| 23 | VCELLRRKRGH | OCA-B variant |
| 24 | VKCLLRRKRGH | OCA-B variant |
| 25 | VKECLRRKRGH | OCA-B variant |
| 26 | VKELCRRKRGH | OCA-B variant |
| 27 | VKELLCRKRGH | OCA-B variant |
| 28 | VKELLRCKRGH | OCA-B variant |
| 29 | VKELLRRCRGH | OCA-B variant |
| 30 | VKELLRRKCGH | OCA-B variant |
| 31 | VKELLRRKRCH | OCA-B variant |
| 32 | VKELLRRKRGC | OCA-B variant |

Pharmaceutical Compositions

As disclosed herein, are pharmaceutical compositions, comprising the compounds described above and a pharmaceutical acceptable carrier. In some aspects, the pharmaceutical composition can be formulated for intravenous administration. The compositions of the present disclosure also contain a therapeutically effective amount of a compound as described herein. The compounds can comprise a peptide, wherein the peptide is OCA-B or an OCA-B fragment thereof, a linker; and a cell penetrating peptide. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used to deliver the bi-functional allosteric protein-drug molecules. Thus, compositions can be prepared for parenteral administration that includes bi-functional allosteric protein-drug molecules dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

Methods of Treatment

Disclosed herein, are methods of treating a subject with a disease with one or more of the compounds described herein. In an aspect, the treatment of the disease can require repression of OCA-B or blockage of the interaction between OCA-B with Jmjd1a and/or Oct1. In an aspect, the method can comprise identifying a patient in need of treatment. In an aspect, the method can comprise administering to the subject a therapeutically effective amount of a pharmaceutical composition (or compound) as disclosed herein. In an aspect, the method can comprise administering to the subject a therapeutically effective amount of a pharmaceutical composition (or compound) comprising a compound a peptide, wherein the peptide is OCA-B or an OCA-B fragment thereof or an OCA-B variant; a linker; and a cell penetrating peptide, and a pharmaceutically acceptable carrier or excipient. In an aspect, the method can comprise administering to the subject a therapeutically effective amount of a pharmaceutical composition (or compound) comprising a compound a peptide, wherein the peptide is OCA-B or an OCA-B fragment thereof or an OCA-B variant; and a cell penetrating peptide, and a pharmaceutically acceptable carrier or excipient.

Disclosed herein, are methods of inhibiting OCA-B in a mammalian cell. In an aspect, the methods can comprise treating the cell with any of the compounds described herein. In an aspect, the methods can comprise treating the cell with a therapeutically effective amount of the pharmaceutical composition comprising a compound a peptide, wherein the peptide is OCA-B or an OCA-B fragment thereof or an OCA-B variant; a linker; and a cell penetrating peptide, and a pharmaceutically acceptable carrier. In an aspect, the methods can comprise treating the cell with a therapeutically effective amount of the pharmaceutical composition comprising a compound a peptide, wherein the peptide is OCA-B or an OCA-B fragment thereof or an OCA-B variant; and a cell penetrating peptide, and a pharmaceutically acceptable carrier. In an aspect, the cell can be an immune system cell. In an aspect, the immune system cell can be a T cell.

The pharmaceutical compositions described above can be formulated to include a therapeutically effective amount of the compounds disclosed herein. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to a type of autoimmune disease (including multiple sclerosis, type 1 diabetes, rheumatoid arthritis, celiac disease, systemic lupus erythematosus, autoimmune thyroiditis, psoriasis, ulcerative colitis or leukemia).

The pharmaceutical compositions described herein can be administered to the subject (e.g., a human patient) in an amount sufficient to delay, reduce, or preferably prevent the onset of clinical disease. Accordingly, in some aspects, the patient can be a human subject or patient. In therapeutic applications, compositions can be administered to a subject (e.g., a human patient) already with or diagnosed with a disease (e.g., type 1 diabetes, multiple sclerosis, rheumatoid arthritis, celiac disease, systemic lupus erythematosus, autoimmune thyroiditis, psoriasis, ulcerative colitis or leukemia) in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a pharmaceutical composition can be an amount that achieves a cure, but that outcome is only one among several that can be achieved. As noted, a therapeutically effect amount includes amounts that provide a treatment in which the onset or progression of the disease is delayed, hindered, or prevented, or the disease or a symptom of the disease is ameliorated. One or more of the symptoms can be less severe. Recovery can be accelerated in an individual who has been treated.

In some aspects, the disease can be type 1 diabetes, multiple sclerosis, rheumatoid arthritis, celiac disease, systemic lupus erythematosus, autoimmune thyroiditis, psoriasis, ulcerative colitis or leukemia. In some aspects, the disease is associated with a need to repress, block or inhibit OCA-B, for example, endogenous OCA-B.

Disclosed herein, are methods of treating a patient with type 1 diabetes, multiple sclerosis, rheumatoid arthritis, celiac disease, systemic lupus erythematosus, autoimmune thyroiditis, psoriasis, ulcerative colitis or leukemia. In some aspects, the methods can include the step of determining a subject in need of treatment or a need to repress OCA-B.

Figure 3A:
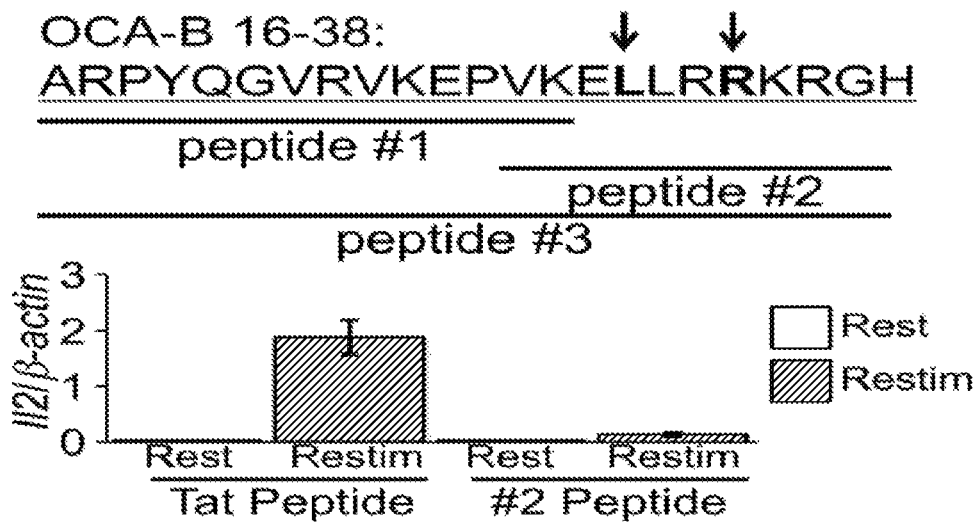
FIGS. 3A-D show OCA-B inhibitors and results using these peptides in primary CD4 T cells and in a NOD mouse model.

Disclosed herein are methods that can be carried out to determine the efficacy of one or more peptides for their ability to block the interaction of OCA-B and Jmjd1a or Oct1. In some aspects, the method can be, for low-throughput studies, treating primary human or mouse CD4 T cells that have been previously stimulated and rested in culture with the test peptide (10-50 µM), and re-stimulating cells with CD3/CD28 antibodies in the presence of inhibitor. Efficacy can be determined by suppression of e.g., Il2 gene expression in T cells receiving a second stimulation, phenocopying the OCA-B germline deficient mouse (as shown in FIG. 3A). In some aspects, high throughput assays can be run, for example, using inhibition of luciferase reporter gene expression, e.g., using a synthetic or immunoglobulin promoter driving expression of the reporter from a transiently transfected or stably integrated plasmid in virtually any cell line. Another cell-free example can be inhibition of co-immunoprecipitation.

Amounts effective for this use can depend on the severity of the disease and the weight and general state and health of the subject. Suitable regimes for initial administration and booster administrations are typified by an initial administration followed by repeated doses at one or more hourly, daily, weekly, or monthly intervals by a subsequent administration. For therapeutic uses, the compounds can include a pharmaceutically acceptable excipient. Such compositions can be formulated without undue experimentation for administration to a mammal, including humans, as appropriate for the particular application. Additionally, proper dosages of the compositions can be determined without undue experimentation using standard dose-response protocols. For example, a subject can receive any of the compound or compositions disclosed herein one or more times per week (e.g., 2, 3, 4, 5, 6, or 7 or more times per week).

The total effective amount of any of compounds in the pharmaceutical compositions disclosed herein can be administered to a mammal as a single dose, either as a bolus or by infusion over a relatively short period of time, or can be administered using a fractionated treatment protocol in which multiple doses are administered over a more prolonged period of time (e.g., a dose every 4-6, 8-12, 14-16, or 18-24 hours, or every 2-4 days, 1-2 weeks, or once a month). Alternatively, continuous intravenous infusions sufficient to maintain therapeutically effective concentrations in the blood are also within the scope of the present disclosure.

The therapeutically effective amount of any of the compounds disclosed herein present within the pharmaceutical compositions described herein and used in the methods as disclosed herein applied to mammals (e.g., humans) can be determined by one of ordinary skill in the art with consideration of individual differences in age, weight, and other general conditions (as mentioned above).

EXAMPLES

Example 1: OCA-B in T Cells Promotes T1D in Genetic Mouse Models

To determine if OCA-B loss in T cells confers T1D protection, a Ocab (Pou2af1) conditional mouse allele can be used. Backcrossing the OCA-B allele to the NOD strain background (which is prone to spontaneous T1D) was completed. Next, this animal can be crossed to NOD/CD4-Cre. These mice can undergo a complete set of tests to measure T1D susceptibility and severity.

OCA-B is so named for its strong expression in the B cell lineage, where it is required after B cell activation to generate high-affinity antibodies. Interestingly, antibody-secreting cells themselves do not express OCA-B, indicating that OCA-B controls formation but not maintenance of long-lived antibody-secreting cells. OCA-B inhibition would therefore leave neutralizing immunity mediated by long-lived antibody-secreting cells unaffected. A functional role for OCA-B in CD4 helper T cells was identified: T cells lacking OCA-B develop normally and mount normal pathogen responses, but fail to form central memory CD4 cells in appreciable numbers. The cells that are formed are defective in their response to antigen re-encounter. The level of OCA-B in T cells is at least 50-fold less than in B cells, suggesting that carefully tuned doses of a competitive inhibitor will result in T cell-selective effects. The underlying molecular mechanism by which OCA-B promotes target gene expression upon antigen re-encounter is as follows: the transcription factor Oct1 binds to regulatory regions in a large group of immuno-modulatory genes in T cells. In the absence of OCA-B, Oct1 responds to signals to either potentiate or inhibit gene expression. When OCA-B becomes expressed in activated CD4 T cells, it "locks in" Oct1's ability to potentiate gene expression by acting as a bridge between Oct1 and Jmjd1a/Kdm3a, a histone lysine demethylase that removes inhibitory histone H3K9me2 chromatin modifications. The normal T cell developmental and primary immune response phenotypes observed in the absence of OCA-B help form the basis of a potential "therapeutic index" for T1D patients in which targeting OCA-B leaves baseline immune function only minimally affected. An epigenetic model predicts that, as in antibody secretion in B cells, OCA-B will be dispensable in CD4 memory T cells once they are formed.

Evidence for a role for OCA-B in T1D: OCA-B levels vary in different T cell populations. OCA-B is undetectable in naïve CD4 T cells, but expressed after sustained antigen stimulation. As expected, OCA-B levels are elevated in CD4 central memory cells relative to other T cell populations (not shown), but interestingly the highest expression in profiled cells is found in pancreas-infiltrating, auto-reactive CD4 T cells (ImmGen (http://immgen.org)); shows Ocab (Pou2af1) expression in u CD4 T cell subsets). Human polymorphisms have been identified that affect binding sites for Oct1, the transcription factor with which OCA-B docks, in the Tnfa and Ctla4 loci. These polymorphisms are associated with IBD and SLE, respectively, suggesting a general role for OCA-B in autoimmune etiology. Additionally, Oct1 binding site polymorphisms are directly implicated in human T1D pathogenesis. Of the transcription factors identified in this study (Maurano et al. Science. 2012 Sep. 7; 337(6099): 1190-5), Oct1 (Pou2fl) is among the most potent, and the strongest disease associated with Oct1 is T1D. Other associations in this study are with celiac disease and rheumatoid arthritis. A second study (Farh, et al., Nature. 2015 Feb. 19; 518(7539): 337-43) associates other Oct1 binding site polymorphisms with multiple sclerosis, autoimmune thyroiditis, celiac disease, psoriasis and ulcerative colitis.

Three injections of a peptide that blocks the interaction of OCA-B with Jmjd1a, a chromatin regulator with which it interacts to promote transcription, reduces blood glucose and T cell infiltration in a NOD mouse model. Animals treated with control peptide by contrast progress. Long-term treatment with this agent can be determined and whether said treatment with this agent can afford sustained protection and results in any immunological or toxic side effects can also be determined. The durability of the effects can be determined by removing the inhibitor and monitoring T1D progression. Finally, the effects in animals with fully-established disease can also be determined, with the expectation that no improvement without beta cell replacement will be observed.

Figure 2A:
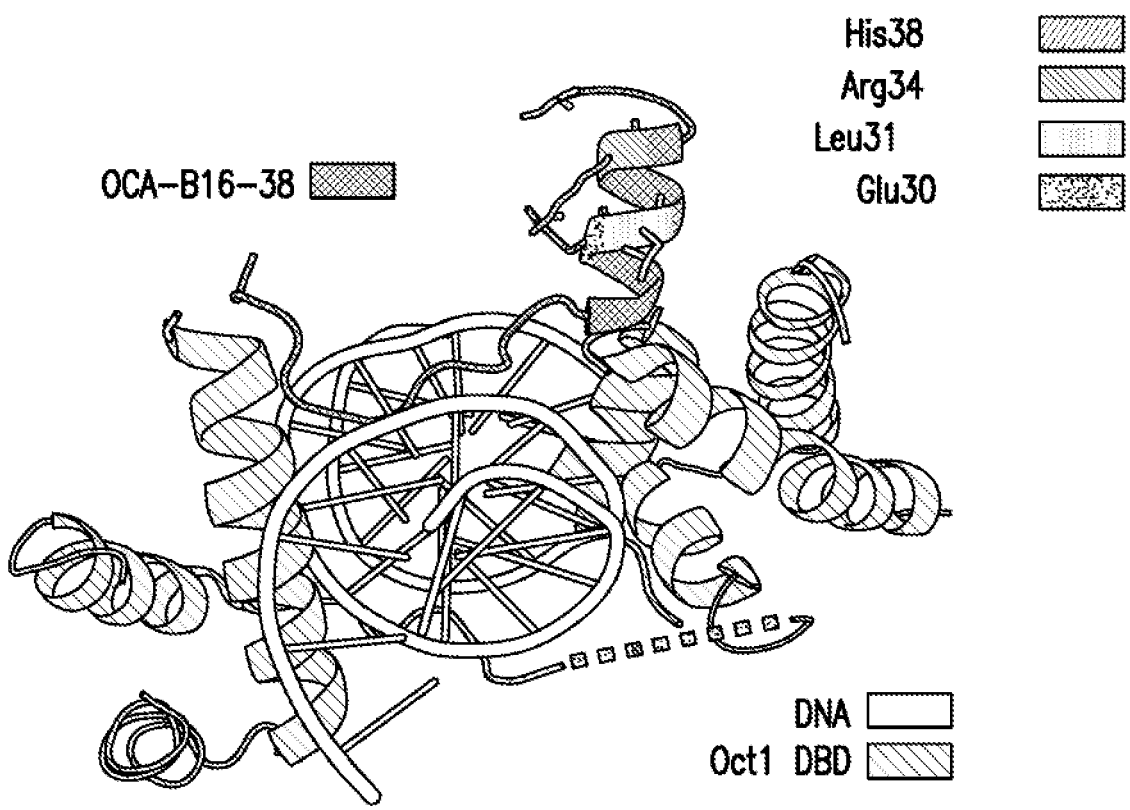
Figure 2B:
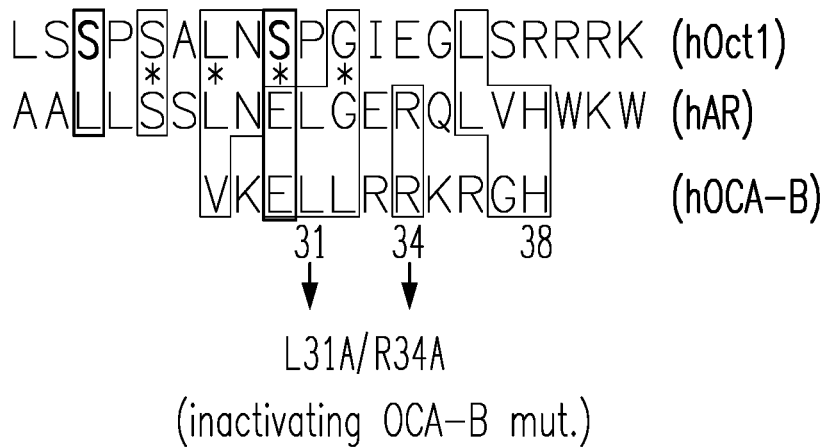

Pharmacological OCA-B inhibition blocks T1D progression. In the presence of active MEK/ERK signals, Oct1 can interact with Jmjd1a in the absence of OCA-B. Oct1 contains two consensus ERK phospho-acceptor serines. The co-crystal structure of the Oct1 DNA-binding domain, OCA-B N-terminus and consensus binding DNA (Chasman et al. Genes Dev. (1999) 13(2): 2650-7) reveals that these Oct1 serines are located in a flexible, solvent-exposed loop (the linker domain), which connects the two DNA binding sub-domains (FIG. 2A, red dashed line). FIG. 2 shows the alignments to androgen receptor, a known recruiter of Jmjd1a, and identifies an OCA-B interaction surface. The crystalized region of OCA-B is known to include regions important for Oct1 binding and transcription activity. In contrast with Oct1, OCA-B constitutively interacts with Jmjd1a. To identify potential Jmjd1a-interacting amino acids, the full-length Oct1 and OCA-B amino acid sequences were aligned to androgen receptor (AR), another transcription factor known to interact with Jmjd1a. Human AR mutations that cause androgen insensitivity have been mapped to the cofactor interaction surface spanning residues 698-721. FIG. 2B shows Oct1/OCA-B alignment with AR cofactor interaction region; asterisks indicate AR mutations causing androgen insensitivity; and boxed serines show predicted ERK sites. This sequence aligns with the Oct1 linker domain (FIG. 2B), implicating the linker as a potential Jmjd1a-interacting surface. The alignment shows conservation of 3 out of 4 AR mutation sites with Oct1. The AR mutation site that is not conserved is a glutamic acid residue, a potential phospho-mimetic, and in Oct1 is a consensus ERK target (Ser370). These findings suggest that the Oct1 linker domain constitutes a surface which, when phosphorylated by ERK, interacts with Jmjd1a. Oct1 mutational analysis corroborates this assumption.

Figure 2C:
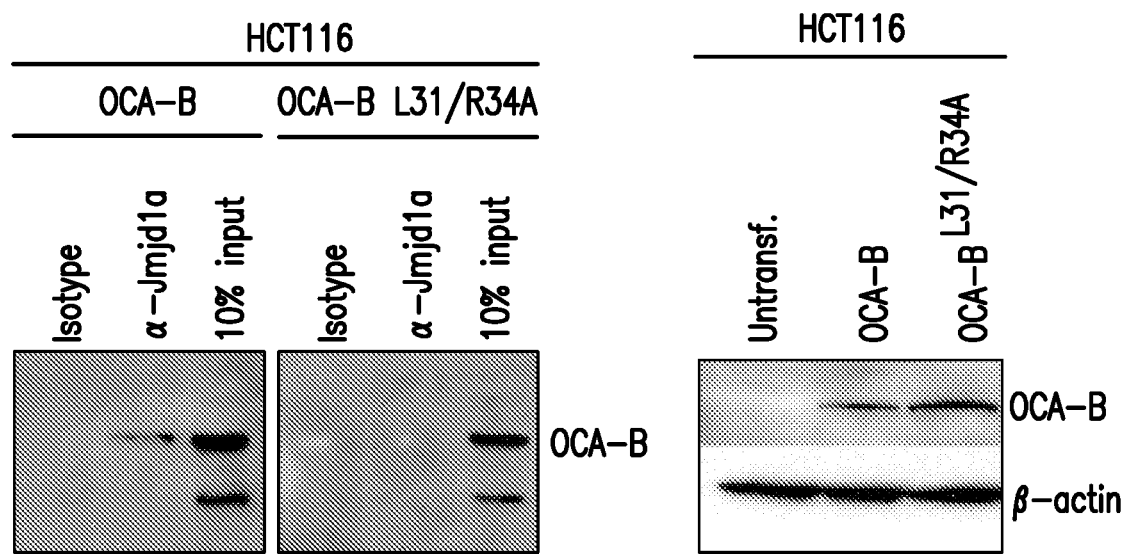

As with Oct1, alignment with OCA-B identifies a potential Jmjd1a interacting surface (FIG. 2B). Unlike Oct1, an OCA-B glutamic acid residue (Glu30) aligns with AR, consistent with the finding that OCA-B interacts with Jmjd1a in the absence of ERK signaling. Interestingly, the residues aligning to AR lie on one side of a solvent-exposed helix (FIG. 2A). Glu30 (red), Leu31 (yellow), Arg34 (blue) and His38 (blue) may therefore constitute a Jmjd1a docking surface. These residues are conserved in humans. Different point mutants in an OCA-B transient expression plasmid were generated. Control co-IP using Jmjd1a antibodies and wild-type OCA-B identify an interaction (FIG. 2C, left). One mutant protein, for example, L31A/R34A, still interacted with Oct1 (not shown), but failed to interact with Jmjd1a (FIG. 2C, left). The mutant was expressed equivalently to WT in HCT116 cells (FIG. 2C, right). The two proteins were expressed equivalently (FIG. 2C, far right).

The Jmjd1a interaction surface of OCA-B (FIG. 4) reveals an opportunity to target OCA-B pharmacologically. Peptides were designed overlapping the OCA-B surface responsible for Jmjd1a binding, and were synthesized as Tat-fusions for membrane permeability (FIG. 3A). Of the tested peptides, 25 µM peptide #2 or #3 phenocopies the OCA-B null phenotype, revealing selective 12 and Ifng expression defects following CD4 T cell restimulation (FIG. 3A and not shown; also see, FIG. 9). Treated cells show no changes in viability, morphology or expansion (not shown). Peptide #2 was used for subsequent experiments.

Figure 3B:
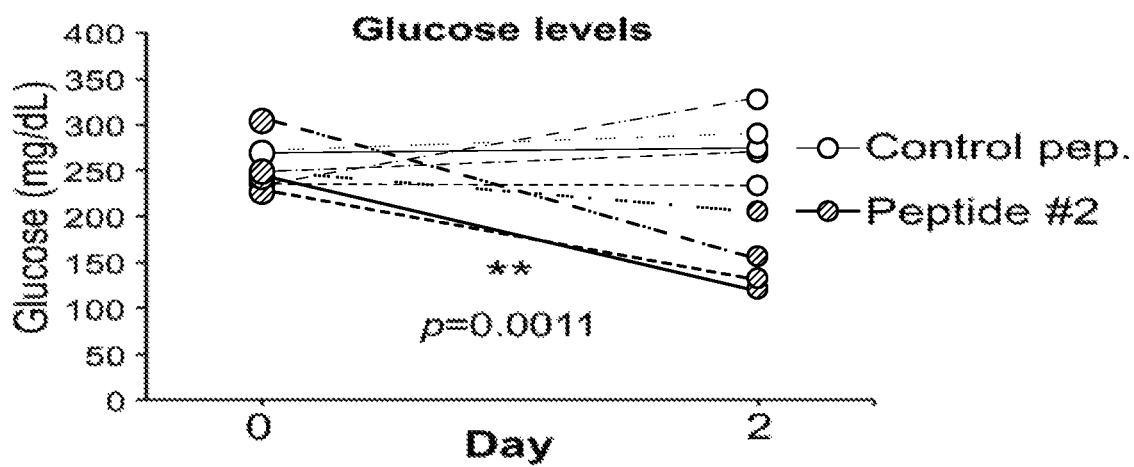
Figure 3C:
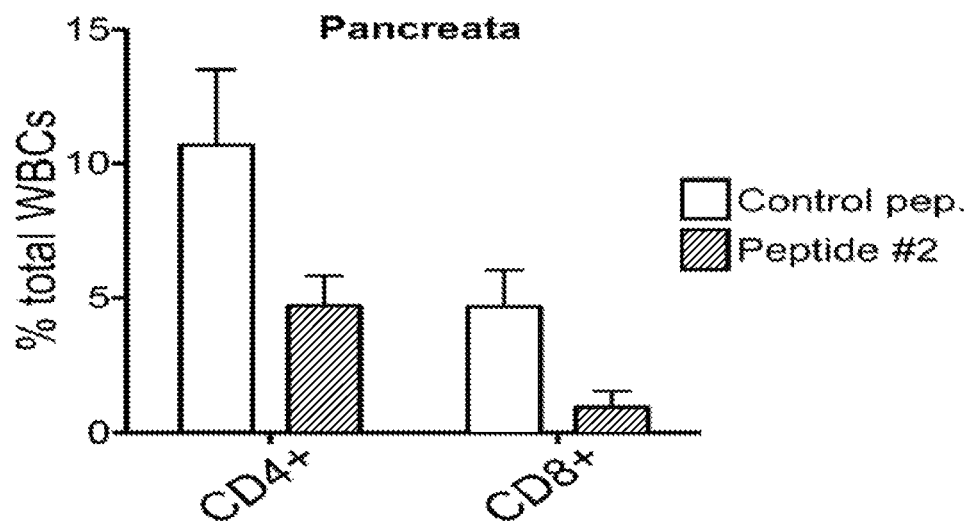
Figure 3D:
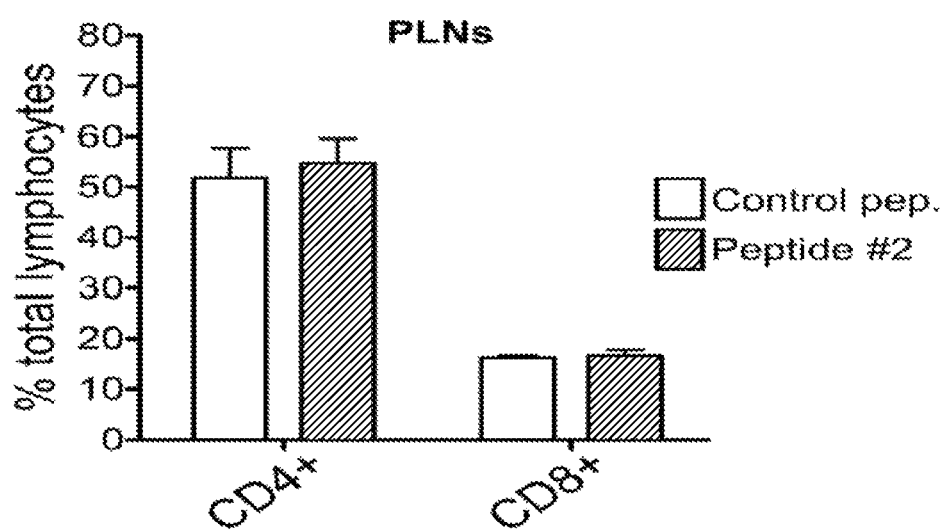

The peptide was synthesized and purified for an in vivo experiment. T1D onset in NOD mice is spontaneous and acute, allowing the administration of the peptide as symptoms arise. Female 14-18 week-old NOD mice whose glucose levels were newly-risen above 225 mg/dL but were still below 275 mg/dL were treated with three intravenous injections of 20 mg/kg peptide or Tat-only peptide control. The peptide half-life in serum was predicted to be ~5 hr, and therefore the injections were spaced by 12 hr. Twelve hours after the final injection, blood glucose was collected and flow cytometry performed on the pancreas and pancreatic lymph nodes (PLNs). Strikingly, the inhibitor reversed elevated blood glucose (FIG. 3B; also see, FIG. 9), pancreatic T cell infiltration (both total numbers and percentages, FIG. 3C and not shown; also see, FIG. 9) and pro-inflammatory IFNγ and IL-17A cytokine production (not shown). Control peptide at the same concentration had no effect. In contrast to the pancreas, PLNs showed no change in T cell numbers or percentages (FIG. 3D and not shown; also see, FIG. 9) and smaller changes in pro-inflammatory cytokine production, suggesting that baseline immune responses were unimpaired. OCA-B levels in B cells are at least 50-fold higher than in T cells (Immgen), making it likely that the observed effects are due to competitive inhibition in T cells. These data provide evidence that the peptide is nontoxic and efficacious in vivo, offering a valid strategy to treat emerging T1D. This peptide was used as a proto-drug to assess function and possible side effects.

Figure 4C:
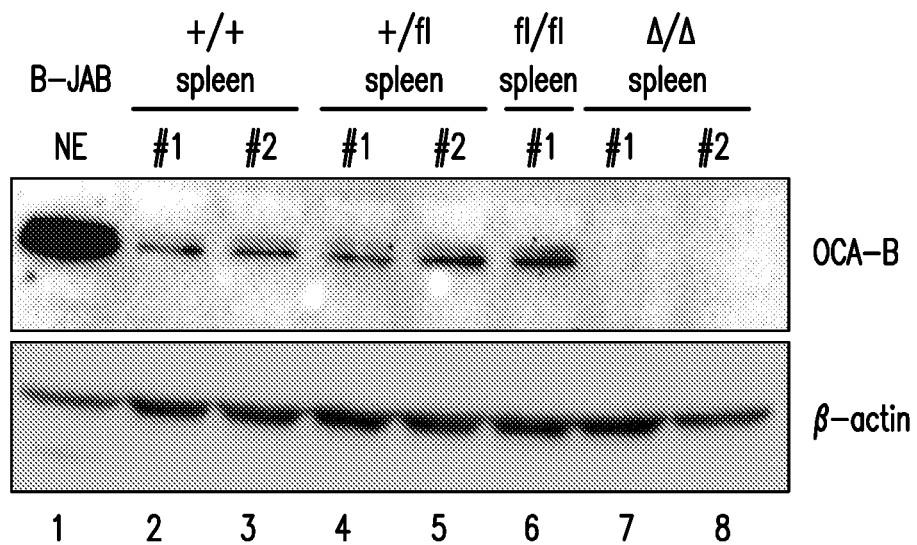
Figure 4D:
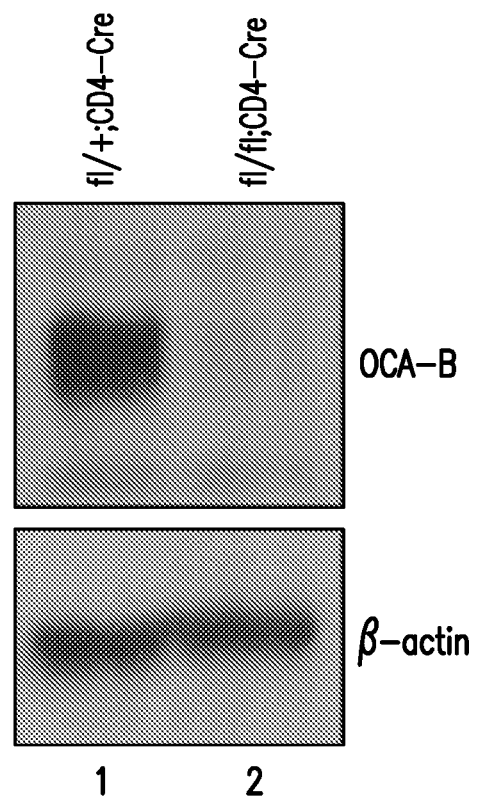
Figure 5:
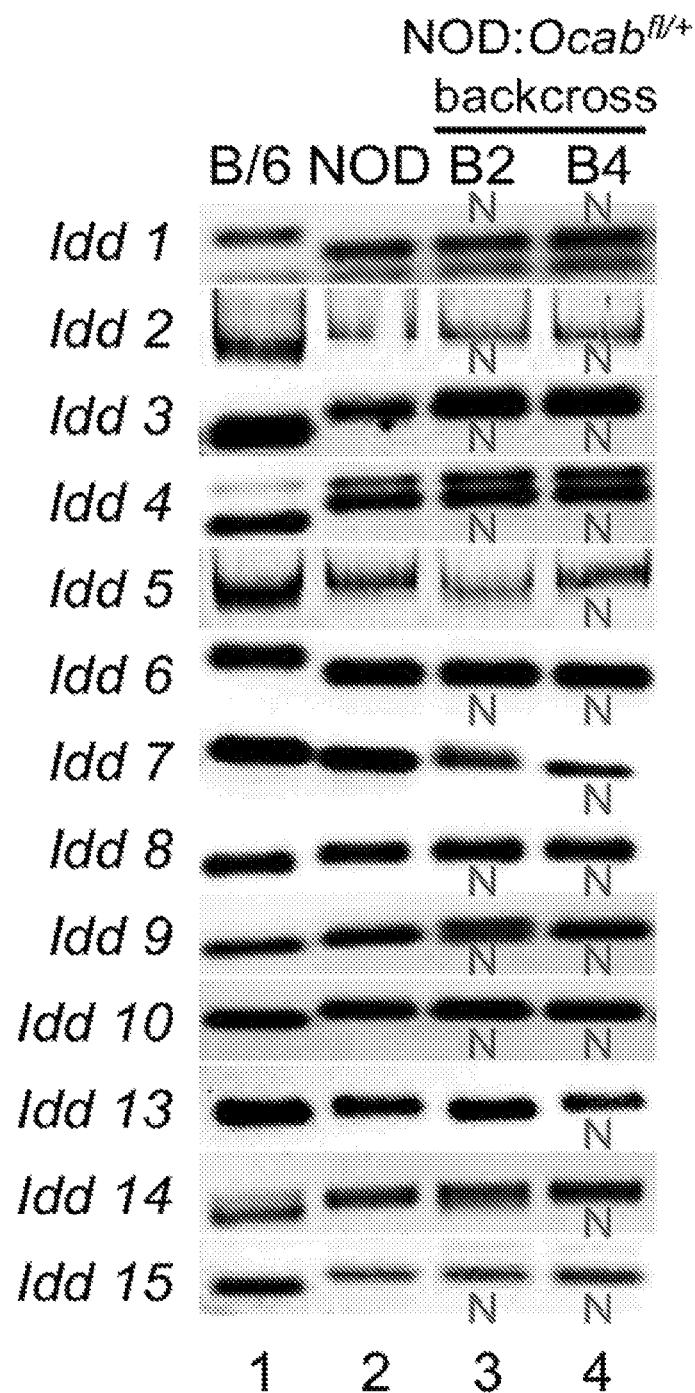
FIG. 5 shows the complete set of immunogenic NOD determinants that promote spontaneous autoimmunity crossed to the OCA-B conditional allele. Agarose gels of PCRs that discriminate NOD vs B/6 alleles are shown. "N" indicates successful backcrossing to the determinants from the NOD background.

A NOD/Ocab conditional knockout mouse. Using a transgenic core facility, a conditional Ocab mouse allele (FIG. 4A-B) was generated. Homozygous floxed mice produce normal amounts of protein, while no protein is present in A/A spleens, indicating that the fl allele is OCA-B sufficient and the Cre-deleted allele is null (FIG. 4C). Crossing onto a CD4-Cre driver results in efficient deletion in splenic T cells (FIG. 4D). These mice were generated on a C57BL/6 background. To test the prediction that OCA-B expression in T cells is required for T1D emergence, speed congenic backcrosses to the NOD strain background were conducted. This method allows mice to be produced rapidly by screening and selecting for 13 microsatellite and SNP markers associated with NOD autoimmune susceptibility. Following these markers, backcrossed animals were produced (FIG. 5) that recapitulated spontaneous autoimmunity (not shown). These animals are being crossed to NOD/CD4-Cre in order to delete OCA-B in T cells to assess the effects on T1D (Example 1).

Rationale: Multiple threads of evidence associate OCA-B with T1D. These data indicate that OCA-B may also offer a valid therapeutic avenue towards targeting this disease. The experiments described here provide the mechanistic backing for this line of inquiry by leveraging the new conditional Ocab mouse allele to test the hypothesis that genetic Ocab deletion is protective in mouse models of T1D.

Determine of loss of OCA-B in T cells reduces T1D incidence or severity in NOD mice. The NOD model is spontaneous and genetically determined but partially penetrant, much like the human disease. Approximately 60-80% of female NOD mice develop T1D in standard environments. To test the prediction that OCA-B expression in T cells is required for T1D emergence, age-matched female NOD Ocab$^{fl/fl}$; CD4-Cre mice, and controls lacking Cre or floxed alleles, for TD emergence, will be followed. Animals will be monitored 2x/week for hyperglycemia and weight loss. Kaplan-Meier plots will be generated to follow disease-free survival. Once diabetes is detected, animals will be sacrificed to assess disease sequelae such as infiltrating lymphocytes in the pancreas (histologically), and reactive cells in the pancreatic lymph nodes (flow cytometry). T cell and macrophage numbers and cytokine production (IL-2, TNFα, IL-17A and IFNγ) will be measured. Auto-reactive CD4 T cells will be scored using BDC2.5 MHC tetramers. As a parallel experiment, another cohort will be sacrificed at a fixed time point of 18 weeks (peak disease). The fraction of animals with T1D involvement will be plotted.

Disease in NOD mice originates from defective negative selection in developing T cells, resulting in T cell autoreactivity. T cell development is not affected in animals lacking OCA-B. Therefore, the effectiveness of the peptide in animal models indicates that OCA-B can be targeted to protect animals from pre-existing autoreactivity. Plot averages and standard deviations of blood glucose levels and weight loss can also be performed.

If OCA-B loss in both models fails to confer protection, knockout of OCA-B using NOD TCR transgenic mice such as BDC2.5 (a CD4-selected transgenic) and NY8.3 (a CD8-selected transgenic) may produce more robust effects.

Example 2: Long-Term Effects and Durability of OCA-B Membrane-Permeable Peptide Inhibitors in NOD Mice The findings described herein show that an OCA-B inhibitor peptide blocks T1D emergence over a short time interval in NOD animals. Many important questions remain, including if the peptide acts through a mechanism involving the OCA-B interaction surface with Jmjd1a (testable with scrambled and point mutant peptides), if the peptide stably blocks disease emergence and becomes chronically or acutely toxic (testable with a longer duration of injections), if the peptide inhibits already established T cell memory (testable with peptide treatments after LCMV infection and clearance), and if the peptide is efficacious against already established T1D (testable by letting animals become fully diabetic before treatment). The experiments in this Example test these predictions.

Determine if chemically synthesized peptides specific to the OCA-B interaction surface with Jmjd1a are non-toxic and stably blunt T1D in NOD animals. The results from FIG. 4 show that brief administration of OCA-B peptides blunts T1D emergence. The peptides described herein can be synthesized on a milligram-scale as well as additional scrambled and double point-mutant peptide controls.

To test effects of peptide treatment on T1D emergence, injections will be given to cohorts of eight female and male NOD mice starting after blood glucose reaches 225 mg/dL. Peptide will be administered every 12 hr thereafter for either 4 or 8 days. 20 mg/kg peptide will be administered intravenously, as described herein. A decreasing dose schedule will be used, and the minimal dose for short-term efficacy (blood glucose, serum insulin) will be calculated. If lower doses generate as complete protection as 20 mg/kg, the following experiments will also use that dose. Tat peptide alone, scrambled peptide, and peptide containing the point mutation shown in FIG. 3 will be used as controls. After each injection, mice will be monitored for labored breathing and shaking to assess immediate toxicity. Animals will be monitored for signs of weight loss and ruffled appearance to assess chronic effects. Blood glucose will be taken before sacrifice. Half of the cohort will be sacrificed for pancreatic histology. Fixed and embedded sections will be H&E stained and analyzed by a pathologist in a blinded fashion. Adjacent sections can be used for IHC with antibodies against CD4, CD8, CD19 and CD11b to identify specific infiltrating T and B cells and macrophages. The remaining four mice will be used for flow cytometry of the pancreata and pancreatic lymph nodes. T cell and macrophage numbers and cytokine production (e.g., cytokines encoded by OCA-B target genes such as IL-2, IFNγ and IL-17A) will be measured. Autoreactive CD4 T cells will be scored using BDC2.5 MHC tetramers.

To test for long-term durability and toxicity, a single set of mice will be injected with peptide #2, twice daily, for 4 weeks. Mice will be monitored immediately after injection for labored breathing and shaking, and longitudinally for weight loss or lethargic/ruffled appearance. If there is durable protection, peptide will be withdrawn after 4 weeks to determine if protection can be maintained without continuous treatment. In a separate experiment, older female NOD animals with full-blown disease will be treated.

Peptide inhibitors are associated with similar caveats as any other drug, including the possibility of toxicity and side effects. OCA-B is thought to be expressed in lymphocytes and the lung epithelium. This narrow expression should minimize side effects due to direct action on OCA-B. Furthermore, OCA-B germline-null mice are viable and fertile, with no evidence of lung pathology. Therefore, it is anticipated that any toxicity will result from off-target effects rather than OCA-B inhibition. If acute or immune toxicity is observed, the register of the peptide sequence will be altered or shifted, and the dose or concentration decreased to limit the effect. The Tat membrane-penetrating peptide has been associated with toxicities, though not in the context of a BCL6 inhibitor peptide. If necessary, other membrane penetrating peptides such as poly-arginine will be used. Assays similar to FIG. 3A will insure that the new peptides are efficacious.

Determine whether OCA-B inhibition affects pre-established T cell memory. OCA-B has already been shown to be dispensable for existing plasma B cell function. In addition, OCA-B levels are much higher in B cells compared to T cells (ImmGen), creating a potential therapeutic window in which specific levels of inhibitor peptide competitively inhibit the interaction with Jmjd1a in T cells but not in B cells. This biology should limit effects of the inhibitor on existing and developing B cell function. For less severe autoimmune diseases and diseases in which pre-existing therapies are available, the potential use of OCA-B inhibition in the clinic as a therapy for autoimmunity will rely in part on whether or not OCA-B is necessary to maintain a pre-existing repertoire of memory T cells. To test effects on memory formation and recall responses, peptide injection experiments will be conducted following infection with the model pathogen LCMV to assess effects on established or existing LCMV-specific memory T cells. Transition from the effector to the memory pool takes 4-6 weeks. 42 days post-infection, cohorts of four C57BL/6 mice will be sacrificed to study CD4 memory using tetramers to identify LCMV-reactive T cells. Other cohorts will be infected at day 42 with Lm-gp61 to test memory recall responses at day 42+7. As with OCA-B genetic deletion, it is expected that peptide treatment will result in fewer CD4 central memory T cells, and failure of this reduced population to mount a recall response. Using sliding 8-day windows of peptide treatment, it will be pinpointed when OCA-B is required. To test effects on pre-established memory, mice at 42-day post-infection will be treated with peptides and rechallenged with recombinant *L. monocytogenes* expressing the LCMV GP$_{61-80}$ CD4 epitope (Lm-gp61). This treatment will selectively reactivate memory CD4 cells specific to this epitope.

A finding that OCA-B is necessary in pre-established CD4 memory T cells would be contrary to the models as they suggest additional unanticipated role in regulation of target gene chromatin. It would also narrow the therapeutic index and potential patient profile, though a viable drug may still emerge targeting OCA-B. More importantly, such a finding would indicate that other components of this pathway, operating downstream of OCA-B in the establishment but not maintenance of memory epigenetic states, would constitute a better therapeutic target.

Determine if recombinant purified peptide can substitute for chemically synthesized peptides. Native peptides are unstable in animals, necessitating the synthesis of large amounts. As an interim solution on a path towards a working drug intervention, the peptide will be cloned, expressed and purified from *E. coli*. Peptide #2 fused to Tat, scrambled peptide control and double point-mutant control peptides will be expressed as His$_{10}$ fusion proteins, with a TEV protease linker between them. The DNA encoding the peptides will be synthesized as double-stranded gene blocks (IDT) and cloned into the BamHI and EcoRI sites of the pNR111 bacterial expression vector. The peptide will be induced with IPTG and purified under denaturing (urea) conditions using nickel-NTA agarose chromatography. This strategy also removes endotoxin. This cloning strategy introduces two N-terminal amino acids into the peptide, which must therefore be re-validated. The chemically synthesized peptide already contains a tyrosine at the C-terminus for quantification purposes, which will also be used for bacterial purification. Efficacy can first be tested in cells as in FIG. 3A before moving to mouse models.

If recombinant peptides do not recapitulate the effects of chemically synthesized peptides, another approach is to take advantage of stapled, PEGylated or circularized peptides. These modifications increase serum half-life and thus lower the amount of peptide required. In the longer term, peptide inhibition can be an intermediate step towards a bona fide drug intervention, one that allows function, side effects, etc. to be assessed. The development of small molecules mimicking effects of the peptide is also within the scope of this disclosure. Although sequence-specific DNA binding transcription factors are commonly (and erroneously) thought of as "undruggable", the interface between a transcription cofactor (OCA-B) and a chromatin-modifying enzyme (Jmjd1a), an area of gene regulation successfully targeted before, is being inhibited.

Example 3: Mice Lacking Oct1 in T Cells are Protected in MOG/EAE Models

Figure 6A:
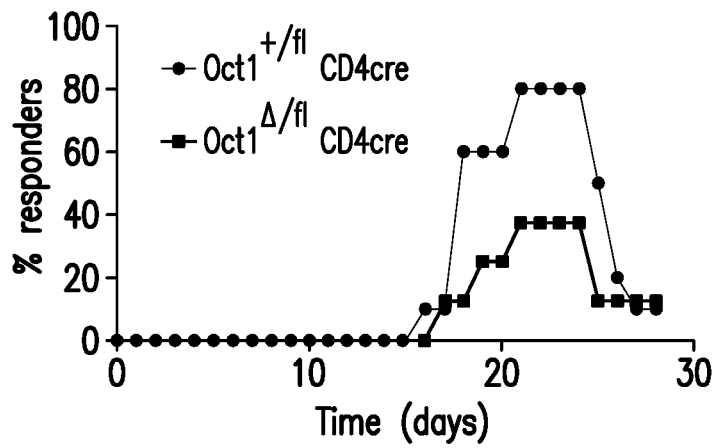
FIGS. 6A-C shows that T cell conditional Oct1 loss protects mice from EAE.
Figure 6B:
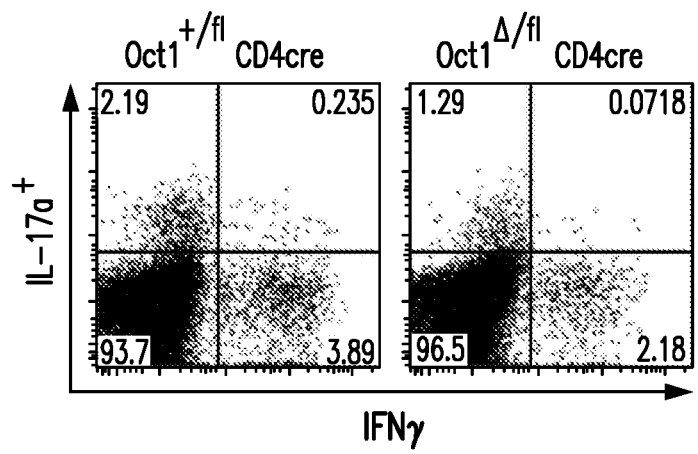

Oct1fl/fl; CD4-Cre animals inoculated with mouse MOG35-55 in the presence of complete Freund's adjuvant (CFA), followed by injections of pertussis toxin results in generation of an autoimmune neuroinflammatory demyelinating disease driven by $MOG_{3555}$-reactive CD4+ T cells. This standard protocol results in a classic self-limited monophasic disease pattern that includes weight loss, ascending paralysis and resolution. Mice were evaluated using a standard clinical scoring system. The data in FIG. 6A (by percent responders) and by clinical score (not shown) show that T cell-specific Oct1 loss results in decreased disease frequency and severity. After disease resolution, fewer pathogenic cervical lymph node IFNγ/IL-17A double-producer T cells were observed (FIG. 6B, C). Histopathological analysis of spinal cords confirmed these findings. These results indicate that loss of Oct1 protects animals in the MOG/EAE model.

Figure 6C:
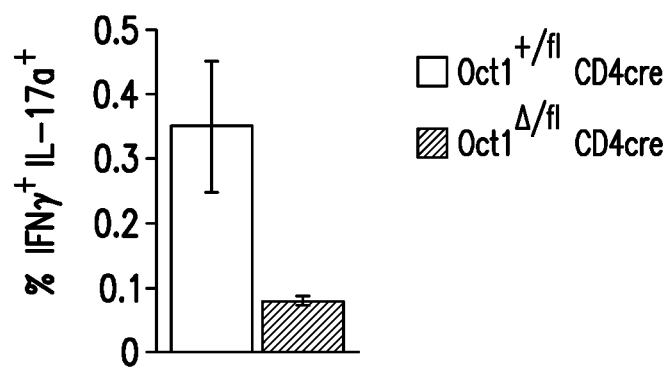
Figure 10:
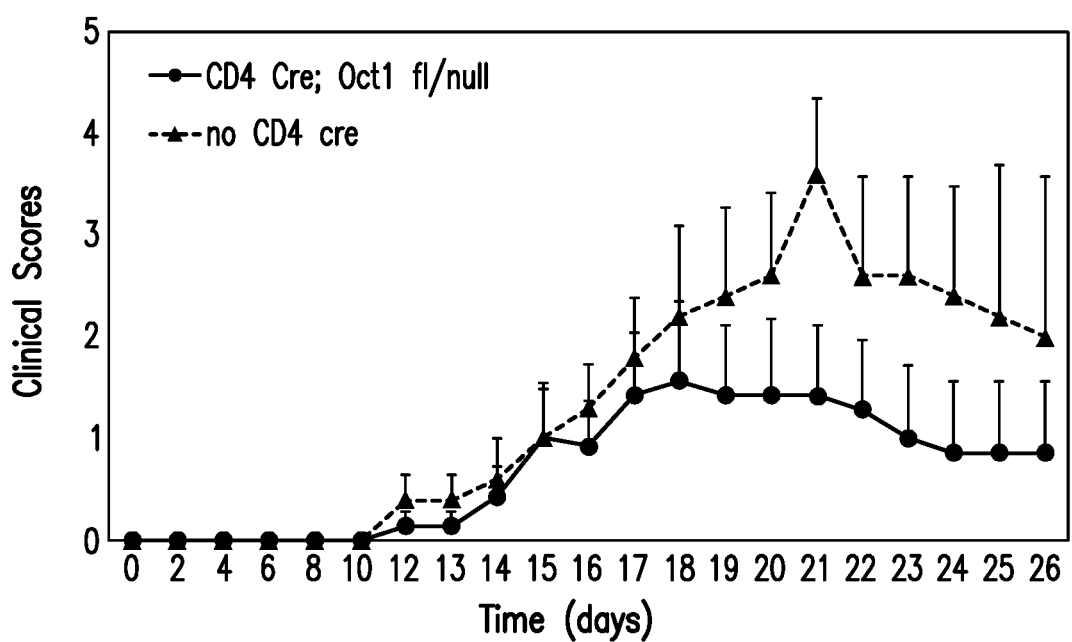
FIG. 10 shows that deletion of Oct1 (the transcription factor OCA-B associates with) in T cells results in protection in a Myelin oligodendrocyte glycoprotein (MOG)/Pertussis toxin (PT) experimental autoimmune encephalomyelitis (EAE) mouse model of multiple sclerosis (MS).
Figure 11A:
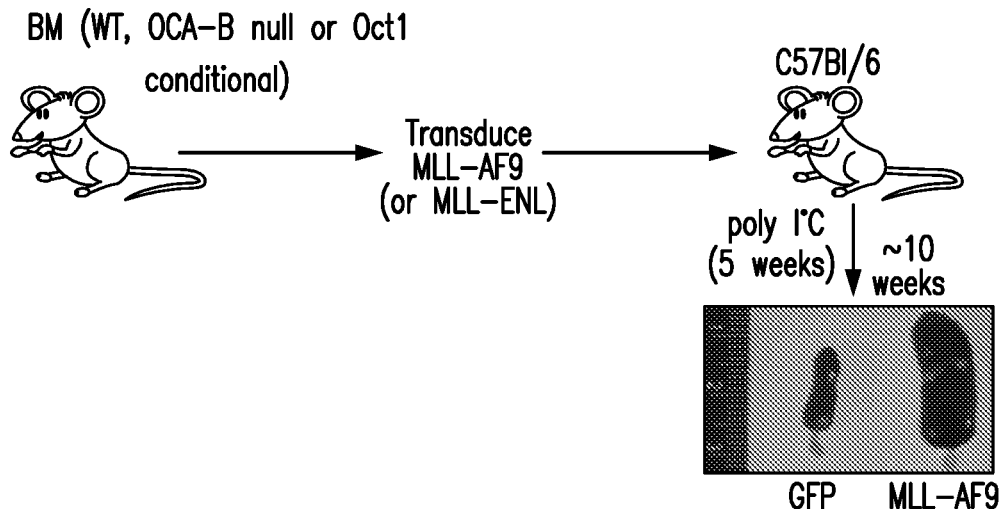
FIGS. 11A-D show that Ocab$^{-/-}$ mice are protected from leukemia.
Figure 11B:
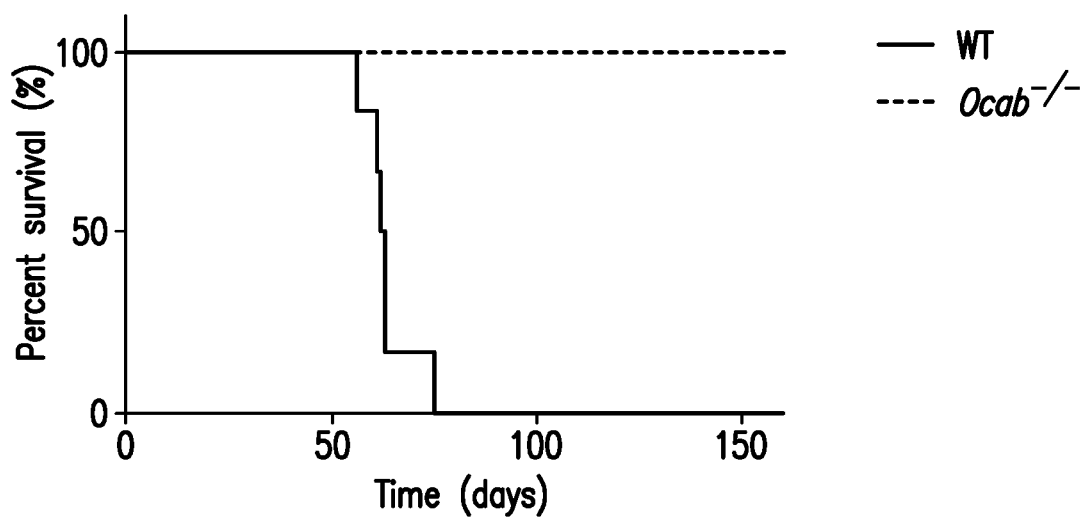
Figure 11C:
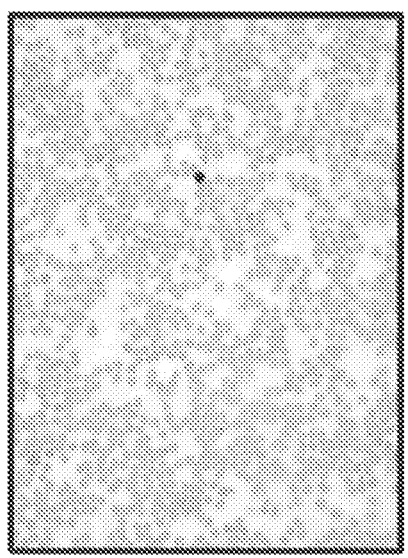
Figure 11C:
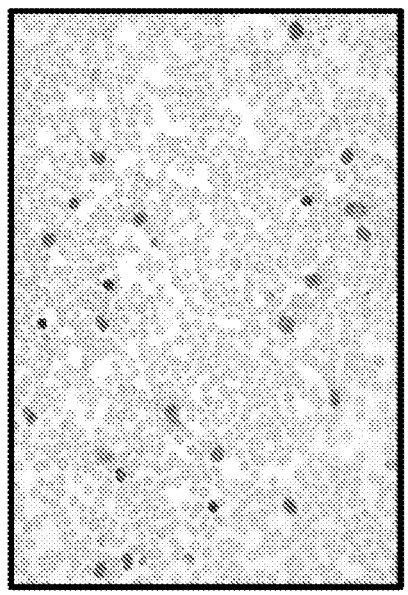
Figure 11D:
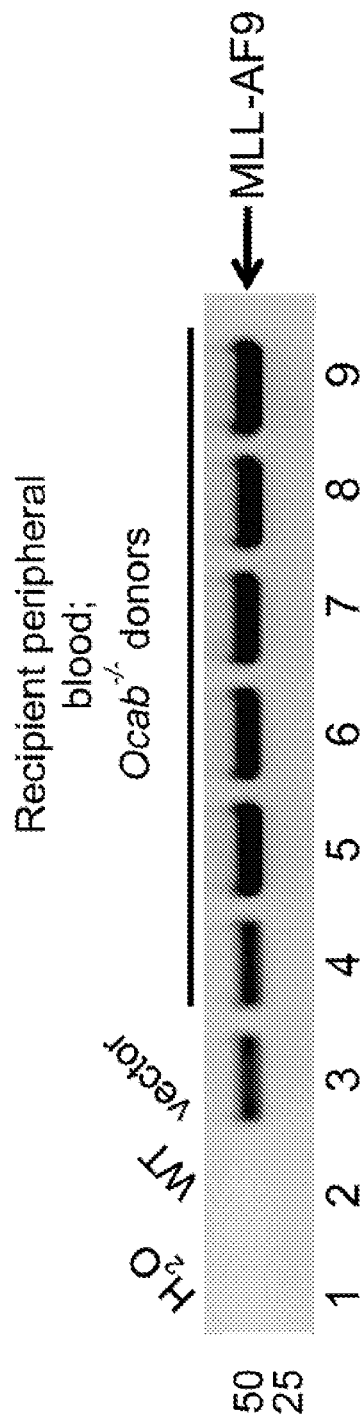

Example 4: Determine Long-Term Effects and Durability of OCA-B Membrane-Permeable Peptide Inhibitors in Mouse Models of MS To test for long term toxicity, 5 C57BL/6 mice per group will be injected with 5-20 mg/kg, twice daily, for 4 weeks. After injection, mice will be monitored for labored breathing and shaking to assess immediate toxicity. Long term, animals will be monitored for weight loss and ruffled appearance. To study a possible side effect caused by OCA-B inhibition, the formation of new memory cells in these mice will be studied. Experiments similar those described herein will be conducted with the addition of infection with an extensively characterized mouse model virus known as LCMV. Using specific probes of LCMV-specific T cells known as tetramers, the effects on establishing LCMV-specific memory T cells will be assessed. To test efficacy in MS models, the $MOG_{35-55}$-induced EAE (Waldor et al. Science, 1985, 227:415-7 will be used. Briefly, 8 week-old female animals will be treated for 4 weeks (or shorter if unexpected toxicity is observed). Within this time course, mice will be administered MOG peptide/PT as in FIG. 6, and clinical course monitored. At peak disease, a subset of mice in each group will be sacrificed and used to flow cytometry of cervical lymph nodes and CNS. Another subset will have spinal cords embedded, sectioned and analyzed for infiltrating leukocytes and demyelination. FIG. 10 shows the deletion of Oct1 (the transcription factor OCA-B sits on) in T cells: protection in MOG/PT EAE.

Using histopathological analysis, the hypothesis that peptide treatment will decrease neuroinflammation and infiltrating leukocytes will be tested. Using Luminex, T cell and serum cytokine production will be probed, with the expectation that expression of cytokines encoded by direct target genes (e.g., GM-CSF, IL-17 and IFNγ) will be significantly reduced. To test durability of response, mice will be treated, then maintained without further injections and administered MOG/PT. Lastly, NOD animals will be treated, which respond to MOG/PT with a progressive clinical pattern rather than the disease-remission seen in C57BL/6 mice. These experiments will establish whether peptide administration shows efficacy in aggressive primary-progressive disease.

OCA-B germline null mice are viable and fertile. OCA-B is mainly expressed in lymphocytes and the lung epithelium. This narrow expression spectrum minimizes side effects due to direct action of peptide on OCA-B.

To provide a genetic underpinning to the pharmacological experiments, a new conditional Ocab mouse allele (FIG. 4A) will be deployed, with CD4-Cre to delete in T cells, in the MOG/EAE model. It is predicted that T cell-specific Ocab deletion will significantly blunt disease effects in both models.

Example 5: Ectopic OCA-B Expression in T Cells Promotes Memory In Vivo

Figure 7:
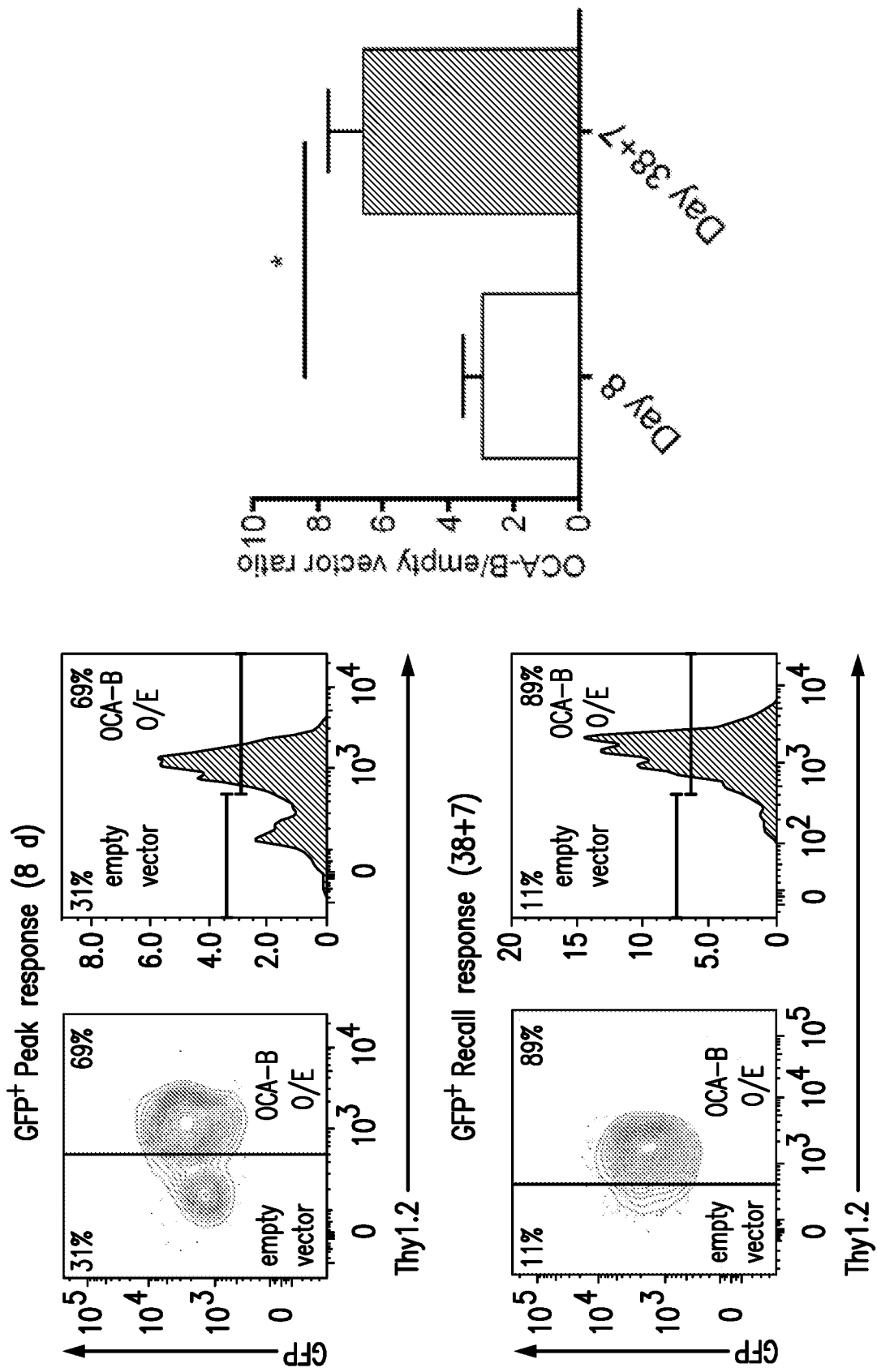
FIG. 7 shows that ectopic OCA-B expression in CD4 T cells promotes memory in vivo. Left panel: Representative plots of co-transferred Thy1.1 and 1.2 SMARTA cells (SMARTA are an LCMV-reactive TCR transgenic mouse line) at peak LCMV response and at following heterologous rechallenge with Lm-GP61; cells were first transduced with control MIG or vectors encoding OCA-B. Right panel: Quantification from multiple animals. Error bars denote standard deviation.
Figure 8:
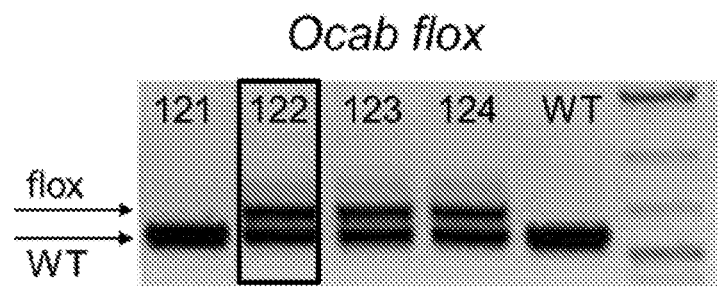
FIG. 8 shows, genomic PCR to follow the Ocab floxed allele through NOD backcrosses (top panel); markers for NOD background screening (bottom panel).
Figure 9A:
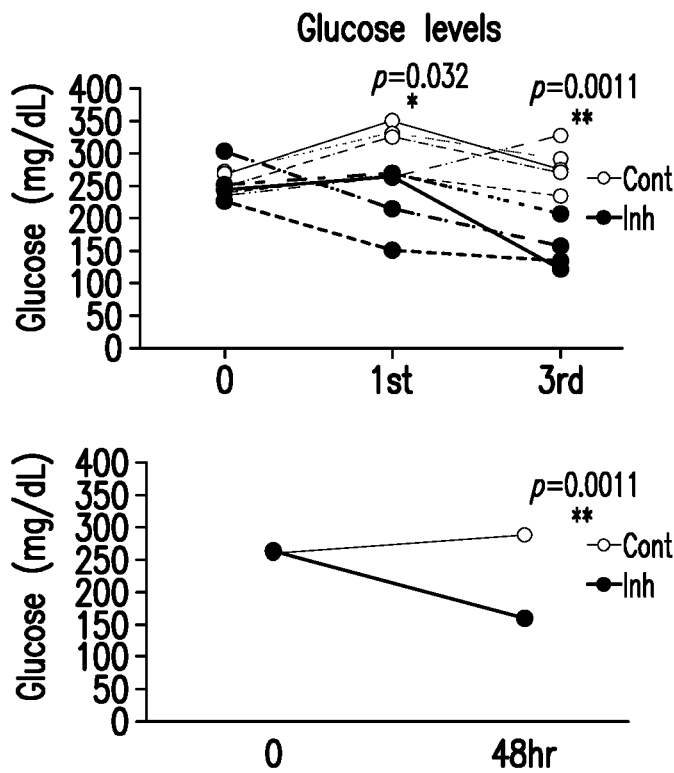
FIGS. 9A-D shows "JumOCA" peptide efficacy.
Figure 9B:
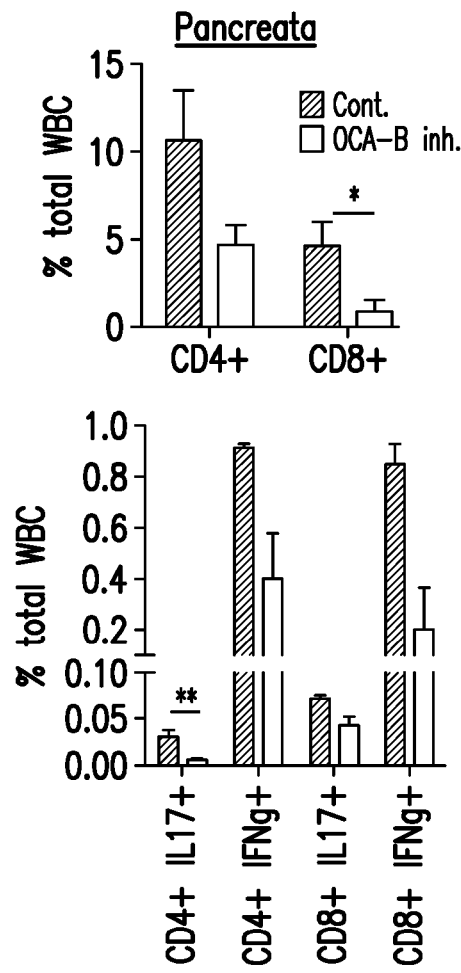
Figure 9C:
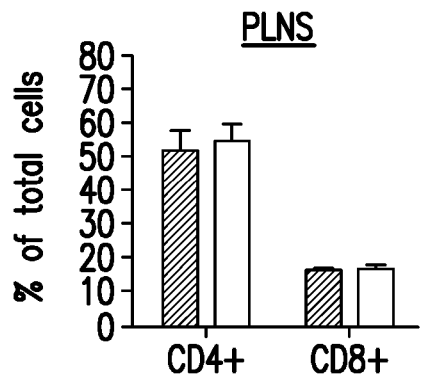
Figure 9D:
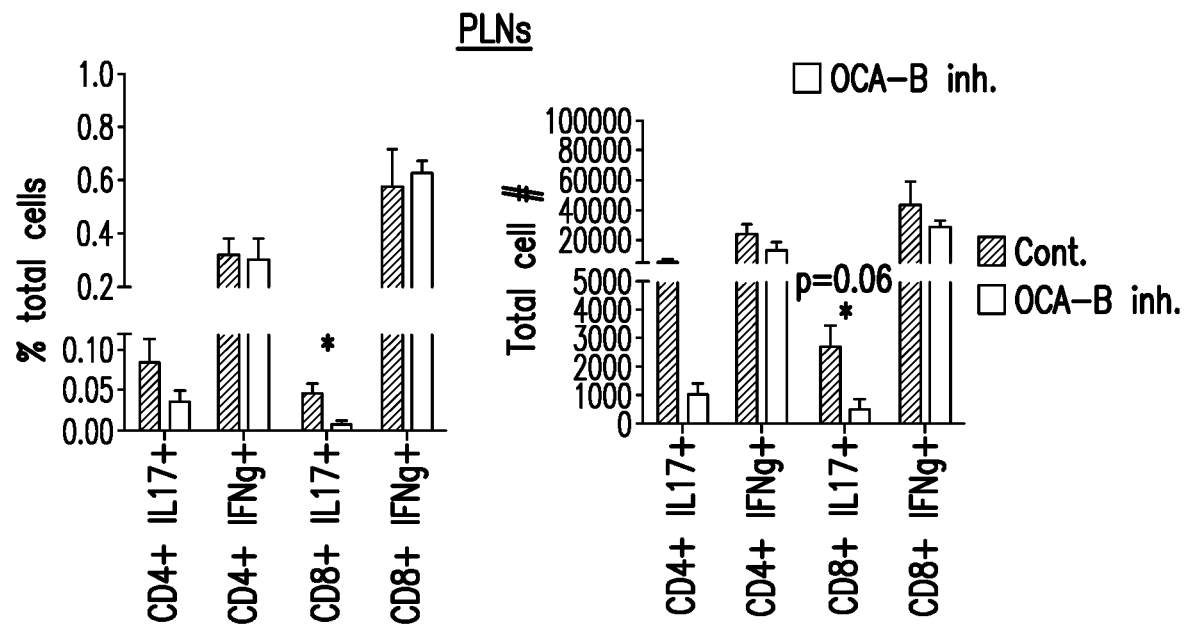

Materials and methods: Thy1.1+ and Thy1.1+/1.2+ donor mice were inoculated with the LCMV immunodominant peptide to promote stimulation (full stimulation does not occur without pathogenic and costimulatory signals) to allow for transduction. Twenty four hours later, T cells were isolated and transduced ex vivo with either empty vector (Thy1.1) or MSCV-IRES-GFP (MIG) vector encoding murine OCA-B (Thy1.1/1.2). Cells were combined 1:1 and transferred into C57BL/6 (Thy1.2) recipients. Twenty four hours later, animals were infected with LCMV. Subsets of mice were euthanized and necropsied at peak response and following viral clearance, establishment of memory, and heterologous rechallenge with *Listeria monocytogenes* expressing the SMARTA epitope (Lm-GP61). Cells were gated based on CD4 and GFP expression, and Thy1.2 positivity was used to calculate the ratio of empty vector vs. OCA-B overexpressing cells. The results are shown in FIG. 7.

Example 6: Ocab$^{-/-}$ Mice are Protected from Leukemia

A transduction/transplant system to model MLL-AF9-driven leukemia in the mouse was used (see, FIG. 11). In this model, BM progenitors are transduced with MSCV-MLL-AF9-IRES-GFP. The fusion protein encoded by this construct is associated with aggressive forms of AML. Mice transplanted with transduced cells efficiently develop oligoclonal AML and succumb within ~10 wks. Signs of leukemia such as hypercellularity and increased myeloblast concentration in peripheral blood can be monitored using a Hemavet. Leukemic cells were also monitors using GFP encoded in the vector.

Example 7: T Cell-Selective Deletion of Oct1 Protects Animals from Autoimmune Neuroinflammation while Maintaining Neurotropic Pathogen Response Abstract Background: Treatments for autoimmune diseases aim to dampen autoreactivity while preserving normal immune function. In CD4$^+$ T cells, the transcription factor Oct1/Pou2f1 is a dispensable transcription factor for T cell development and response to primary infection, but promotes expression of target genes, including Il2 and Ifng, under conditions of antigen reencounter. As a result, they are more strongly expressed upon secondary stimulation. Such repeated antigen encounters occur in memory recall responses, in autoimmunity where self-antigen can be recognized multiple times, and in chronic infection where foreign antigen is persistent. Based on these previous findings, it was tested whether Oct1 loss would protect animals from autoimmunity but maintain normal responses to pathogens in the CNS.

Objective: A conditional mouse Oct1 (Pou2 fl) allele and a CD4-Cre driver was used to determine the effect of T cell-specific Oct1 loss on autoimmune- and viral-induced neuroinflammation using an autoantigen-driven EAE model of autoimmunity and a JHMV model of viral infection.

Results: Oct1 conditional deletion mitigated clinical scores and reduced infiltrating T cells and cytokine production in the EAE model. Consistently, Oct1-deficient CD4$^+$ T cells stimulated in vitro showed increased expression of markers associated with T cell anergy, particularly in the absence of co-stimulatory signals. In contrast, anti-viral T cell effector functions are intact in the absence of Oct1, with no changes in neuroinflammation, infiltrating T cells or cytokine production.

Conclusion: These findings uncover a significant difference between the effect of Oct1 loss on autoimmune and anti-pathogen responses, which potentially could be exploited for therapeutic benefit.

Introduction

Multiple sclerosis (MS) is a chronic debilitating neurological disease characterized by inflammation, demyelination, and neuronal damage caused by the inappropriate response of the host immune system towards cells of the central nervous system (CNS) (Steinman L.

Annu Rev Immunol. 2014; 32:257-81). Although the pathophysiology of MS is not entirely understood, active MS lesions are characterized by CNS infiltration by both CD4$^+$ T cells—arranged around the periphery of active MS lesions—and CD8$^+$ T cells (typically perivascular), with the subsequent activation of microglial cells, macrophages and B cells (Rumble J M, et al. J Exp Med. 2015; 212:23-35). CD4$^+$ T cells can be thought of as master regulators of the immune response during MS, whereas perivascular CD8$^+$ T cells, microglial cells, macrophages, and even neutrophils largely mediate white matter damage (Rumble J M, et al. J Exp Med. 2015; 212:23-35). Genome-wide association studies (GWAS) pinpoint the major histocompatibility complex (MHC) genes located in the human leukocyte antigen (HLA) region as having the strongest influence on disease, further emphasizing the importance of T cells in MS pathophysiology (Patsopoulos NA. Cold Spring Harb Perspect Med. 2018; 8:a028951).

Oct1/Pou2 fl is a POU-domain transcription factor that in mice is dispensable for T cell development and response to primary infection, but is important for the formation of CD4$^+$ central memory cells (Shakya A, et al. J Exp Med. 2015; 212:2115-31). Consequently, CD4$^+$ T cells lacking Oct1 are completely defective in memory recall responses. Memory T cells are highly prone to making proinflammatory cytokines, and memory or memory-like cells can underlie autoimmunity (including T1D), even in cases of persistent self-antigen exposure (Kawakami N, et al. J Immunol. 2005; 175:69-81; Chee J, et al. J Immunol. 2014; 192:572-80; and Yeo L, et al. J Clin Invest. 2018; 128:3460-74). In vitro, Oct1 and its cofactor OCA-B coordinately control a large cohort of important direct target genes in CD4$^+$ lymphocytes, including Il2, Il21, Stat5a, Ifng, Tbx21 (Tbet), Csf2 (Gmcsf), Tnfrsf4 (Ox40), Icos and Ctla4 (Shakya A, et al. J Exp Med. 2015; 212:2115-31). Interestingly, Oct1 and OCA-B are dispensable for the baseline activity of these genes. For example, CD4$^+$ T cells lacking Oct1 due to germline or conditional deletion develop normally and express normal levels of the key T cell effector cytokine gene IL-2 upon primary stimulation (Shakya A, et al. J Exp Med. 2015; 212:2115-31; and Shakya A, et al. J Biol Chem. 2011; 286:450-9). Instead, Oct1 and OCA-B strongly regulate these genes under conditions of antigen re-encounter such that secondary stimulation of resting but previously activated cells results in expression defects of 20-fold (Shakya A, et al. J Biol Chem. 2011; 286:450-9). During CD4$^+$ T cell polarization, Oct1 works together with another transcription factor, CTCF, to mediate physical communication between the Il4, Ifng and Il7a target loci (Kim L K, et al. 2014; 54:56-66). The Oct1 cofactor OCA-B/Bob.1 has also been linked to CD4$^+$ central memory cell formation and function, and to the formation of Th17 cells (Shakya A, et al. J Exp Med. 2015; 212:2115-31; and Yosef N, et al. Nature. 2013; 496:461-8). Cumulatively, the findings point to a potent role of Oct1 and OCA-B in the control of CD4$^+$ T cell responses, but under specific circumstances involving repeated antigen exposure. This normal development and stimulation response forms part of a potential "therapeutic window" in which targeting Oct1 and its associated pathways could be used to treat autoimmune responses while sparing normal immune function.

In addition to immune memory, repeated antigen encounter also occurs in situations such as chronic infection, graft-versus-host disease, tumor immunity and autoimmunity. In the case of the latter, human GWAS studies show strong associations between polymorphisms in binding sites for Oct1 and predisposition for autoimmune disease including rheumatoid arthritis, celiac disease, type-1 diabetes, ulcerative colitis, autoimmune thyroiditis and MS (Maurano M T, et al. Science. 2012; 337:1190-51 Farh K K-H, et al. Nature. 2015; 518:337-43; van Heel D A, et al. Hum Mol Genet. 2002; 11:1281-9; and Graham D S C, et al. Hum Mol Genet. 2006; 15:3195-205). The strong associations with processes governing neuroinflammatory disease, and MS in particular, lead to the consideration of the role of Oct1 in neuroinflammatory T cell responses to autoantigens and viral infection.

Here, the data show that Oct1 loss in T cells greatly attenuates clinical responses, T cell infiltration, and cytokine production in a murine experimental autoimmune encephalomyelitis (EAE) model, while maintaining immune responses to JHMV infection. EAE is auto-antigen-driven and is the prototypic mouse model of MS. The decreased clinical responsiveness was associated with changes in the expression of anergy-associated surface proteins on CD4$^+$ T cells upon stimulation in vitro, in particular in the absence of co-stimulatory signals. Using a model of neuroinflammation induced by i.c. infection by the neurotropic JHM strain of mouse hepatitis virus (JHMV), few differences in clinical scores, infiltrating T cells and macrophages, and cytokine expression was observed. Viral clearance was slowed but complete in animals with Oct1 deficient T cells. Cumulatively, these results suggest that targeting pathways involving Oct1 in CD4$^+$ T cells may provide a novel therapeutic avenue for the treatment of MS and other neuroinflammatory diseases, while largely sparing beneficial immune function.

Material and Methods

Laboratory mice. Mice used in this study were on the C57BL/6J strain background. Oct1 (Pou2 fl) conditional mice crossed to CD4-Cre have been previously described (Shakya A, et al. J Exp Med. 2015; 212:2115-31).

Induction and scoring of EAE. EAE was initiated using a myosin oligodendrocyte protein (MOG)/*Bordetella pertussis* toxin (PT) method (Grist J J, et al. Eur J Immunol. 2018; 48:1199-210). Briefly, mice were subcutaneously injected with 0.2 μmol of MOG$_{35-55}$ peptide (MEVGWYR-SPFSRVVHLYRNGK (SEQ ID NO: 35), synthesized at University of Utah HSC Core) in complete Freund's adjuvant (CFA, Sigma, 2 mg/mL). 200 ng of PT (Sigma) was injected into the mice twice intravenously. Clinical scores were determined based on the following criteria: 0, no clinical disease; 1, loss of tail tonicity; 2, mild hind limb paresis; 3, moderate hind limb paralysis; 4, paraplegia; 5, quadriplegia, coma or death.

Leukocyte isolation and intracellular cytokine staining. Leukocytes were isolated from spinal cords and cervical lymph nodes using a Percoll gradient method (Stiles L N, et al. J Immunol. 2006; 177:8372-80; Stiles L N, et al. Eur J Immunol. 2006; 36:613-22; and Stiles L N, et al. Autoimmunity. 2009; 42:484-91). Briefly, tissues were dissociated by grinding, and passed through a nylon strainer. Cells were centrifuged with 80% and 40% Percoll at 1300×g at room temperature. Cells at the interface between 40% and 80% Percoll were taken. For intracellular staining, isolated cells were stimulated with PMA (Sigma, 50 ng/mL) and ionomycin (Sigma, 1 g/mL) along with brefeldin A (Golgi Plug, Becton-Dickenson) for 4 hr and were fixed with cell fixation/permeabilization solution (BD Cytofix/Cytoperm™) according to manufacturer's protocol. Antibodies used for flow cytometry were as follows: FITC conjugated anti-mouse CD4 (Biolegend), PerCP conjugated anti-mouse CD8a, APC conjugated anti-mouse IFNγ and PE conjugated anti-mouse IL-17 (eBioscience).

In vitro culture. Single-cell suspensions from CD4-Cre; Oct1$^{fl/fl}$ or control Oct1$^{fl/fl}$ mice were prepared by grinding spleens through 70 m strainers. CD4$^+$ T cells were isolated by a mouse CD4$^+$ T-cell isolation kit (Miltenyi Biotec). The isolated CD4$^+$ T cells were cultured as described previously (Shakya A, et al. J Biol Chem. 2011; 286:450-9), and stimulated with 5 g/ml plate-bound anti-CD3s (BD Bioscience) and 2 g/ml anti-CD28 antibodies (eBioscience) for 24 hr.

JHV. For intracranial (i.c.) injections, age-matched (5-7 weeks) C57BL/6 mice of different genotypes were anesthetized with an intraperitoneal (i.p.) injection of 200 μL of a mixture of ketamine (Hospira, Lake Forest, IL, USA) and xylazine (Phoenix Pharmaceutical, Saint Joseph, MO, USA) in Hank's balanced salt solution (HBSS). Mice were injected i.c. with 200 plaque-forming units (PFU) of JHMV (strain V34) suspended in 30 μL HBSS. Clinical severity was assessed using a previously described four-point scoring scale (Dickey L L, et al. J Neuroinflammation. 2016; 13:240). For analysis of viral titers, mice were sacrificed at indicated time points. One half of each brain was homogenized and used in a plaque assay performed using the DBT mouse astrocytoma cell line ((Dickey L L, et al. J Neuroinflammation. 2016; 13:240).

Cell isolation and flow cytometry. Immunophenotyping of immune cells present within brains and spinal cords of JHMV-infected mice at defined times post-infection (p.i.) was accomplished by homogenizing isolated tissue and generating single-cell suspensions for analysis by flow cytometry (Dickey L L, et al. J Neuroinflammation. 2016; 13:240; Marro B S, et al. J Immunol. 2016; 196:1855-64; and Blanc C A, et al. J Neuroinflammation. 2014; 11:138). In brief, isolated cells were stained with the following antibodies: APC-conjugated rat anti-mouse CD4 and a PE-conjugated tetramer specific for the CD4 immunodominant epitope present within the JHMV matrix (M) glycoprotein spanning amino acids 133-147 (M133-147 tetramer) to determine total and virus-specific CD4$^+$ cells, respectively (Dickey L L, et al. J Neuroinflammation. 2016; 13:240; Marro B S, et al. J Immunol. 2016; 196:1855-64; and Blanc C A, et al. J Neuroinflammation. 2014; 11:138); APC-conjugated rat anti-mouse CD8a and a PE-conjugated tetramer specific for the CD8 immunodominant epitope present in the spike (S) glycoprotein spanning amino acids 510-518 (S510-518) to identify total and virus-specific CD8$^+$ cells, respectively (Dickey L L, et al. J Neuroinflammation. 2016; 13:240; Marro B S, et al. J Immunol. 2016; 196:1855-64; and Blanc C A, et al. J Neuroinflammation. 2014; 11:138). Tetramers were synthesized by NIH tetramer core facility. APC-conjugated rat anti-mouse CD4 and PE-conjugated anti-CD25 to determine total T-regulatory cells; and BV510-conjugated rat anti-mouse CD45 and FITC-conjugated anti-F4/80 to identify macrophages. Samples were analyzed using a BD LSR Fortessa X-20 flow cytometer and FlowJo software.

Histology. Spinal cords were isolated at defined time points and fixed overnight with 4% paraformaldehyde at 4° C. Sections were subsequently cryoprotected in 30% sucrose for 5-7 days, separated into 12 coronal sections, and embedded in optimum cutting temperature (OCT) formulation (VWR, Radnor, PA, USA) (Grist J J, et al. Eur J Immunol. 2018; 48:1199-210; Dickey L L, et al. J Neuroinflammation. 2016; 13:240; Marro B S, et al. J Immunol. 2016; 196:1855-64; and Blanc C A, et al. J Neuroinflammation. 2014; 11:138); APC-conjugated rat anti-mouse CD8a and a PE-conjugated tetramer specific for the CD8 immunodominant epitope present in the spike (S) glycoprotein spanning amino acids 510-518 (S510-518) to identify total and virus-specific CD8$^+$ cells, respectively (Dickey L L, et al. J Neuroinflammation. 2016; 13:240; Marro B S, et al. J Immunol. 2016; 196:1855-64; and Blanc C A, et al. J Neuroinflammation. 2014; 11:138). Coronal sections (8 μm thick) were cut, and sections were stained with luxol fast blue (LFB) in combination with hematoxylin and eosin (H&E). Areas of total white matter and demyelinated white matter were determined with Image J Software. The percent demyelination was calculated by dividing the area of demyelinated white matter by the total white matter area using established methods (Dickey L L, et al. J Neuroinflammation. 2016; 13:240).

Statistical analysis. The error bars denote SEM. Student T-tests were used to ascribe statistical significance. For all figures, *=p-value≤0.05; **=p-value≤0.01.

Results

Figure 12C:
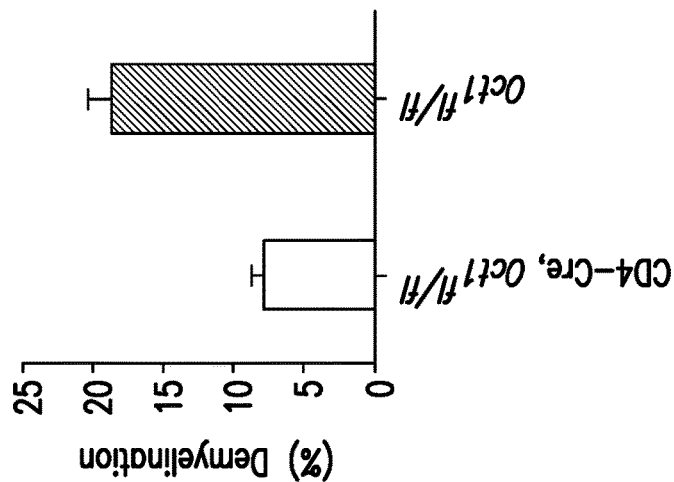
Figure 12A:
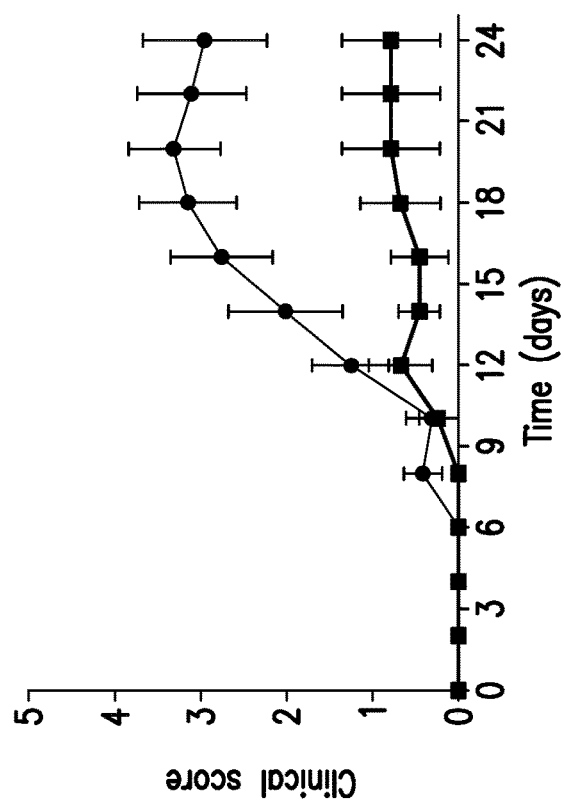
Figure 12B:
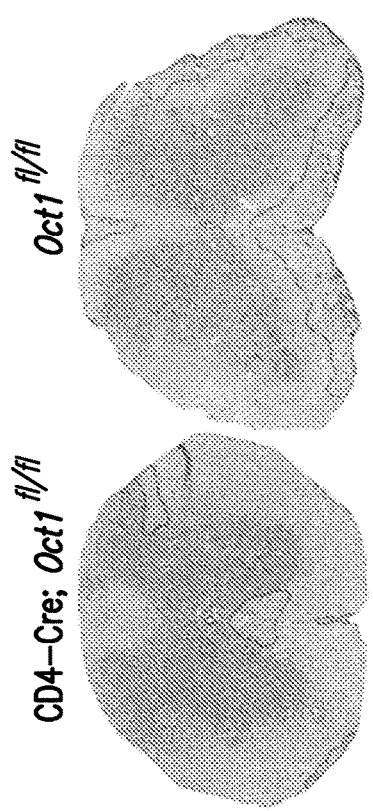

To determine the effects of Oct1 in T cells on the pathogenesis of a neuroautoimmune disease, Oct1 T cell conditional mice (CD4-Cre; Oct1$^{fl/fl}$ (Shakya A, et al. J Exp Med. 2015; 212:2115-31) and control mice (Oct1$^{fl/fl}$) were used in conjunction with a MOG-EAE model of MS. Following inoculation with peptide corresponding to myelin oligodendrocyte glycoprotein ($MOG_{35-55}$, see methods) and with Freund's complete adjuvant, pertussis toxin was injected into mice to increase blood brain barrier permeability. Disease severity was determined by evaluating clinical score. C57BL/6 mice develop clinical symptoms 9-14 days after MOG injection (Bittner S, et al. J Vis Exp. 2014; 15; (86)). As shown in FIG. 12A, CD4-Cre; $Oct1^{fl/fl}$ mice were significantly protected, with clinical scores less than 1, while the control $Oct1^{fl/fl}$ mice exhibited much higher clinical involvement at the peak point of disease (day 20, FIG. 12A). Additionally, spinal cords were collected for histopathological scoring 21 days after EAE induction. The degree of demyelination in control mice was double that of the CD4-Cre; $Oct1^{fl/fl}$ group (FIGS. 12B, 12C). These results reveal that Oct1 deletion in T cells strongly protects mice from clinical symptoms in a MOG-EAE model of MS.

T cells are indispensable for the pathogenesis of EAE and MS (Goverman J. Nat Rev Immunol. 2009; 9:393-407). IFNγ and IL-7 expression in CNS-infiltrating Th1 and Th17 $CD4^+$ T cells in EAE correlates with clinical severity (Goverman J. Nat Rev Immunol. 2009; 9:393-407; Segal B M, et al. J Exp Med. 1996; 184:771-5; and Langrish C L, et al. J Exp Med. 2005; 201:233-40). Both $CD4^+$ and $CD8^+$ T cells contribute to clinical and histologic disease. $CD8^+$ T cells are recruited to lesions and mediate the destruction of oligodendrocytes and axons (Goverman J, et al. Curr Drug Targets Inflamm Allergy. 2005; 4:239-45; and Friese M A, et al. Brain. 2005; 128:1747-63). Therefore, T cell populations in the draining cervical lymph nodes (CLNs) and in the spinal cords of Oct1 conditional and control mice were screened at the peak of disease progression to determine if T cells lacking Oct1 have reduced autoimmune activity in the CNS and CLNs. Although the percentages of CLN $CD4^+$ and $CD8^+$ were similar between the groups (FIGS. 12D, 12E left panel), fewer ($p<0.01$) total $CD4^+$ and $CD8^+$ T cells were detected in the CD4-Cre; $Oct1^{fl/fl}$ group compared to control $Oct1^{fl/fl}$ mice (FIG. 12E, right panel). This result is suggestive of reduced lymph node cellularity in the EAE model. Because $CD4^+$ T cells are the primary inducers in EAE models (Goverman J. Nat Rev Immunol. 2009; 9:393-407), cytokine production was also profiled in these cells. Both frequencies and total numbers of IL-17- and IFNγ-producing $CD4^+$ T cells were reduced in the CLNs of CD4-Cre;$Oct1^{fl/fl}$ mice compared to $Oct1^{fl/fl}$ controls (FIGS. 12F, 12G). As with CLNs, frequencies of $CD4^+$ and $CD8^+$ T cells were similar in the spinal cords of CD4-Cre;$Oct1^{fl/fl}$ and $Oc1^{fl/fl}$ mice (FIG. 12H). Total numbers of $CD4^+$ and $CD8^+$ T cells were also similar between CD4-Cre;$Oct1^{fl/fl}$ and $Oct1^{fl/fl}$ mice. However, as in the CLNs, proinflammatory cytokine production was strongly reduced in the infiltrating T cells in the spinal cords of CD4-Cre;$Oct1^{fl/fl}$ mice compared to controls (FIG. 12I). These data indicate that loss of Oct1 in T cells strongly protects animals from clinical symptoms of EAE, and that this protection is associated with decreased CNS T cell infiltration and proinflammatory cytokine expression.

T cell anergy is a peripheral tolerance mechanism induced by TCR stimulation in the absence of co-stimulatory signals, in which T cells become poorly reactive, protecting animals from potential autoreactivity (Kearney E R, et al. Immunity. 1994; 1:327-39; Vanasek T L, et al. J Immunol. 2001; 167:5636-44; Kalekar L A, et al. Nat Immunol. 2016; 17:304-14; and Chai J G, et al. Int Immunol. 1997; 9:935-44). Oct1 loss results in decreased expression of target genes such as Ifng, selectively in the context of repeated T cell stimulation (Shakya A, et al. J Biol Chem. 2011; 286:450-9). Gene expression profiling using $CD4^+$ T cells deficient in the Oct1 cofactor OCA-B reveals that these genes are down-regulated as well as identifies increases in the expression of genes associated with anergy, e.g., Ctla4 (Shakya A, et al. J Exp Med. 2015; 212:2115-31). Anergic responses can be modeled in vitro by providing T cells with primary TCR simulation (via immobilized anti-CD3s monoclonal antibodies) in the absence of co-stimulation (Chai J G, et al. Int Immunol. 1997; 9:935-44). To determine the effect of Oct1 loss on anergic responses, $CD4^+$ $CD44^+$ T cells (consisting mostly of pre-activated resting cells) were harvested from CD4-Cre;$Oct1^{fl/fl}$ and control CD4-Cre animals, stimulated them for 24 hours ex vivo using anti-CD3 antibodies with or without CD28 co-stimulation, and profiled the expression of proteins associated with activation and anergy.

Figure 13A:
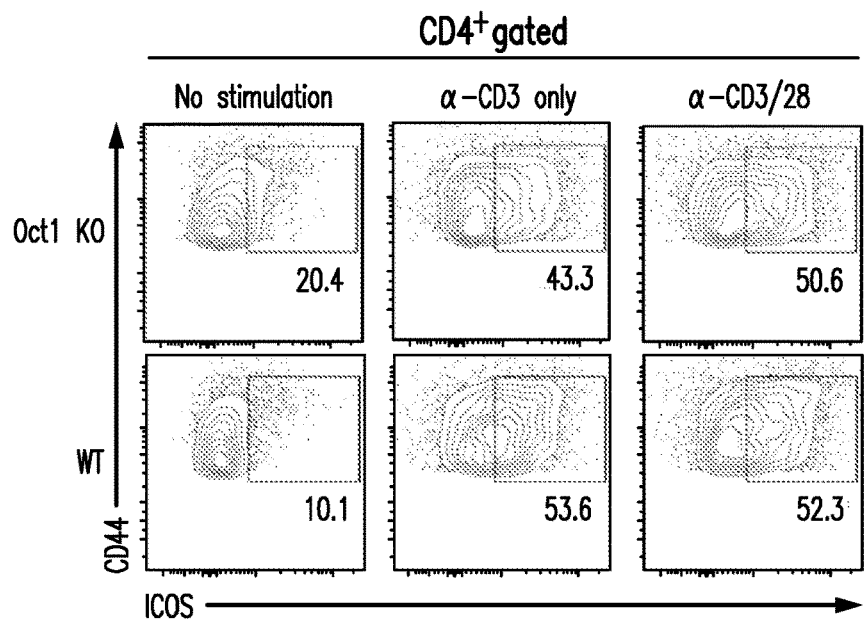
Figure 13B:
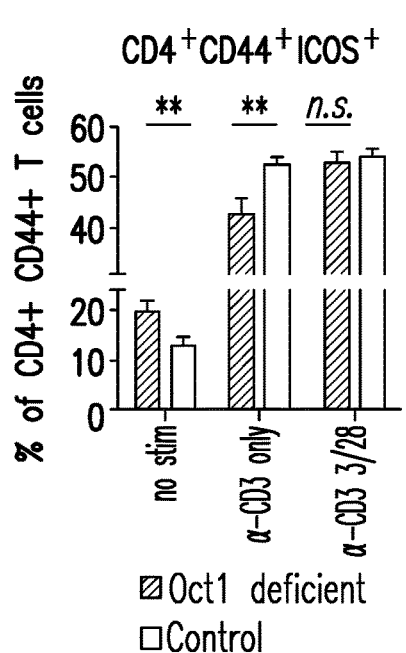
Figure 13C:
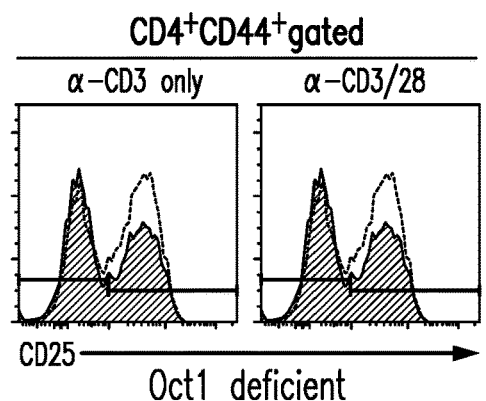
Figure 13D:
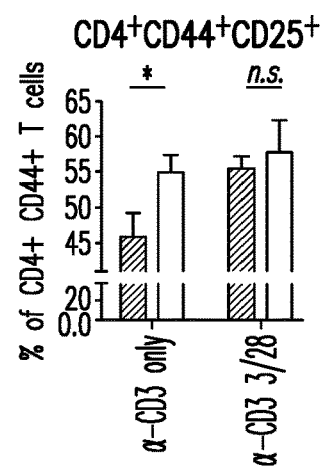

ICOS (Inducible T-cell Costimulator) has an important but complex role in the induction of T cell anergy in vitro and the development of autoimmunity in vivo (Tuettenberg A, et al. J Immunol. 2009; 182:3349-56; Dong C, et al. Nature. 2001; 409:97-101; and Dong C, et al. J Autoimmun. 2003; 21:255-60). Analyzing ICOS expression by flow cytometry, it was found that baseline ICOS levels were ~2-fold higher in naïve Oct1-deficient cells, but that no differences were apparent in fully-stimulated cells receiving anti-CD3/28 (FIGS. 13A, 13B). Interestingly, stimulating Oct1-deficient cells with anti-CD3 alone resulted in significantly reduced ICOS expression in Oct1-deficient cells compared to the control group (FIGS. 13A, 13B). Both the increased baseline ICOS expression in resting cells and decreased expression upon anergic stimulation are consistent with observed protection in an EAE model, as ICOS blockade during antigen priming (days 1-10) increases brain inflammation and promotes EAE, whereas blockade later in EAE pathogenesis (days 9-20) decreases CNS leukocyte infiltration and is protective (Dong C, et al. Nature. 2001; 409:97-101; and Rottman J B, et al. 2001; 2:605-11). Additionally, the expression of CD25, the high-affinity IL-2 receptor induced upon $CD4^+$ T cell activation (Caruso A, et al. Cytometry. 1997; 27:71-6), was decreased in Oct1-deficient cells specifically in anergic conditions lacking co-stimulation. T regulatory cells (Tregs) express CD25 and also produce IL-10, however IL-10 production in these cells was similar to control CD4+ T cells (FIG. 16), indicating that these in vitro differences are associated with effector T cells. In contrast to CD25, CD44 expression levels were similar between the groups (FIGS. 13C, 13D). These results show that ICOS and CD25 levels are altered in Oct1-deficient cells in a manner consistent with observed protection in the EAE model.

The expression of inhibitory molecules correlated with anergic responses were also analzyed. The expression of CTLA4, a checkpoint inhibitor and an anergy marker (Greenwald R J, et al. Immunity. 2001; 14:145-55), was increased by Oct1 loss in both anergic and full activation conditions (FIGS. 13E,13F). Similarly, FR4/CD73 double-positive cell frequencies were increased in Oct1-deficient cells compared to control cells in all conditions (FIGS. 13G, 13H). $CD4^+$ $CD44^+$ $FR4^{hi}CD73^{hi}$ cells are associated with anergy (Kalekar L A, et al. Nat Immunol. 2016; 17:304-14; and Martinez R J, et al. J Immunol. 2012; 188:170-81). Frequencies of IFNγ or IL-17 producing cells in Th or Th17 differentiating culture conditions were also measured to investigate if Oct1 loss affects cytokine expression levels. No differences were observed after 5 days of stimulation with $MOG_{35}$-$5_5$ peptide. Thus, in vitro stimulation of T cells lacking Oct1 results in decreased expression of surface proteins associated with activation and increased expression of proteins associated with anergy.

Figure 14A:
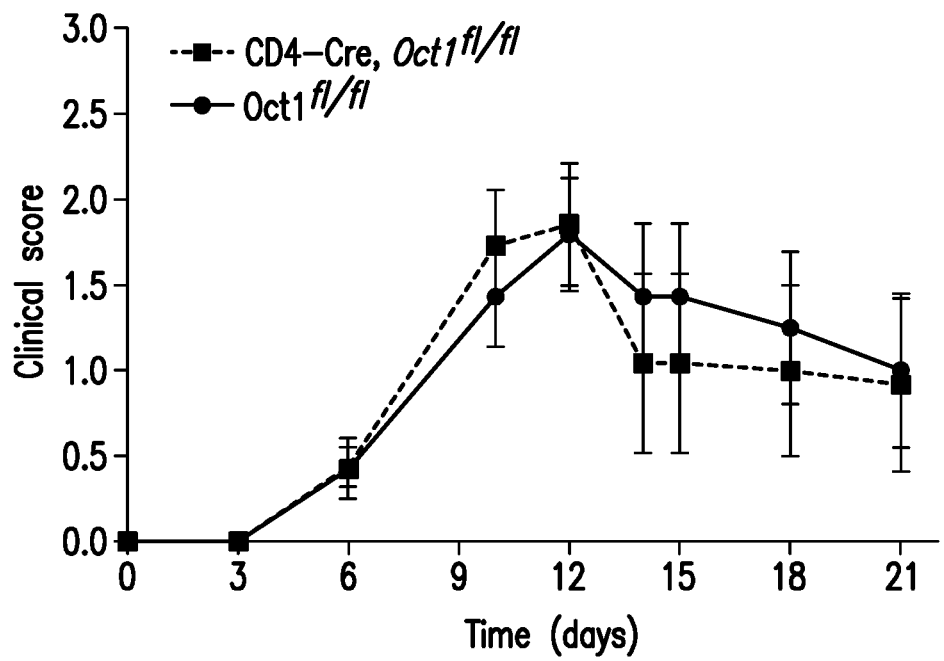
FIGS. 14A-D shows that the absence of Oct1 in T cells does not impact disease in mice infected with the neurotropic JHM strain of Mouse Hepatitis Virus (JHMV).
Figure 14B:
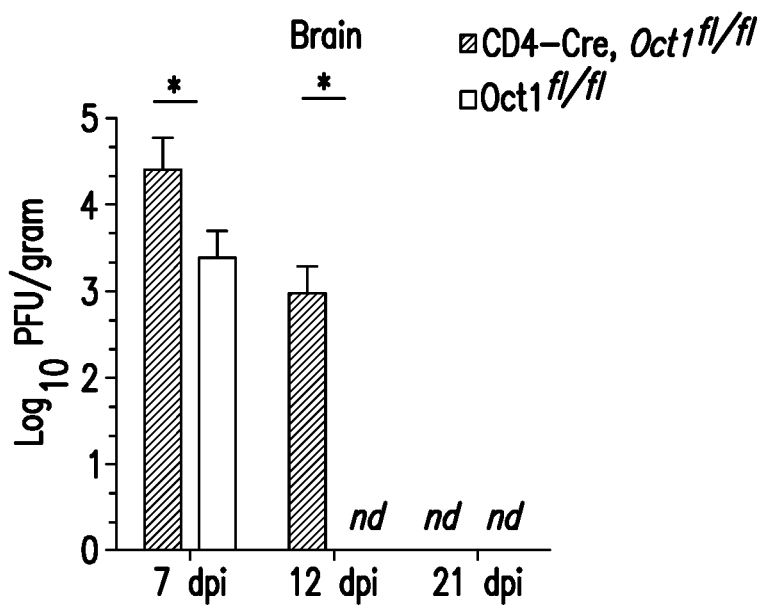
Figure 14C:
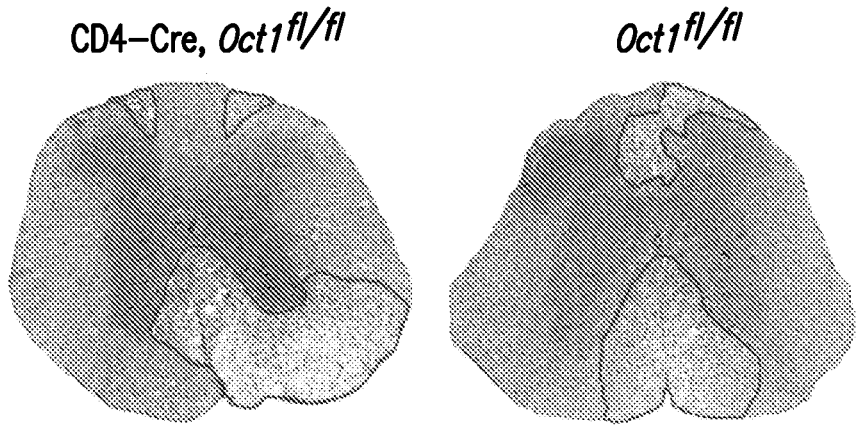
Figure 14D:
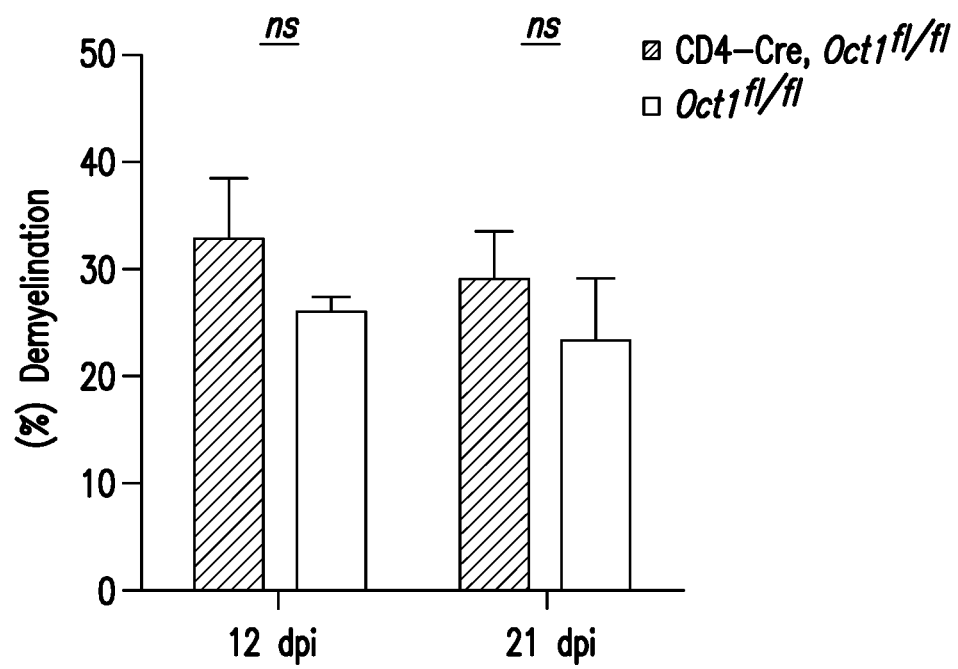
Figure 15A:
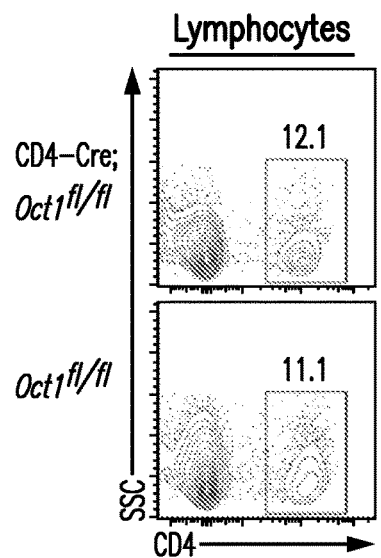
Figure 15B:
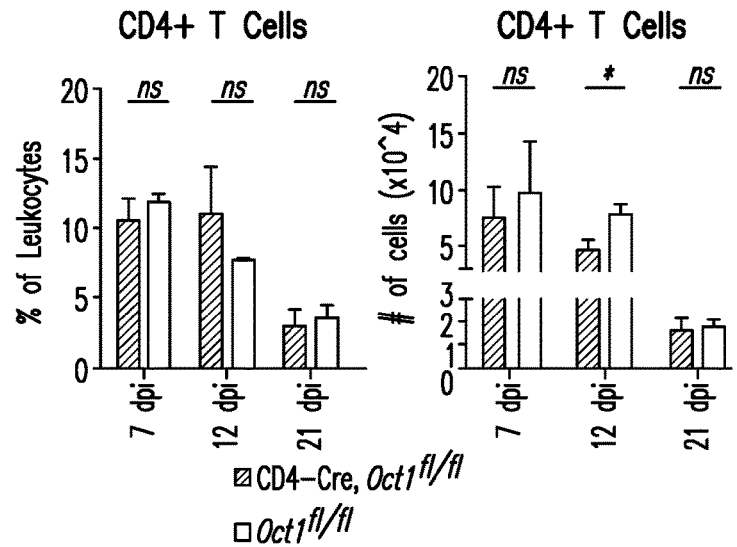
Figure 15C:
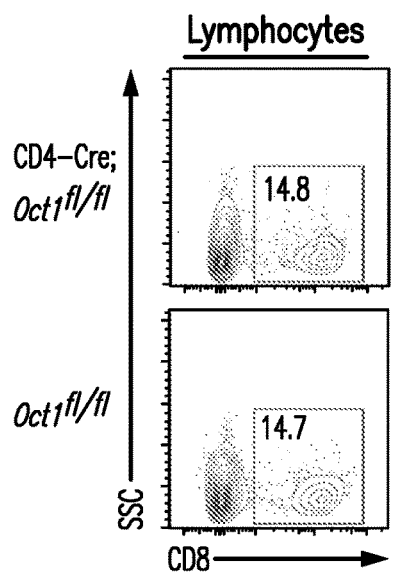
Figure 15D:
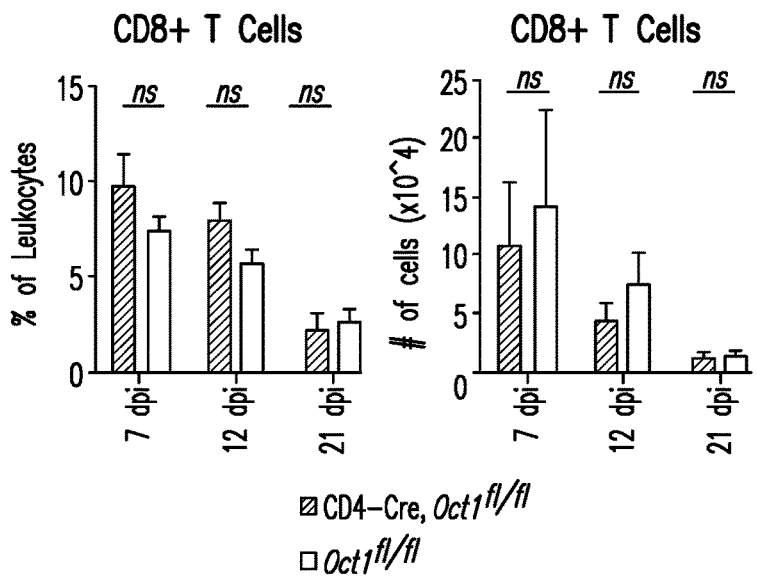
Figure 15E:
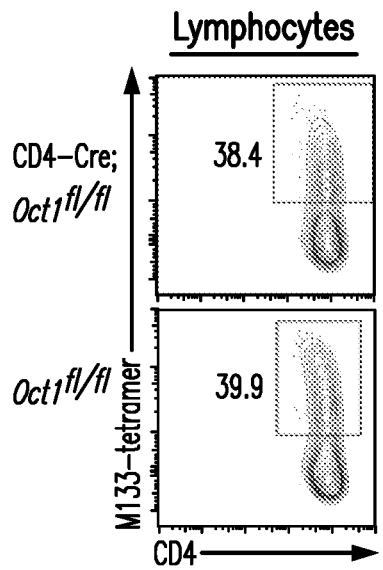
Figure 15F:
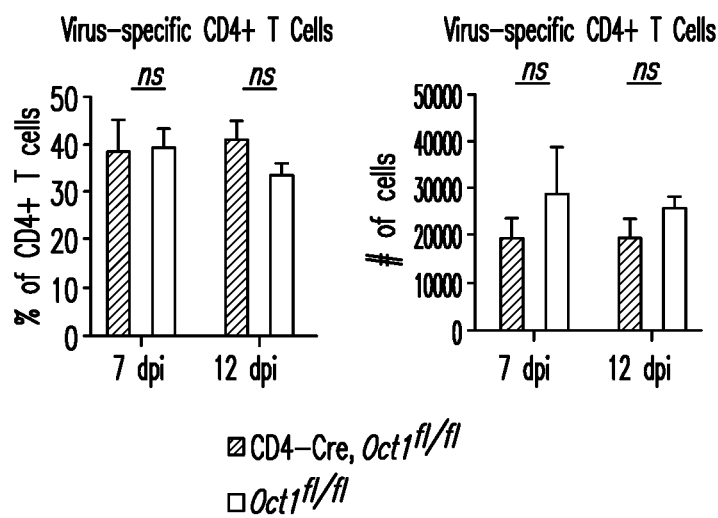
Figure 15G:
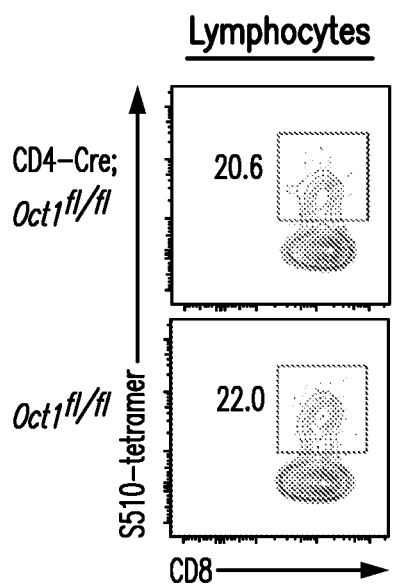
Figure 15H:
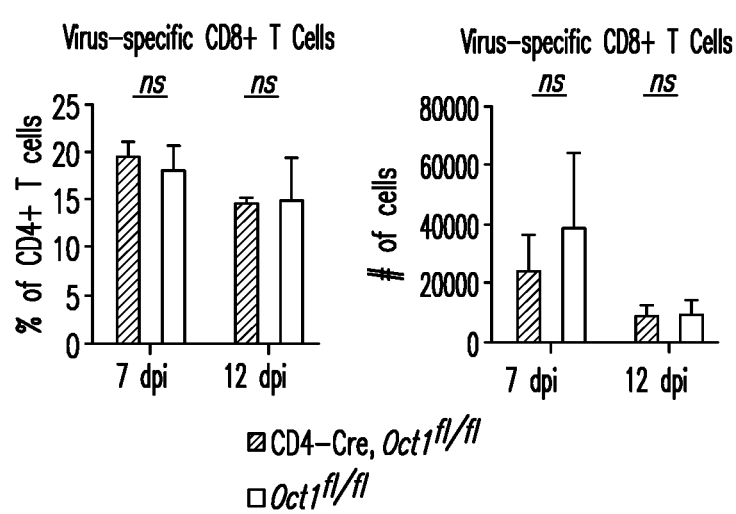

The above findings suggest that targeting Oct1 could be a viable therapeutic strategy for MS. Prior findings using acute infection with the model pathogen LCMV indicate that Oct1 in T cells is dispensable for pathogen response and clearance, but necessary for robust memory recall responses (Shakya A, et al. J Exp Med. 2015; 212:2115-31). However, the role of Oct1 in neuroinflammation caused by neurotropic viruses has not been tested. Significantly increased pathology in the case of JHMV would suggest that targeting Oct1 directly as a treatment for autoimmunity will result in unwanted side effects. To determine whether Oct1 mediates disease severity in viral-induced encephalomyelitis, responses to JHMV were studied. JHMV is a glial-tropic coronavirus and well-accepted model of viral-induced encephalomyelitis and immune-mediated demyelination (Lane T E, et al. Crit Rev Immunol. 2010; 30:119-30; Bergmann C C, et al. Nat Rev Microbiol. 2006; 4:121-32; and Liu M T, et al. Immunol Res. 2001; 24:111-9). Intracranial inoculation of C57BL/6 mice with JHMV typically results in acute encephalomyelitis, immune-mediated demyelination and hind limb paralysis. T cell responses are important for controlling JHMV replication within the CNS (Williamson J S, et al. J Virol. 1990; 64:4589-92). Age-matched Oct1$^{fl/fl}$ and CD4-Cre;Oct1$^{fl/fl}$ mice were intracranially (i.c.) inoculated with JHMV (200 PFU), and the severity of clinical disease and survival were monitored. JHMV-infected CD4-Cre;Oct1$^{fl/fl}$ mice demonstrated no differences in clinical disease severity out to 21 days (FIG. 14A). Viral titers in the brains of JHMV-infected CD4-Cre; Oct1$^{fl/fl}$ compared to control mice were studied at defined times p.i. Although viral titers were elevated in the CNS at day 7 p.i. in CD4-Cre;Oct1$^{fl/fl}$ mice compared to control animals, by day 21 p.i. viral titers were below the level of detection (~100 PFU/g tissue) in both groups (FIG. 14B). This result indicates that viral clearance is intact in Oct1 T cell-deficient mice. Supporting these findings, similar degrees of demyelination at peak disease (day 12 p.i.) and endpoint (day 21 p.i., FIGS. 14C, 14D) were observed. Numbers of infiltrating CD4$^+$ (FIG. 15A, 15B) or CD8$^+$ T cells (FIGS. 15C, 15D) in CD4-Cre;Oct1$^{fl/fl}$ mice compared to control mice were similar. Furthermore, using tetramer staining (Dickey L L, et al. J Neuroinflammation. 2016; 13:240; Marro B S, et al. J Immunol. 2016; 196:1855-64; and Blanc C A, et al. J Neuroinflammation. 2014; 11:138) no significant differences in virus-specific CD4$^+$ T cells (FIG. 15E, 15F) or CD8$^+$ T cells (FIG. 15G, 154H) was observed. The was also no difference in the percentage of CD25$^+$ cells or macrophage accumulation within the CNS of JHMV-infected mice at any time point. Proinflammatory cytokine expression in CNS T cells was studied from animals euthanized 21 days p.i. Significant levels of IL-17 expression was not observed, consistent with prior findings that Th17 cells do not play a prominent role in this model (Held K S, et al. Viral Immunol. 2008; 21:173-88; and Kapil P, et al. J Virol. 2009; 83:5978-86). IFNγ-expressing cells were present, however no significant differences were observed in either percentage or numbers, or the degree of IFNγ production (FIGS. 15, 15J). Together these data suggest that Oct1 loss in T cells does not impact neurologic disease or immune-mediated demyelination or T cell functionality in response to JHMV infection of the CNS.
Discussion The results described herein show that expression of the transcription factor Oct1 in T cells promotes CNS autoimmunity using MOG-EAE models, but minimally participates in CNS anti-viral immunity. These results suggest that targeting Oct1, and its associated activities and pathways, could be used to treat autoimmunity while sparing viral pathogen-directed immune function.

Oct1 mechanisms of transcription regulation have been studied in CD4$^+$ T cells (Shakya A, et al. J Exp Med. 2015; 212:2115-31; and Shakya A, et al. J Biol Chem. 2011; 286:450-9). Direct target genes include Il2, Ifng, Csf2 (Gmcsf), Icos and Ctla4. However, unlike NF-AT or AP-1, Oct1 is dispensable for the baseline activity of these genes. Stimulation of primary CD4$^+$ Oct1-deficient naïve T cells results in normal levels and induction kinetics of the key T cell effector cytokine IL-2 (Shakya A, et al. J Exp Med. 2015; 212:2115-31; and Shakya A, et al. J Biol Chem. 2011; 286:450-9). The normal T cell development and response to initial stimulation forms part of a potential "therapeutic window" in which targeting Oct1 and its associated pathways could be used to treat autoimmune responses with minimal side effects. Instead, Oct1 target genes show severely defective expression (100-fold or more) upon a second encounter with antigen and co-stimulatory signals (Shakya A, et al. J Exp Med. 2015; 212:2115-31; and Shakya A, et al. J Biol Chem. 2011; 286:450-9). In vivo, CD4$^+$ T cells lacking Oct1 mount a normal response to the acute viral pathogen LCMV, but fail to form memory cells in appreciable numbers. Those memory cells that are formed are defective in pathogen recall responses (Shakya A, et al. J Exp Med. 2015; 212:2115-31). Memory cells are the most prone to making proinflammatory cytokines, and memory or memory-like cells can underlie autoimmunity, even in cases of persistent self-antigen exposure (Kawakami N, et al. J Immunol. 2005; 175:69-81; Chee J, et al. J Immunol. 2014; 192:572-80; and Yeo L, et al. J Clin Invest. 2018; 128:3460-74). These findings, and the strong associations between human polymorphisms in binding sites for Oct1 and predisposition for autoimmune disease including MS (Maurano M T, et al. Science. 2012; 337:1190-5; Farh K K-H, et al. Nature. 2015; 518:337-43; van Heel D A, et al. Hum Mol Genet. 2002; 11:1281-9; Graham D S C, et al. Hum Mol Genet. 2006; 15:3195-205), suggested a possible role for Oct1 in promoting MS.

MOG-EAE is an established model of MS, driven by inoculation with autoantigen in the presence of proinflammatory signals. Using this model, the results described herein showed that loss of Oct1 in T cells protects animals from clinical symptoms of EAE. This protection was associated with decreased CLN lymphadenopathy and proinflammatory cytokine expression, as well as decreased CNS T cell infiltration and cytokine expression.

T cell tolerance can be induced centrally, through thymic selection, or peripherally, due to the activity of induced Tregs or induction of anergy (Kearney E R, et al. Immunity. 1994; 1:327-39). It was found that stimulation of CD4$^+$ T cells lacking Oct1 with CD3 alone, to mimic TCR stimulation in the absence of co-stimulatory signals, significantly increased signs of anergy compared to control Oct1-sufficient cells. Decreased ICOS and CD25 levels were observed in Oct1 deficient cells in the absence of co-stimulation, whereas no differences were observed with co-stimulation. ICOS is a co-stimulatory molecule expressed by activated T cells with an important but complex role in the induction of T cell anergy in vitro and the development of autoimmunity in vivo (Tuettenberg A, et al. J Immunol. 2009; 182:3349-56; Dong C, et al. Nature. 2001; 409:97-101; and Dong C, et al. J Autoimmun. 2003; 21:255-60). Blocking ICOS during antigen priming promotes EAE, whereas blocking ICOS later in the disease course is protective (Dong C, et al.

Nature. 2001; 409:97-101; and Rottman J B, et al. Nat Immunol. 2001; 2:605-11). Interestingly, in addition to the decreased ICOS levels observed upon anergic stimulation, it was found that unstimulated CD4+ T cells lacking Oct1 expressed baseline ICOS at higher levels. Both observations are therefore consistent with the observed protection in EAE models. Oct1 deficient cells also showed higher levels of the inhibitory receptor CTLA-4 and the anergic markers CD73 and FR4.

These findings also reveal that Oct1 is dispensable for clinical responses to JHMV-induced neurologic disease, as clinical scores and demyelination were superimposable in this model. Expression of Oct1 accelerated but was not necessary for effective viral control. However, total and antiviral T cell numbers, cytokine expression and macrophage recruitment were broadly unaffected. Examples include T cell percentages as well as numbers of cytokine-expressing cells and regulatory T cells.

Conclusion

Collectively, these results indicate that while Oct1 loss has modest effects on viral-induced inflammation, it profoundly improves responses to autoantigen-driven disease. These results suggest that targeting Oct1 and its associated upstream and downstream pathways (such as the cofactor OCA-B) may be of therapeutic benefit in autoimmunity while sparing viral pathogen-directed immune function.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound comprising:
   a peptide, wherein the peptide consists of the amino acid sequence of SEQ ID NO: 2 or SEQ ID NO: 3, wherein the peptide consisting of the amino acid sequence of SEQ ID NO: 2 is 11 amino acids in length and wherein the peptide consisting of the amino acid sequence of SEQ ID NO: 3 is 23 amino acids in length;
   a linker; and
   a cell penetrating peptide;
   wherein the peptide is fused to the linker; and wherein the linker is fused to the cell penetrating peptide.

2. The compound of claim 1, wherein the linker is a hydrocarbon linker.

3. The compound of claim 1, wherein the linker is a peptide linker.

4. The compound of claim 1, wherein the cell penetrating peptide is a TAT sequence.

5. The compound of claim 1, wherein the peptide is SEQ ID NO: 2, the linker is GSG, and the cell penetrating peptide is SEQ ID NO: 4.

6. The compound of claim 1, wherein the compound is capable of blocking the interaction of OCA-B with Jmjd1a.

7. The compound of claim 1, wherein the compound is cyclized or PEGylated.

8. A pharmaceutical composition comprising the compound of claim 1 and a pharmaceutically acceptable carrier.

9. The pharmaceutical composition of claim 8, wherein the pharmaceutical composition is formulated for intravenous administration.

10. A method of treating a subject with type 1 diabetes, the method comprising administering to the subject a compound comprising:
    a peptide, wherein the peptide consists of the amino acid sequence of SEQ ID NO: 2 or SEQ ID NO: 3, wherein the peptide consisting of the amino acid sequence of SEQ ID NO: 2 is 11 amino acids in length and wherein the peptide consisting of the amino acid sequence of SEQ ID NO: 3 is 23 amino acids in length;
    a linker; and
    a cell penetrating peptide;
    wherein the peptide is fused to the linker; and wherein the linker is fused to the cell penetrating peptide.

11. The method of claim 10, wherein the compound is in a pharmaceutically acceptable excipient.

12. The method of claim 11, wherein a therapeutically effective amount of the compound is administered.

13. A method of inhibiting OCA-B in a mammalian cell, the method comprising treating the cell with the compound of claim 1.

14. The method of claim 13, wherein the cell is an immune system cell.

15. A compound that blocks the interaction of OCA-B and Jmjd1a, wherein the compound comprises:

a peptide, wherein the peptide consists of the amino acid sequence of SEQ ID NO: 2 or SEQ ID NO: 3, wherein the peptide consisting of the amino acid sequence of SEQ ID NO: 2 is 11 amino acids in length and wherein the peptide consisting of the amino acid sequence of SEQ ID NO: 3 is 23 amino acids in length;

a linker; and a cell penetrating peptide;

wherein the peptide is fused to the linker; and wherein the linker is fused to the cell penetrating peptide.

16. The compound of claim 15, wherein the linker is GSG and the cell penetrating peptide is SEQ ID NO: 4.

* * * * *

```
                          SEQUENCE LISTING

<160> NUMBER OF SEQ ID NOS: 36

<210> SEQ ID NO 1
    <211> LENGTH: 14
    <212> TYPE: PRT
    <213> ORGANISM: Artificial Sequence
    <220> FEATURE:
    <223> OTHER INFORMATION: Synthetic construct

<400> SEQUENCE: 1

Ala Arg Pro Tyr Gln Gly Val Arg Val Lys Glu Pro Val Lys
    1               5                   10

<210> SEQ ID NO 2
    <211> LENGTH: 11
    <212> TYPE: PRT
    <213> ORGANISM: Artificial Sequence
    <220> FEATURE:
    <223> OTHER INFORMATION: Synthetic construct

<400> SEQUENCE: 2

Val Lys Glu Leu Leu Arg Arg Lys Arg Gly His
    1               5                   10

<210> SEQ ID NO 3
    <211> LENGTH: 23
    <212> TYPE: PRT
    <213> ORGANISM: Artificial Sequence
    <220> FEATURE:
    <223> OTHER INFORMATION: Synthetic construct

<400> SEQUENCE: 3

Ala Arg Pro Tyr Gln Gly Val Arg Val Lys Glu Pro Val Lys Glu Leu
    1               5                   10                  15

Leu Arg Arg Lys Arg Gly His
                20

<210> SEQ ID NO 4
    <211> LENGTH: 12
    <212> TYPE: PRT
    <213> ORGANISM: Artificial Sequence
    <220> FEATURE:
    <223> OTHER INFORMATION: Synthetic construct

<400> SEQUENCE: 4

Gly Arg Lys Lys Arg Arg Gln Arg Arg Arg Gly Tyr
    1               5                   10
```

<210> SEQ ID NO 5
<211> LENGTH: 256
<212> TYPE: PRT
<213> ORGANISM: Mus musculus

<400> SEQUENCE: 5

```
Met Leu Trp Gln Lys Ser Thr Ala Pro Glu Gln Ala Pro Ala Pro Pro
 1               5                  10                  15

Arg Pro Tyr Gln Gly Val Arg Val Lys Glu Pro Val Lys Glu Leu Leu
            20                  25                  30

Arg Arg Lys Arg Gly His Thr Ser Val Gly Ala Ala Gly Pro Pro Thr
        35                  40                  45

Ala Val Val Leu Pro His Gln Pro Leu Ala Thr Tyr Ser Thr Val Gly
    50                  55                  60

Pro Ser Cys Leu Asp Met Glu Val Ser Ala Ser Thr Val Thr Glu Glu
65                  70                  75                  80

Gly Thr Leu Cys Ala Gly Trp Leu Ser Gln Pro Ala Pro Ala Thr Leu
                85                  90                  95

Gln Pro Leu Ala Pro Trp Thr Pro Tyr Thr Glu Tyr Val Ser His Glu
            100                 105                 110

Ala Val Ser Cys Pro Tyr Ser Thr Asp Met Tyr Val Gln Pro Val Cys
        115                 120                 125

Pro Ser Tyr Thr Val Val Gly Pro Ser Ser Val Leu Thr Tyr Ala Ser
    130                 135                 140

Pro Pro Leu Ile Thr Asn Val Thr Pro Arg Ser Thr Ala Thr Pro Ala
145                 150                 155                 160

Val Gly Pro Gln Leu Glu Gly Pro Glu His Gln Ala Pro Leu Thr Tyr
                165                 170                 175

Phe Pro Trp Pro Gln Pro Leu Ser Thr Leu Pro Thr Ser Ser Leu Gln
            180                 185                 190

Tyr Gln Pro Pro Ala Pro Thr Leu Ser Gly Pro Gln Phe Val Gln Leu
        195                 200                 205

Pro Ile Ser Ile Pro Glu Pro Val Leu Gln Asp Met Asp Asp Pro Arg
    210                 215                 220

Arg Ala Ile Ser Ser Leu Thr Ile Asp Lys Leu Leu Leu Glu Glu Glu
225                 230                 235                 240

Glu Ser Asn Thr Tyr Glu Leu Asn His Thr Leu Ser Val Glu Gly Phe
                245                 250                 255
```

<210> SEQ ID NO 6
<211> LENGTH: 16
<212> TYPE: PRT
<213> ORGANISM: Artificial Sequence
<220> FEATURE:
<223> OTHER INFORMATION: Penetratin

<400> SEQUENCE: 6

```
Arg Gln Ile Lys Ile Trp Phe Gln Asn Arg Arg Met Lys Trp Lys Lys
 1               5                  10                  15
```

<210> SEQ ID NO 7
<211> LENGTH: 256
<212> TYPE: PRT
<213> ORGANISM: Homo sapiens

<400> SEQUENCE: 7

```
Met Leu Trp Gln Lys Pro Thr Ala Pro Glu Gln Ala Pro Ala Pro Ala
```

```
            1               5                  10                 15
        Arg Pro Tyr Gln Gly Val Arg Val Lys Glu Pro Val Lys Glu Leu Leu
                       20                  25                  30
        Arg Arg Lys Arg Gly His Ala Ser Ser Gly Ala Ala Pro Ala Pro Thr
                       35                  40                  45
        Ala Val Val Leu Pro His Gln Pro Leu Ala Thr Tyr Thr Thr Val Gly
                       50                  55                  60
        Pro Ser Cys Leu Asp Met Glu Gly Ser Val Ser Ala Val Thr Glu Glu
        65                  70                  75                  80
        Ala Ala Leu Cys Ala Gly Trp Leu Ser Gln Pro Thr Pro Ala Thr Leu
                            85                  90                  95
        Gln Pro Leu Ala Pro Trp Thr Pro Tyr Thr Glu Tyr Val Pro His Glu
                       100                 105                 110
        Ala Val Ser Cys Pro Tyr Ser Ala Asp Met Tyr Val Gln Pro Val Cys
                       115                 120                 125
        Pro Ser Tyr Thr Val Val Gly Pro Ser Ser Val Leu Thr Tyr Ala Ser
                       130                 135                 140
        Pro Pro Leu Ile Thr Asn Val Thr Thr Arg Ser Ser Ala Thr Pro Ala
        145                 150                 155                 160
        Val Gly Pro Pro Leu Glu Gly Pro Glu His Gln Ala Pro Leu Thr Tyr
                            165                 170                 175
        Phe Pro Trp Pro Gln Pro Leu Ser Thr Leu Pro Thr Ser Thr Leu Gln
                       180                 185                 190
        Tyr Gln Pro Pro Ala Pro Ala Leu Pro Gly Pro Gln Phe Val Gln Leu
                       195                 200                 205
        Pro Ile Ser Ile Pro Glu Pro Val Leu Gln Asp Met Glu Asp Pro Arg
        210                 215                 220
        Arg Ala Ala Ser Ser Leu Thr Ile Asp Lys Leu Leu Leu Glu Glu Glu
        225                 230                 235                 240
        Asp Ser Asp Ala Tyr Ala Leu Asn His Thr Leu Ser Val Glu Gly Phe
                            245                 250                 255

<210> SEQ ID NO 8
<211> LENGTH: 13
<212> TYPE: PRT
<213> ORGANISM: Artificial Sequence
<220> FEATURE:
<223> OTHER INFORMATION: Synthetic construct

<400> SEQUENCE: 8

Gly Arg Lys Lys Arg Arg Gln Arg Arg Pro Pro Gln
1               5                   10

<210> SEQ ID NO 9
<211> LENGTH: 26
<212> TYPE: PRT
<213> ORGANISM: Artificial Sequence
<220> FEATURE:
<223> OTHER INFORMATION: Synthetic construct

<400> SEQUENCE: 9

Glu Pro Val Lys Glu Pro Val Lys Lys Glu Leu Leu Arg Arg Lys Arg
1               5                   10                  15

Gly His Ser Val Gly Ala Ala Gly Pro Pro
            20                  25

<210> SEQ ID NO 10
<211> LENGTH: 26
```

```
<212> TYPE: PRT
<213> ORGANISM: Artificial Sequence
<220> FEATURE:
<223> OTHER INFORMATION: Synthetic construct

<400> SEQUENCE: 10

Val Lys Glu Leu Leu Arg Arg Lys Arg Gly His Gly Ser Gly Gly Arg
1               5                   10                  15

Lys Lys Arg Arg Gln Arg Arg Arg Gly Tyr
            20                  25

<210> SEQ ID NO 11
<211> LENGTH: 11
<212> TYPE: PRT
<213> ORGANISM: Artificial Sequence
<220> FEATURE:
<223> OTHER INFORMATION: Synthetic construct

<400> SEQUENCE: 11

Ala Lys Glu Leu Leu Arg Arg Lys Arg Gly His
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic construct

<400> SEQUENCE: 12

Val Ala Glu Leu Leu Arg Arg Lys Arg Gly His
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic construct

<400> SEQUENCE: 13

Val Lys Ala Leu Leu Arg Arg Lys Arg Gly His
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic construct

<400> SEQUENCE: 14

Val Lys Glu Ala Leu Arg Arg Lys Arg Gly His
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic construct

<400> SEQUENCE: 15

Val Lys Glu Leu Ala Arg Arg Lys Arg Gly His
1               5                   10
```

```
<210> SEQ ID NO 16
<211> LENGTH: 11
<212> TYPE: PRT
<213> ORGANISM: Artificial Sequence
<220> FEATURE:
<223> OTHER INFORMATION: Synthetic construct

<400> SEQUENCE: 16

Val Lys Glu Leu Leu Ala Arg Lys Arg Gly His
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic construct

<400> SEQUENCE: 17

Val Lys Glu Leu Leu Arg Ala Lys Arg Gly His
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic construct

<400> SEQUENCE: 18

Val Lys Glu Leu Leu Arg Arg Ala Arg Gly His
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic construct

<400> SEQUENCE: 19

Val Lys Glu Leu Leu Arg Arg Lys Ala Gly His
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic construct

<400> SEQUENCE: 20

Val Lys Glu Leu Leu Arg Arg Lys Arg Ala His
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic construct

<400> SEQUENCE: 21

Val Lys Glu Leu Leu Arg Arg Lys Arg Gly Ala
1               5                   10

<210> SEQ ID NO 22
```

```
<211> LENGTH: 11
<212> TYPE: PRT
<213> ORGANISM: Artificial Sequence
<220> FEATURE:
<223> OTHER INFORMATION: Synthetic construct

<400> SEQUENCE: 22

Cys Lys Glu Leu Leu Arg Arg Lys Arg Gly His
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic construct

<400> SEQUENCE: 23

Val Cys Glu Leu Leu Arg Arg Lys Arg Gly His
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic construct

<400> SEQUENCE: 24

Val Lys Cys Leu Leu Arg Arg Lys Arg Gly His
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic construct

<400> SEQUENCE: 25

Val Lys Glu Cys Leu Arg Arg Lys Arg Gly His
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic construct

<400> SEQUENCE: 26

Val Lys Glu Leu Cys Arg Arg Lys Arg Gly His
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic construct

<400> SEQUENCE: 27

Val Lys Glu Leu Leu Cys Arg Lys Arg Gly His
1               5                   10

<210> SEQ ID NO 28
<211> LENGTH: 11
```

```
<212> TYPE: PRT
<213> ORGANISM: Artificial Sequence
<220> FEATURE:
<223> OTHER INFORMATION: Synthetic construct

<400> SEQUENCE: 28

Val Lys Glu Leu Leu Arg Cys Lys Arg Gly His
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic construct

<400> SEQUENCE: 29

Val Lys Glu Leu Leu Arg Arg Cys Arg Gly His
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic construct

<400> SEQUENCE: 30

Val Lys Glu Leu Leu Arg Arg Lys Cys Gly His
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic construct

<400> SEQUENCE: 31

Val Lys Glu Leu Leu Arg Arg Lys Arg Cys His
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic construct

<400> SEQUENCE: 32

Val Lys Glu Leu Leu Arg Arg Lys Arg Gly Cys
1               5                   10

<210> SEQ ID NO 33
<211> LENGTH: 20
<212> TYPE: PRT
<213> ORGANISM: Artificial Sequence
<220> FEATURE:
<223> OTHER INFORMATION: Synthetic construct

<400> SEQUENCE: 33

Leu Ser Ser Pro Ser Ala Leu Asn Ser Pro Gly Ile Glu Gly Leu Ser
1               5                   10                  15

Arg Arg Arg Lys
            20
```

```
<210> SEQ ID NO 34
<211> LENGTH: 20
<212> TYPE: PRT
<213> ORGANISM: Artificial Sequence
<220> FEATURE:
<223> OTHER INFORMATION: Synthetic construct

<400> SEQUENCE: 34

Ala Ala Leu Leu Ser Ser Leu Asn Glu Leu Gly Glu Arg Gln Leu Val
1               5                   10                  15

His Trp Lys Trp
            20

<210> SEQ ID NO 35
<211> LENGTH: 21
<212> TYPE: PRT
<213> ORGANISM: Artificial Sequence
<220> FEATURE:
<223> OTHER INFORMATION: Synthetic construct

<400> SEQUENCE: 35

Met Glu Val Gly Trp Tyr Arg Ser Pro Phe Ser Arg Val Val His Leu
1               5                   10                  15

Tyr Arg Asn Gly Lys
            20

<210> SEQ ID NO 36
<211> LENGTH: 9
<212> TYPE: PRT
<213> ORGANISM: Artificial Sequence
<220> FEATURE:
<223> OTHER INFORMATION: Synthetic construct

<400> SEQUENCE: 36

Cys Leu Leu Arg Arg Lys Arg Gly Cys
1               5
```